(12) United States Patent
Manford

(10) Patent No.: US 10,532,041 B2
(45) Date of Patent: Jan. 14, 2020

(54) FORMULATION COMPRISING GLYCOPYRROLATE, METHOD AND APPARATUS

(71) Applicant: Vectura Limited, Chippenham, Wiltshire (GB)

(72) Inventor: Fergus Manford, Chippenham (GB)

(73) Assignee: Vectura Limited, Wiltshire (GB)

( * ) Notice: Subject to any disclaimer, the term of this patent is extended or adjusted under 35 U.S.C. 154(b) by 0 days.

(21) Appl. No.: 15/509,769

(22) PCT Filed: Sep. 9, 2015

(86) PCT No.: PCT/EP2015/070660
§ 371 (c)(1),
(2) Date: Mar. 8, 2017

(87) PCT Pub. No.: WO2016/038116
PCT Pub. Date: Mar. 17, 2016

(65) Prior Publication Data
US 2017/0258762 A1    Sep. 14, 2017

(30) Foreign Application Priority Data
Sep. 9, 2014  (EP) .................... 14184164

(51) Int. Cl.
| | | |
|---|---|---|
| *A61K 31/40* | (2006.01) | |
| *A61K 31/137* | (2006.01) | |
| *A61K 31/4704* | (2006.01) | |
| *A61K 31/573* | (2006.01) | |
| *A61K 9/00* | (2006.01) | |
| *A61K 9/50* | (2006.01) | |
| *A61K 9/51* | (2006.01) | |
| *A61K 31/138* | (2006.01) | |

(52) U.S. Cl.
CPC ............ *A61K 31/40* (2013.01); *A61K 9/0075* (2013.01); *A61K 9/5015* (2013.01); *A61K 9/5192* (2013.01); *A61K 31/137* (2013.01); *A61K 31/138* (2013.01); *A61K 31/4704* (2013.01); *A61K 31/573* (2013.01)

(58) Field of Classification Search
None
See application file for complete search history.

(56) References Cited

U.S. PATENT DOCUMENTS

| 7,866,878 B2 * | 1/2011 | Howe ................ B06B 1/161 366/108 |
|---|---|---|
| 8,235,314 B2 | 8/2012 | Lee |
| 2004/0121003 A1 | 6/2004 | Chickering, III et al. |
| 2005/0079138 A1 | 4/2005 | Chickering, III et al. |
| 2007/0243260 A1 | 10/2007 | Snape et al. |
| 2008/0020048 A1 | 1/2008 | Snape et al. |
| 2008/0063719 A1 | 3/2008 | Morton et al. |
| 2008/0127972 A1 | 6/2008 | Morton |
| 2010/0015238 A1 | 1/2010 | Mueller-Walz |
| 2012/0022127 A1 | 1/2012 | Allmendinger |
| 2012/0160944 A1 | 6/2012 | Dodd et al. |
| 2014/0080890 A1 | 3/2014 | Snape et al. |

FOREIGN PATENT DOCUMENTS

| CA | 2479652 | 7/2012 |
|---|---|---|
| JP | 2006-298904 | 11/2006 |
| JP | 2007-536361 | 12/2007 |
| WO | WO1995/005805 | 3/1995 |
| WO | WO1999/054048 | 10/1999 |
| WO | WO2000/032165 | 6/2000 |
| WO | WO2000/032313 | 6/2000 |
| WO | WO2001/076560 | 10/2001 |
| WO | WO2001/076575 | 10/2001 |
| WO | WO2002/008470 | 1/2002 |
| WO | WO2002/043701 | 6/2002 |
| WO | WO2002/043702 | 6/2002 |
| WO | WO2002/045682 | 6/2002 |
| WO | WO2004/054545 | 7/2004 |
| WO | WO2005/025536 | 3/2005 |
| WO | WO2005/025540 | 3/2005 |
| WO | WO2005/089717 | 9/2005 |
| WO | WO2005/110402 | 11/2005 |
| WO | WO2007/008480 | 1/2007 |
| WO | WO2007/057221 | 5/2007 |
| WO | WO2007/057222 | 5/2007 |
| WO | WO2007/057223 | 5/2007 |
| WO | WO2007/068443 | 6/2007 |
| WO | WO2008/000482 | 1/2008 |

(Continued)

OTHER PUBLICATIONS

International Search Report for International Application No. PCT/EP2015/070660, dated Nov. 26, 2015.
Written Opinion of the International Search Authority for International Application No. PCT/EP2015/070660.
Advances in Powder Micronization Technology for the Pharmaceutical Industry; Hosokawa Micron Powder Systems; The Journal of Pharmaceutical Processing.
Brodka-Pfeiffer et al., Conditioning Following Powder Micronization: Influence on Particle Growth of Salbutamol Sulfate; Drug Development and Industrial Pharmacy, vol. 29, No. 10, pp. 1077-1084, 2003.

(Continued)

*Primary Examiner* — David J Blanchard
*Assistant Examiner* — Daniel F. Coughlin
(74) *Attorney, Agent, or Firm* — Finnegan, Henderson, Farabow, Garrett & Dunner, LLP

(57) ABSTRACT

A method is disclosed for making a pharmaceutical composition for pulmonary administration comprising co-jet milling glycopyrrolate and magnesium stearate, wherein the co-jet milled glycopyrrolate and magnesium stearate is then subjected to a conditioning step which includes exposure of the co-jet milled glycopyrrolate and magnesium stearate to humidity. A composition made by this method is also disclosed.

48 Claims, 23 Drawing Sheets

(56) References Cited

FOREIGN PATENT DOCUMENTS

| WO | WO2008/025787 | 3/2008 |
| WO | WO2008/084312 | 7/2008 |
| WO | WO 2008/096111 | 8/2008 |
| WO | WO 2009/061273 | 5/2009 |
| WO | WO2009/074662 | 6/2009 |
| WO | WO2009/074666 | 6/2009 |
| WO | WO2010/115937 | 10/2010 |
| WO | WO2011/131663 | 10/2011 |
| WO | WO2012/028663 | 3/2012 |
| WO | WO 2012/110770 A2 | 8/2012 |
| WO | WO 2012/158166 | 11/2012 |
| WO | WO2013/144655 | 10/2013 |
| WO | WO2014/190204 | 11/2013 |
| WO | WO2014/007766 | 1/2014 |
| WO | WO2014/007767 | 1/2014 |
| WO | WO2014/155134 | 10/2014 |
| WO | WO2015/094927 | 6/2015 |

OTHER PUBLICATIONS

Economical using steam; Dry grinding jet mills overcome the limits to the nanometre range, Powtech/Technopharm, 2010.
Experimental data introduced during examination of P1018EPOO; Dated Sep. 26, 2011; Vectura Limited.
Hosakowa • AFG Fluidised Bed Opposed Jet Mill http://www.hosokawa.co.uk/product/afg-fluidised-bed-opposed-jet-mill/.
Hosakowa Brochure: Alpine fluidised bed opposed jet mill; Hosokawa Alpine Aktiengesellschaft; 2010.
Hosakowa Brochure: Pharmaceutical Lab Mill System with Spiral Jet Mill 100 AS.
Hosakowa Brochure: Pharmaceutical Lab Mill System with Spiral Jet Mill 100 AS (Publication date unknown).
Hosakowa Brochure: The New Generation Fluidised-Bed Jet Mills AFG; 1999; Hosokawa Alpine Aktiengesellschaft.
Inhalation Drug Delivery. Techniques and Products.; Edited by Paolo Colombo; Publisher: Wiley; Section 4.3 "Specialized Milling", 2013.
The Jet Pulverizer Co website • FAQs • c. 2014 • http://www.jetpulverizer.com/frequently-asked-questions/#milling.
Thread: Hosokawa Jet Mill & Ingersoll Rand Compressor; http://forum.bulk-online.com; Jun. 2013.
Ticehurst et al., Characterisation of the influence of micronisation on the crystallinity and physical stability of revatropate hydrobromide; International Journal of Pharmaceutics 193 (2000) 247-259.
Ward et al., Process-Induced Crystallinity Changes in Albuterol Sulfate, Pharmaceutical Research, vol. 12, No. 5, 1995.
Zeng et al; 2003; Particulate interactions in dry powder formulations.

* cited by examiner

US 10,532,041 B2

FORMULATION COMPRISING GLYCOPYRROLATE, METHOD AND APPARATUS

This application is a national stage filing under 35 U.S.C. § 371 of International Application No. PCT/EP2015/070660, filed on Sep. 9, 2015, which claims priority of European Patent Application No. 14184164.3 filed Sep. 9, 2014. The contents of these applications are each incorporated herein by reference.

INTRODUCTION

The present invention relates to inhalable pharmaceutical compositions comprising the antimuscarinic agent glycopyrrolate. In particular, the present invention relates to dry powder compositions which exhibit excellent physical stability and aerosol performance over time, and provides an improved process for preparing inhalable dry powder formulations of glycopyrrolate.

BACKGROUND

Glycopyrrolate is an antimuscarinic agent which is useful in the treatment of conditions such as chronic obstructive pulmonary disease (COPD), asthma, cystic fibrosis (CF) and related airway diseases. Glycopyrrolate is also useful as a heart rate lowering agent when administered by inhalation to patients, in particular patients with conditions such as chronic obstructive pulmonary disease (COPD), asthma, cystic fibrosis (CF) and related airway diseases. It is known to provide glycopyrrolate formulations in the form of dry powder formulations, for administration using dry powder inhalers. Frequently salts of glycopyrrolate are used, such as glycopyrronium bromide.

Glycopyrrolate is commercially available or may be prepared using the method described in U.S. Pat. No. 2,956,062. The most physically stable configuration is when the particles are crystalline and they contain few amorphous regions on their surfaces.

Glycopyrrolate has been found to have an acute problem with respect to its stability, especially immediately following a conventional micronisation process.

Micronisation of glycopyrrolate involves the milling of a relatively coarse source powder into a system which involves multiple high-speed or high energy collisions. Typically, source powders of unmicronised glycopyrrolate will exist in particle sizes substantially greater than 10 µm, with typical distributions resembling D10>10 µm, D50>90, D90>250 µm. The primary objective of the micronisation process is to reduce the primary particle size to a size which is small enough to be delivered to the respiratory airways. For example, it is known that a suitable size may be where the majority of the particles as measured by mass or volume fall within the inhalable range of 0.1 µm to 10 µm, preferably 0.1 µm to 6 µm or more preferably 0.5 µm to 5 µm.

The multiple collisions that occur with high-speed or high energy micronisation provide the milling action which is required to break the particles down to the appropriate size. It is also well known that such milling action may also induce the generation of non-crystalline material, especially on the surface of the particles where particles have collided either with each other as in the case of jet milling, or with the milling medium as in the case of ball milling, or with the milling machine as in the case of knife milling. Such non-crystalline material may be amorphous material.

The presence of non-crystalline or amorphous regions in glycopyrrolate material can lead to significant physical instability.

International patent application WO2001076575 discloses a pharmaceutical composition for pulmonary delivery comprising glycopyrrolate in a controlled release formulation, wherein, on administration, the glycopyrrolate exerts its pharmacological effect over a period greater than 12 hours.

US publication number US 2014/0080890 discloses glycopyrrolate for use as a heart rate lowering agent and more particularly, but not exclusively, for use in patients suffering from respiratory conditions such as chronic obstructive pulmonary disease. It discloses conducting micronisation under increased Relative Humidity (RH) to reduce the formation of amorphous material.

International patent application WO2005105043 discloses dry powder compositions which exhibit improved stability over time, and methods for producing the same.

International patent application WO2008000482 discloses a process for preparing dry powder formulations of a glycopyrronium salt for inhalation that have good stability. The process involves (a) micronising a glycopyrronium salt together with an anti-adherent agent, and (b) admixing carrier particles to form the dry powder formulation.

International patent application WO2008000482 discloses a process for reducing the tendency of a drug substance to aggregate and/or agglomerate during storage. The process involves micronising the drug substance to give a mean particle size of less than about 10 µm, and exposing the micronised drug substance to a dry environment at an elevated temperature between 40° C. and 120° C. for at least six hours.

It has been also suggested that conducting micronisation with humidified air or other gas may help to reduce the generation of amorphous materials. Both WO1999054048 and WO2000032165 disclose that milling crystalline particles, especially medicament powders intended for administration by inhalation under increased humidity can reduce the generation of amorphous material.

WO2000032313 discloses the milling of highly crystalline material, exemplified with triamcinolone acetonide at reduced temperature using helium or a mixture of helium and another gas in order to reduce the formation of amorphous material.

SUMMARY OF THE INVENTION

The present application teaches a method of making dry powder formulation, the method comprising co-jet milling unmicronised glycopyrrolate and magnesium stearate with gas having a humidity below 20% Relative Humidity to produce micronized composite particles, wherein the micronized composite particles are then subjected to a conditioning step which includes exposure of the micronized composite particles to humidity at temperatures between 5° C. to 88° C. for at least 60 minutes.

In another embodiment of the present invention, there is disclosed a formulation comprising co-jet milled and then co-conditioned particles comprising unmicronised glycopyrrolate and magnesium stearate obtained or obtainable according to methods disclosed herein, optionally for use in a treatment of a respiratory disease, or for use in the preparation of a medicament for the treatment of a respiratory disease.

In another embodiment of the present invention, there is disclosed a method for making a dry powder formulation, the method comprising co-jet milling unmicronised glycopyrrolate and magnesium stearate with desiccated milling gas having a humidity below 20% RH to produce micronized composite particles, wherein the micronized composite particles are then subjected to a conditioning step which includes exposure of the micronized composite particles to humidity at temperatures between 5° C. to 88° C. for at least 60 minutes.

In another embodiment of the present invention, there is disclosed a method for making a dry powder formulation, the method comprising co-jet milling unmicronised glycopyrrolate and magnesium stearate with desiccated milling gas having a humidity below 20% RH to produce micronized composite particles, wherein the micronized composite particles are then subjected to a conditioning step which includes exposure of the micronized composite particles to humidity at temperatures between 5° C. to 88° C. for at least 90 minutes.

In another embodiment of the present invention, there is disclosed a method wherein the conditioning is initiated within 30 minutes of completing the milling, within 25 minutes, within 20 minutes, within 15 minutes, preferably within 10 minutes, more preferably within 5 minutes, most preferably the conditioning is initiated immediately after completing the co-jet milling of the glycopyrrolate and magnesium stearate.

In another embodiment of the present invention, there is disclosed a method wherein the fraction of the conditioned co-jet milled formulation which is greater than 10 μm is less than 20% by volume or mass, preferably wherein the fraction which is greater than 10 μm is less than 15% by volume or mass, more preferably wherein the fraction which is greater than 10 μm is less than 10% by volume or mass, or more preferably wherein the fraction which is greater than 10 μm is less than 5% by volume or mass, immediately after the co-jet milling and after the conditioning process as suitably determined by a MALVERN MASTERSIZER® or similar laser diffraction equipment.

In another embodiment of the present invention, there is disclosed a method wherein the magnesium stearate is co-jet milled with glycopyrrolate in an amount of from 1 to 25% (w/w), more preferably from 2 to 20% (w/w), more preferably 3 to 15% (w/w), more preferably 4 to 10% (w/w) but most preferably from 5 to 7.5% (w/w) by weight of the co-jet milled combination of glycopyrrolate and magnesium stearate.

In another embodiment of the present invention, there is disclosed a method wherein the conditioning humidity is in the range of 10%-95% RH, preferably 30-90% RH, 45-90% RH or 50-88% RH or more preferably 60-87% RH.

In another embodiment of the present invention, there is disclosed a method wherein the conditioning further comprises subjecting the micronized composite particles to a ventilating atmosphere having RH in the range of 10%-95% RH, preferably 30-90% RH, 45-90% RH or 50-88% RH or more preferably 60-87%, preferably wherein the atmosphere is air. Wherein ventilating atmosphere passes over and through the micronized composite particles at a rate of less than 100 cm$^3$/s, less than 10 cm$^3$/s, less than 5 cm$^3$/s, less than 2 cm$^3$/s, less than 1 cm$^3$/s, preferably less than 0.8 cm$^3$/s, preferably less than 0.6 cm$^3$/s, preferably less than 0.4 cm$^3$/s, preferably less than 0.2 cm$^3$/s, preferably less than 0.1 cm$^3$/s, more preferably about 0.001 cm$^3$/s. Wherein the volume ratio of ventilating atmosphere to poured bulk powder is more than 1:1, preferably more than more than 10:1, preferably more than more than 100:1, preferably more than more than 1,000:1, preferably more than 10,000:1, preferably more than 100,000:1, preferably more than 1,000,000:1, more preferably more than 10,000,000:1.

In another embodiment of the present invention, there is disclosed a method wherein the conditioning step is carried out for at least 30 minutes, preferably for at least 60 minutes, preferably for at least 1.5 hours, at least 2 hours, at least 3 hours, at least 5 hours, at least 6 hours, at least 12 hours, at least 18 hours, preferably at least 24 hours, preferably for at least 36 hours or more preferably for at least 48 hours.

In another embodiment of the present invention, there is disclosed a method wherein the conditioning step includes exposing the micronized composite particles to a temperature in the range from 10° C. to 50° C., more preferably 24° C. to 50° C.

In another embodiment of the present invention, there is disclosed a method wherein the conditioning step takes place by distributing the micronized composite particles on a surface, optionally wherein the conditioning step takes place on a tray.

In another embodiment of the present invention, there is disclosed a method wherein the conditioning step involves exposing the micronized composite particles to the humidity for sufficient time for amorphous glycopyrrolate to re-crystallise after co-jet milling, as determined by Dynamic Vapour Sorption (DVS).

In another embodiment of the present invention, there is disclosed a method wherein the conditioning step involves powder agitation, optionally wherein the agitation is intermittent powder agitation, wherein powder agitation takes place within 30 minutes of completing the milling, within 25 minutes, within 20 minutes, within 15 minutes, preferably within 10 minutes, more preferably within 5 minutes, most preferably immediately after completing the milling of the glycopyrrolate and magnesium stearate.

In another embodiment of the present invention, there is disclosed a method wherein the milling gas has a humidity preferably below 15% RH, preferably below 10% RH, preferably below 5% RH, more preferably below 2.5% RH.

In another embodiment of the present invention, there is disclosed a method wherein the milling gas is preferably air, nitrogen or helium or combination thereof.

In another embodiment of the present invention, there is disclosed a method wherein the co-jet milling is carried out at an averaged powder feed rate of between 0.1 and 50 g/min, preferably at a feed rate of between 0.5 and 40 g/min, preferably at a feed rate of between 1 and 30 g/min, preferably at a feed rate of between 1.5 and 25 g/min, preferably at a feed rate of between 0.1 and 20 g/min, preferably at a feed rate of between 0.5 and 15 g/min, preferably at a feed rate of between 1 and 10 g/min, preferably at a feed rate of between 1.5 and 5 g/min.

In another embodiment of the present invention, there is disclosed a method wherein the formulation further comprises a beta-2 adrenoceptor agonist, preferably wherein the beta-2 adrenoceptor agonist is albuterol (salbutamol), metaproterenol, terbutaline, salmeterol fenoterol, procaterol, preferably, formoterol, carmoterol and pharmaceutically acceptable salts thereof, more preferably wherein the beta-2 adrenoceptor agonist is (R)-5-[2-(5,6-diethyl-indan-2-ylamino)-1-hydroxy-ethyl]-8-hydroxy-1H-quinolin-2-one maleate.

In another embodiment of the present invention, there is disclosed a formulation according to any preceding embodiment for use in treatment of a respiratory condition.

FIGURES

Figure 3:
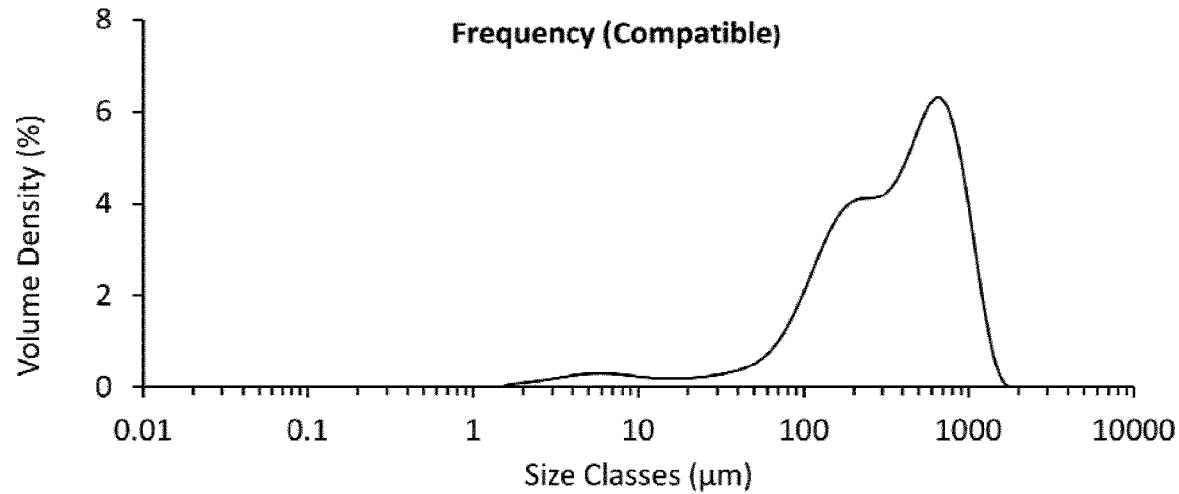

FIG. 3 shows the particle size distribution for jet milled glycopyrrolate without magnesium stearate which has been tipped out as a compact heap of powder and the heap of powder was exposed to 40° C. at 75% RH for 1 hour on a tray thereby preventing the conditioning environment from reaching the internal particles in the heap of powder. The cumulative fraction under 5 µm was 1.44%.

Figure 4:
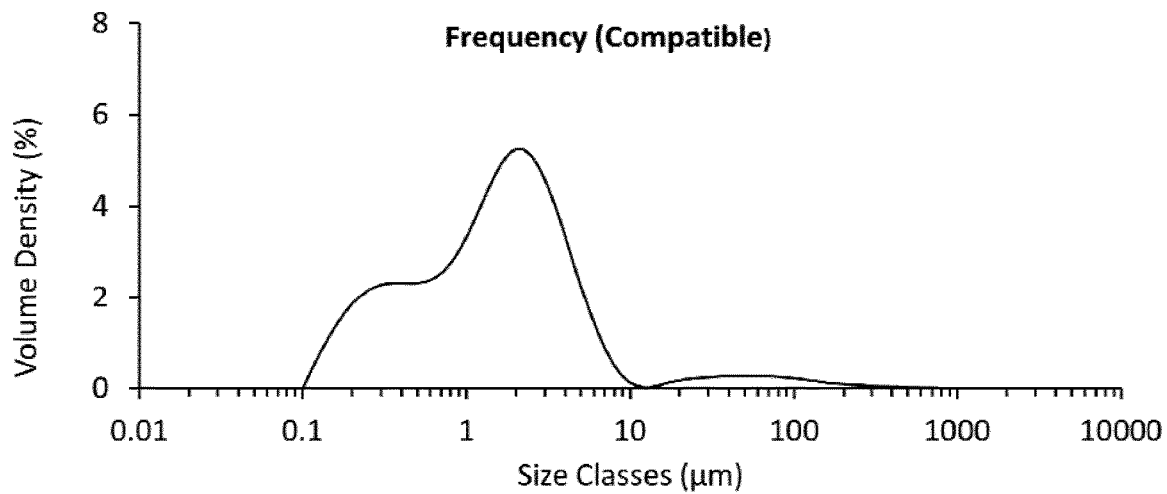

FIG. 4 shows the particle size distribution for Formulation 1, jet milled glycopyrrolate only; t=0 hours.

Figure 5:
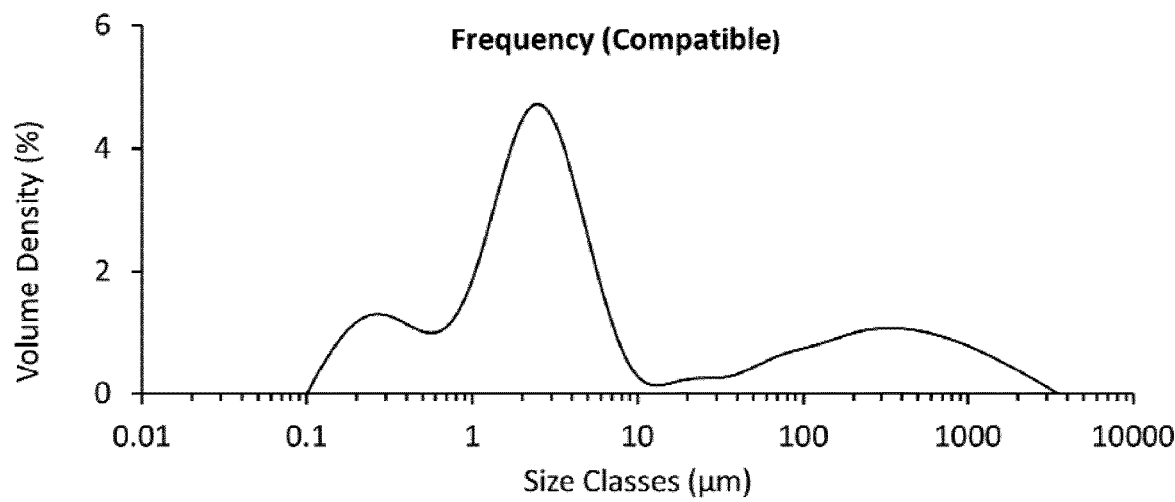

FIG. 5 shows the particle size distribution for Formulation 1, jet milled glycopyrrolate only; Conditioned at 25° C. at 60% RH for 49 hours, analysed 72 hours after micronisation.

Figure 6:
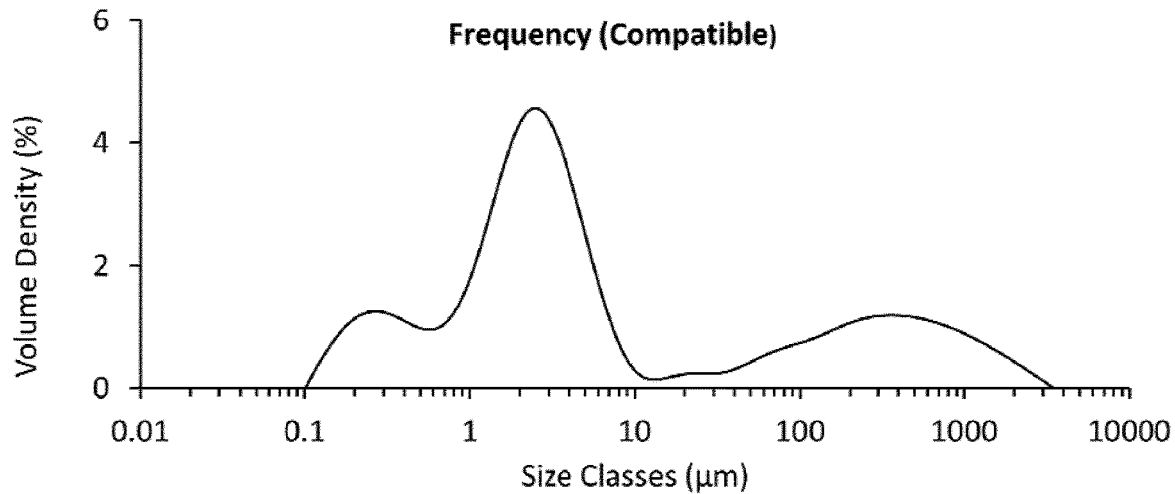

FIG. 6 shows the particle size distribution for Formulation 1, jet milled Glycopyrrolate only; Conditioned at 25° C. at 60% RH for 52 hours, analysed 72 hours after micronisation, the cumulative fraction under 5 µm was 62.22%.

Figure 7:
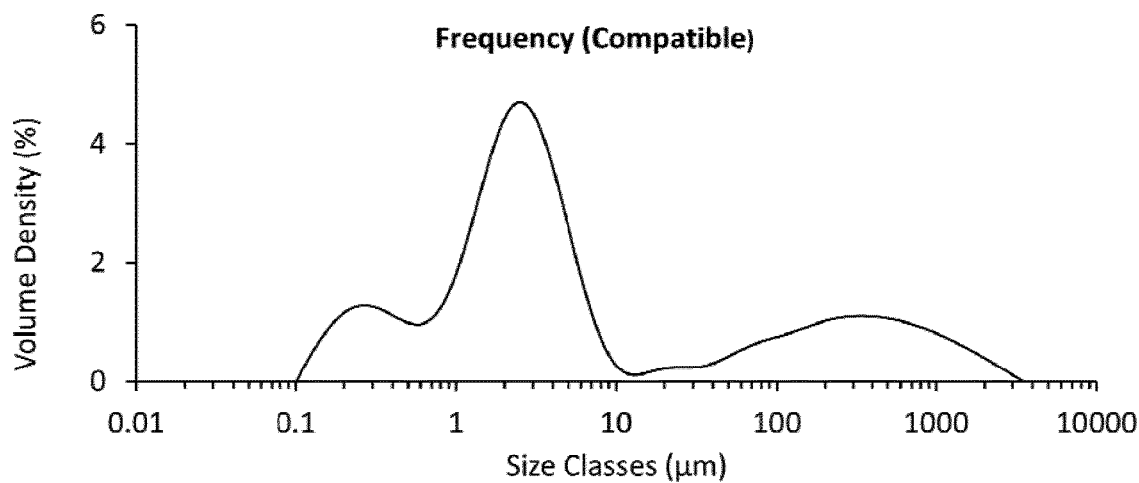

FIG. 7 shows the particle size distribution for Formulation 1, jet milled Glycopyrrolate only; Conditioned at 25° C. at 60% RH for 71 hours, analysed 72 hours after micronisation, the cumulative fraction under 5 µm was 63.69%.

Figure 8:
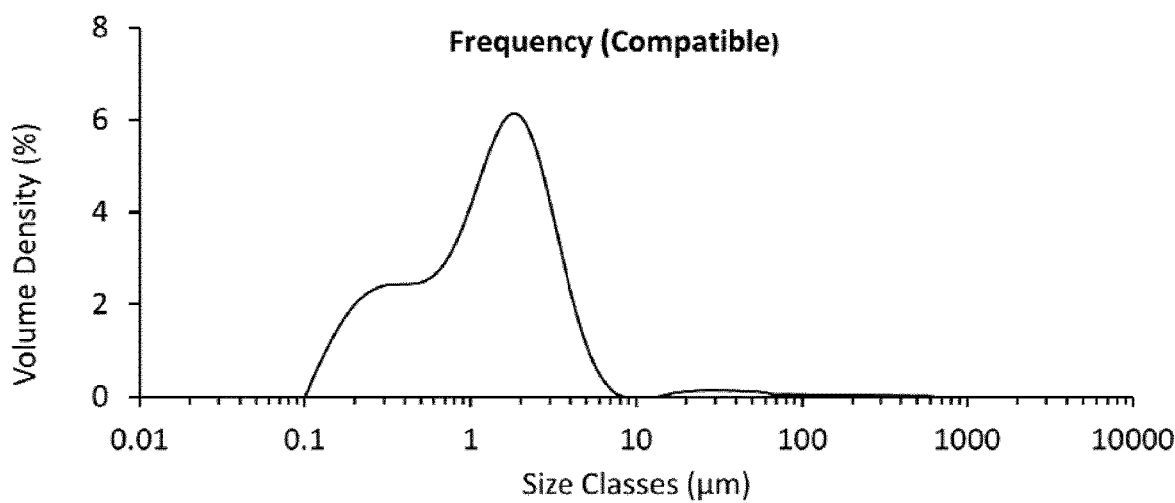

FIG. 8 shows the particle size distribution for Formulation 2, co-jet milled glycopyrrolate and magnesium stearate, t=0 hours.

Figure 9:
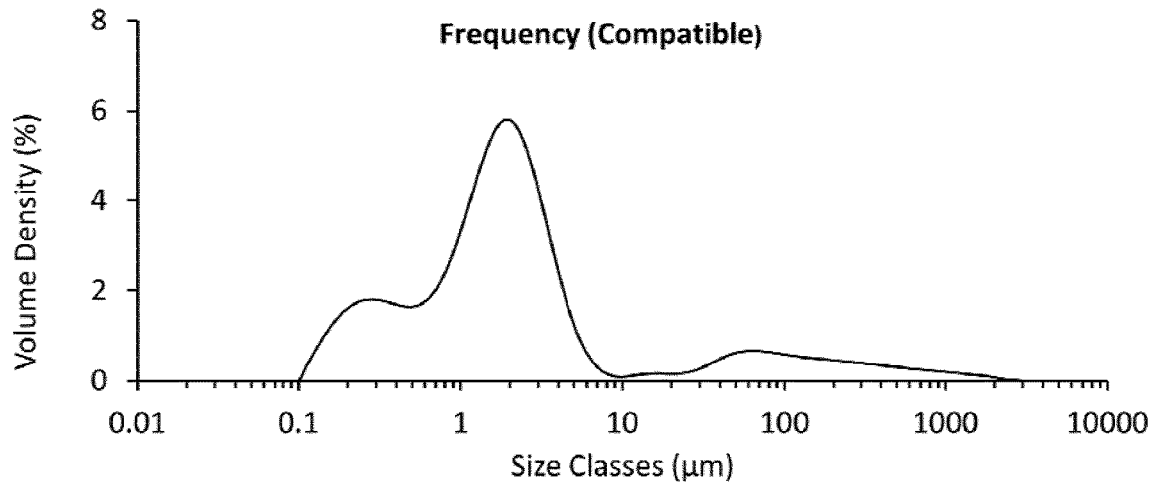

FIG. 9 shows the particle size distribution for Formulation 2, co-jet milled glycopyrrolate and magnesium stearate; conditioned at 25° C. at 60% RH for 49 hours, analysed 72 hours after co-micronisation.

Figure 10:
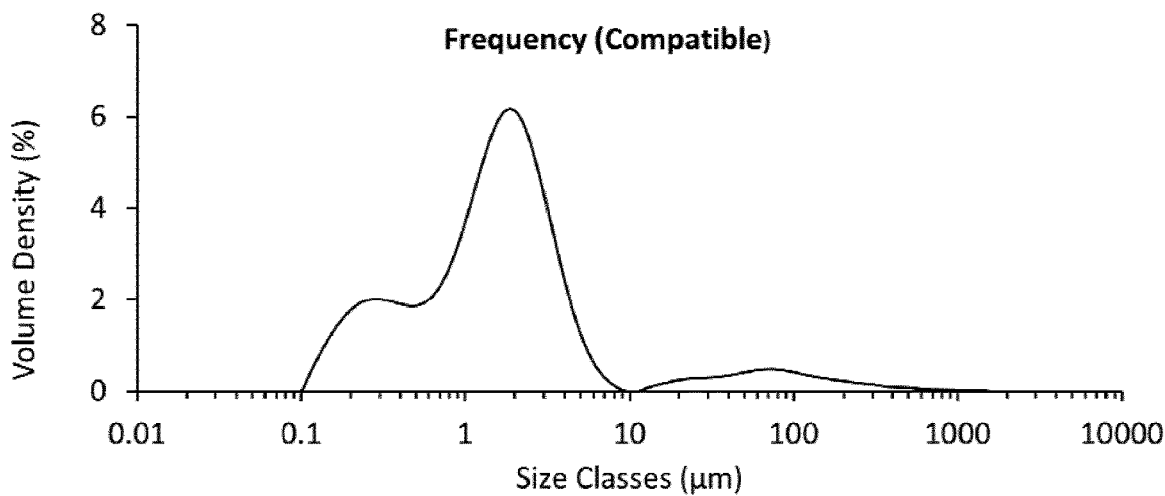

FIG. 10 shows the particle size distribution for Formulation 2, co-jet milled glycopyrrolate and magnesium stearate; conditioned at 25° C. at 60% RH for 52 hours, analysed 72 hours after co-micronisation, the cumulative fraction under 5 µm was 88.66%.

Figure 11:
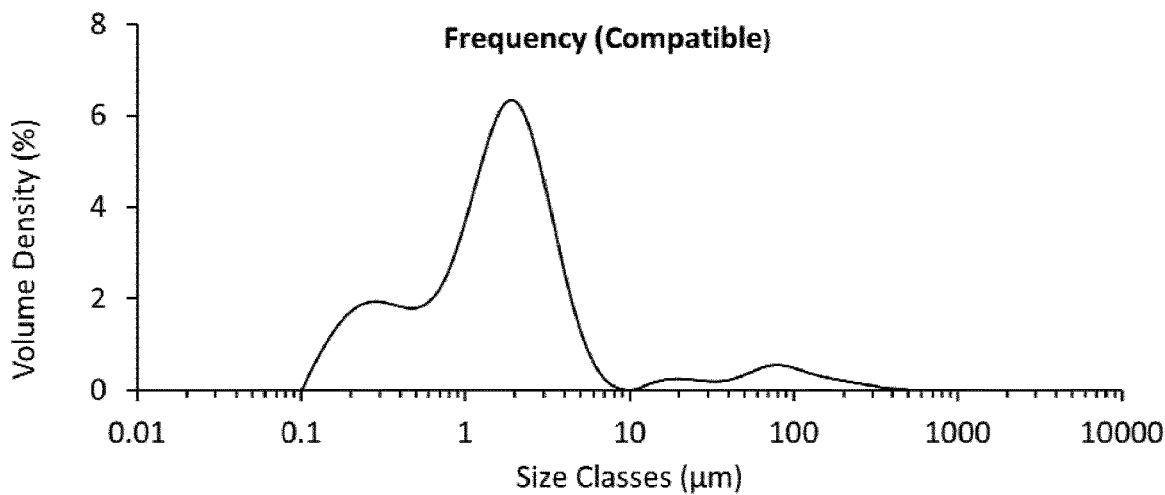

FIG. 11 shows the particle size distribution for Formulation 2, co-jet milled glycopyrrolate and magnesium stearate; conditioned at 25° C. at 60% RH for 71 hours, analysed 72 hours after co-micronisation, the cumulative fraction under 5 µm was 89.54%.

Figure 12:
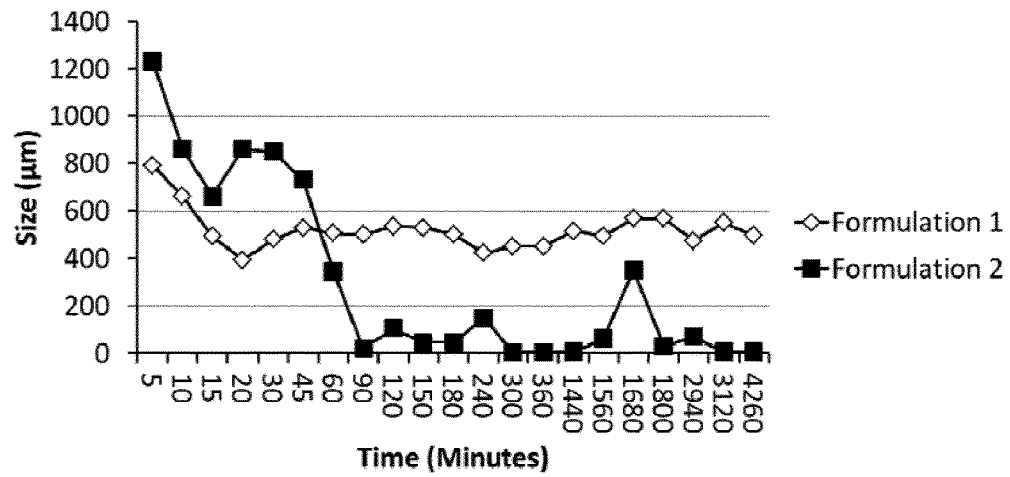

FIG. 12 shows a comparison of the 0 90 values for Formulation 1 and Formulation 2 conditioned for 5 minutes until 71 hours, all the samples were analysed at 72 hours.

Figure 13:
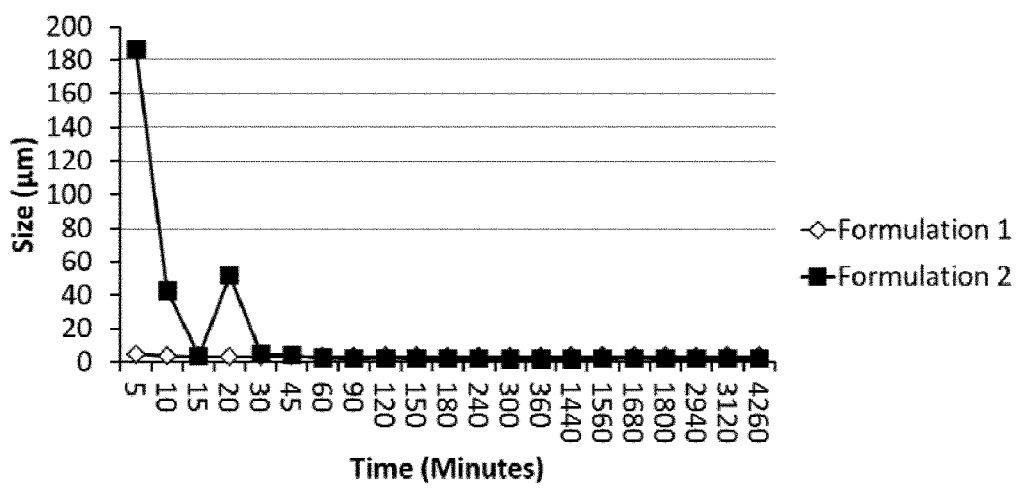

FIG. 13 shows a comparison of the 0 50 values for Formulation 1 and Formulation 2 conditioned for 5 minutes until 71 hours, all the samples were analysed at 72 hours.

Figure 14:
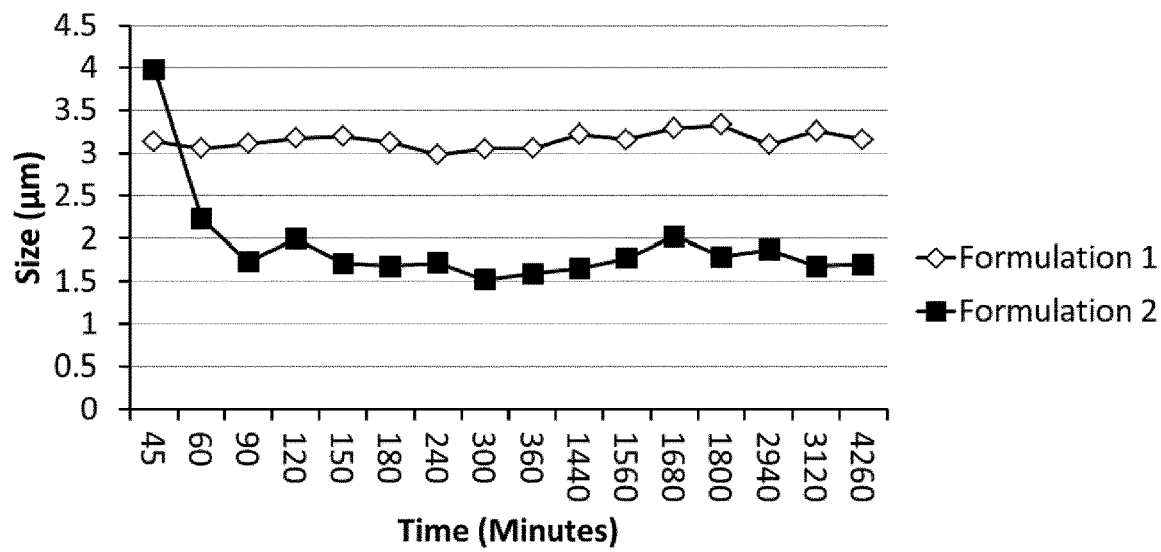

FIG. 14 shows a comparison of the 0 50 values for Formulation 1 and Formulation 2 conditioned for 5 minutes until 72 hours wherein the x-axis shows values from 45 minutes until 71 hours, all the samples were analysed at 72 hours.

Figure 15:
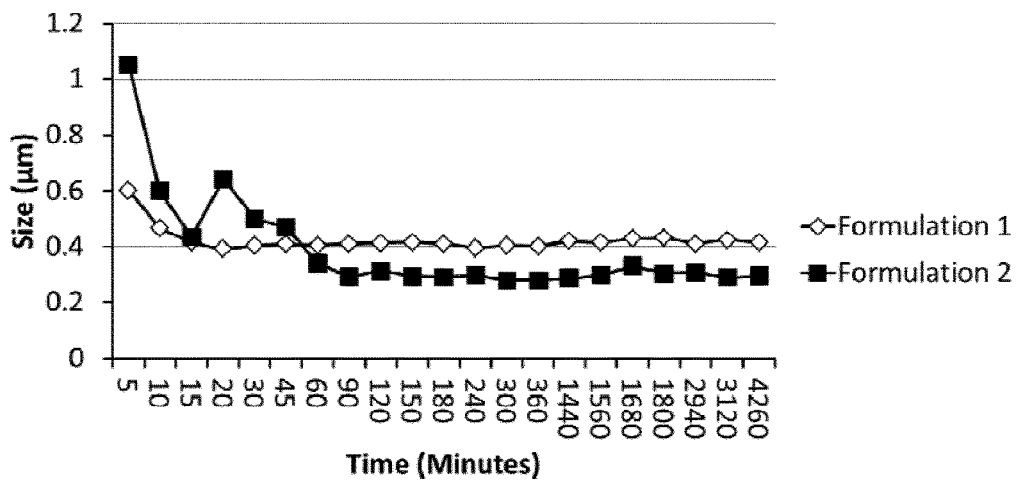

FIG. 15 shows a comparison of the 0 10 values for Formulation 1 and Formulation 2 conditioned for 5 minutes until 71 hours, all the samples were analysed at 72 hours.

Figure 16:
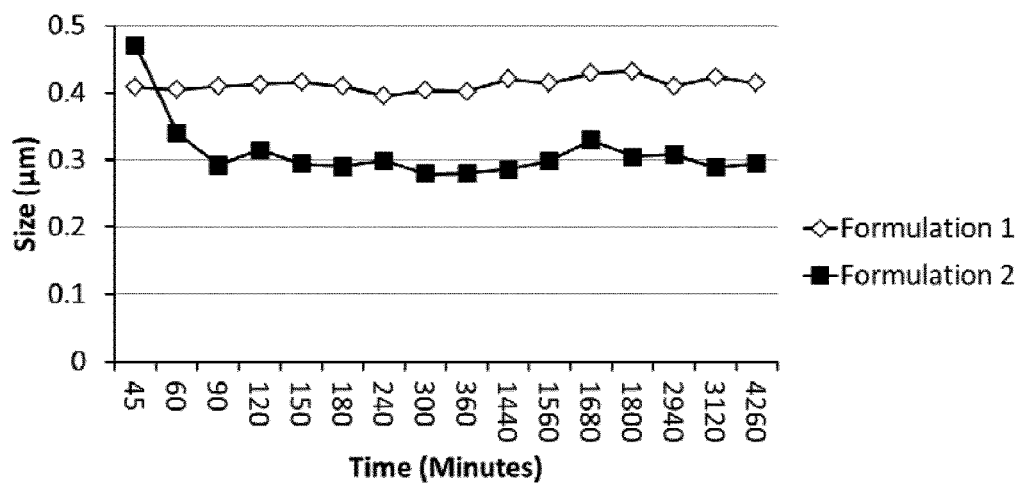

FIG. 16 shows a comparison of the 0 10 values for Formulation 1 and Formulation 2 conditioned for 5 minutes until 71 hours, all the samples were analysed at 72 hours wherein the x-axis shows values from 45 minutes until 72 hours.

Figure 17:
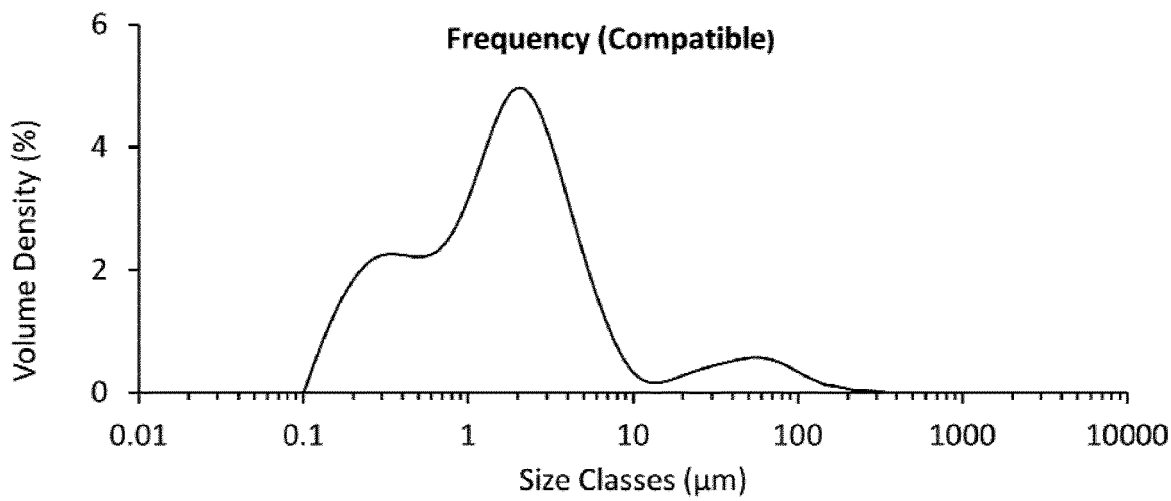

FIG. 17 shows the particle size distribution for Formulation 3, jet milled glycopyrrolate only, t=0 hours.

Figure 18:
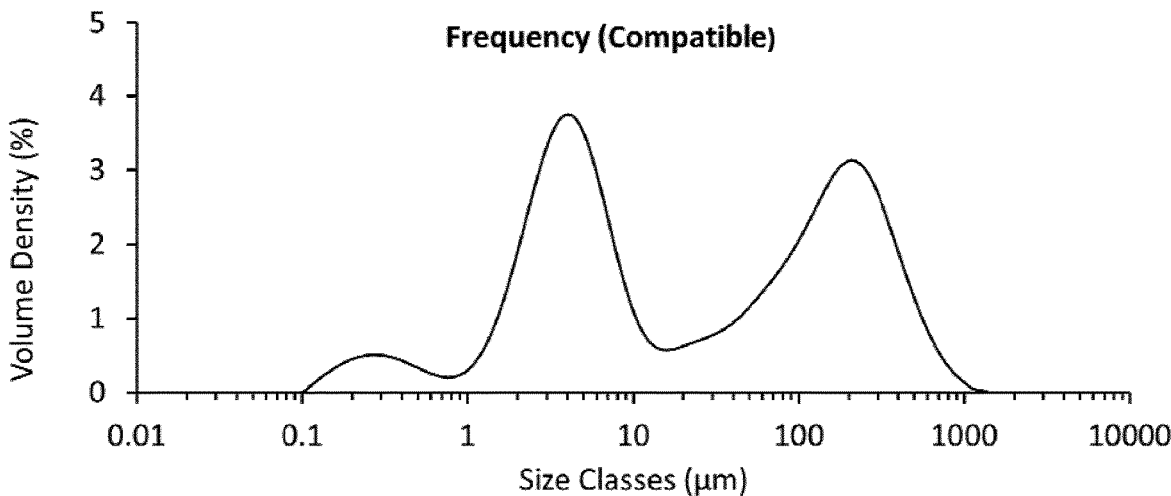

FIG. 18 shows the particle size distribution for Formulation 3, jet milled glycopyrrolate only; conditioned at 50° C. at 50% RH for 49 hours, analysed 49 hours after co-micronisation.

Figure 19:
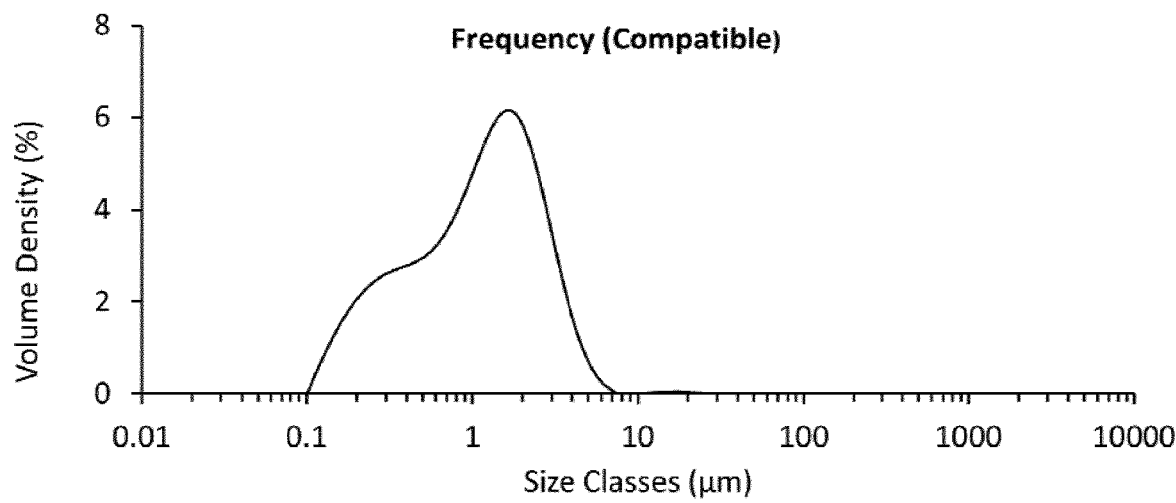

FIG. 19 shows the particle size distribution for Formulation 4, co-jet milled glycopyrrolate and magnesium stearate, t=0 hours.

Figure 20:
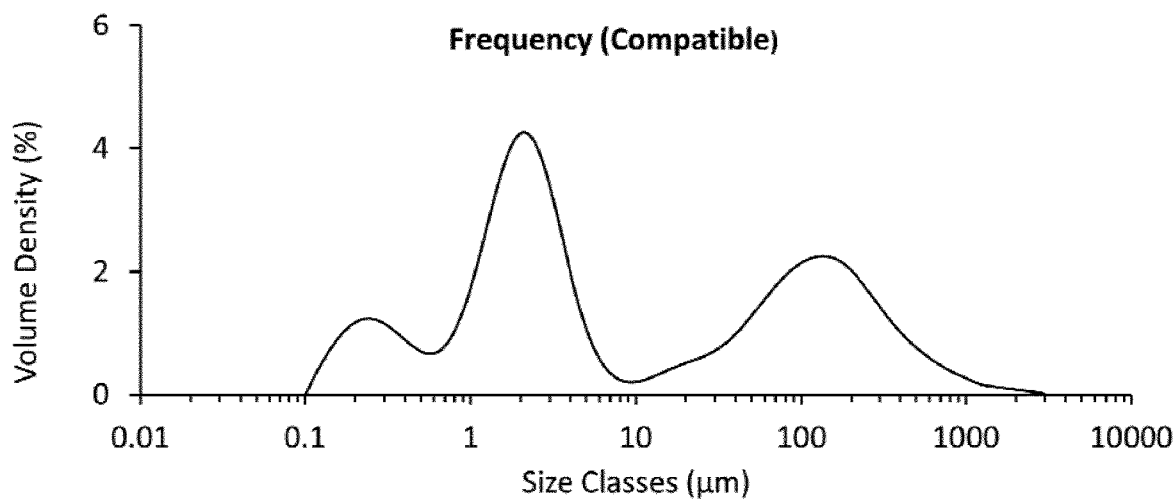

FIG. 20 shows the particle size distribution for Formulation 4, co-jet milled glycopyrrolate and magnesium stearate; Conditioned at 50° C. at 50% RH for 49 hours, analysed 49 hours after co-micronisation.

Figure 21:
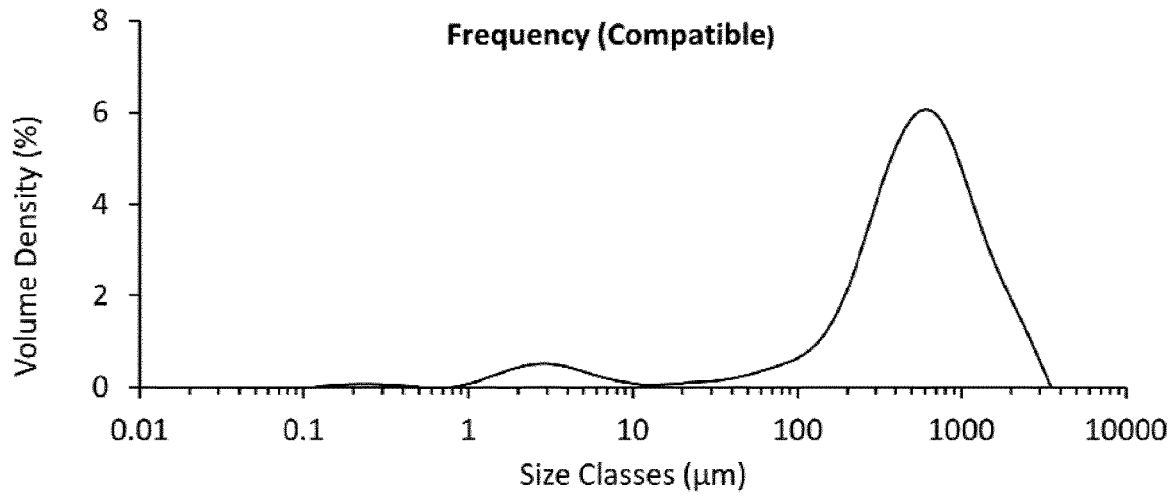

FIG. 21 shows the particle size distribution for Formulation 5, jet milled glycopyrrolate only.

Figure 22:
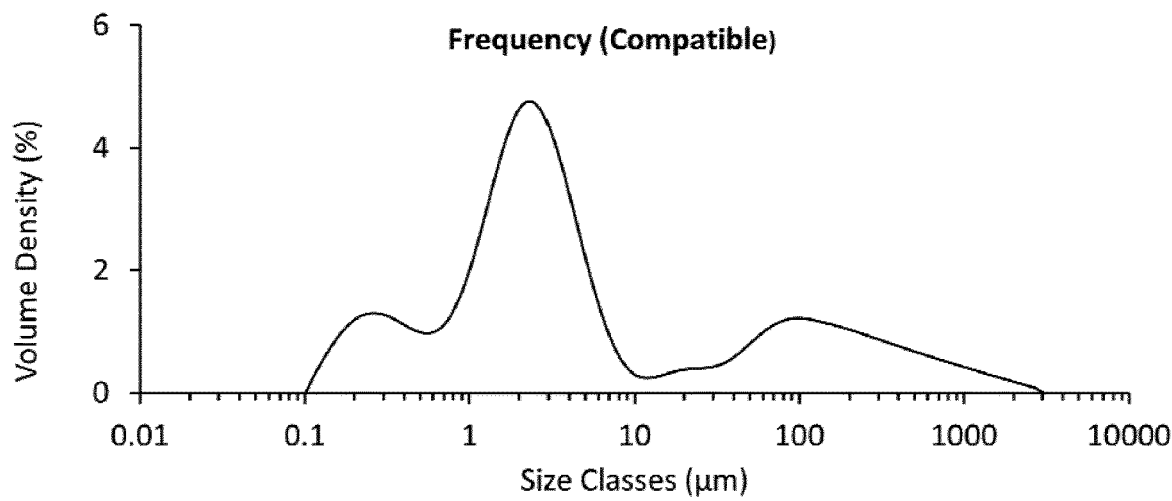

FIG. 22 shows the particle size distribution for Formulation 5, jet milled glycopyrrolate only; Conditioned at 6° C. at 86% RH for 49 hours, analysed 49 hours after micronisation.

Figure 23:
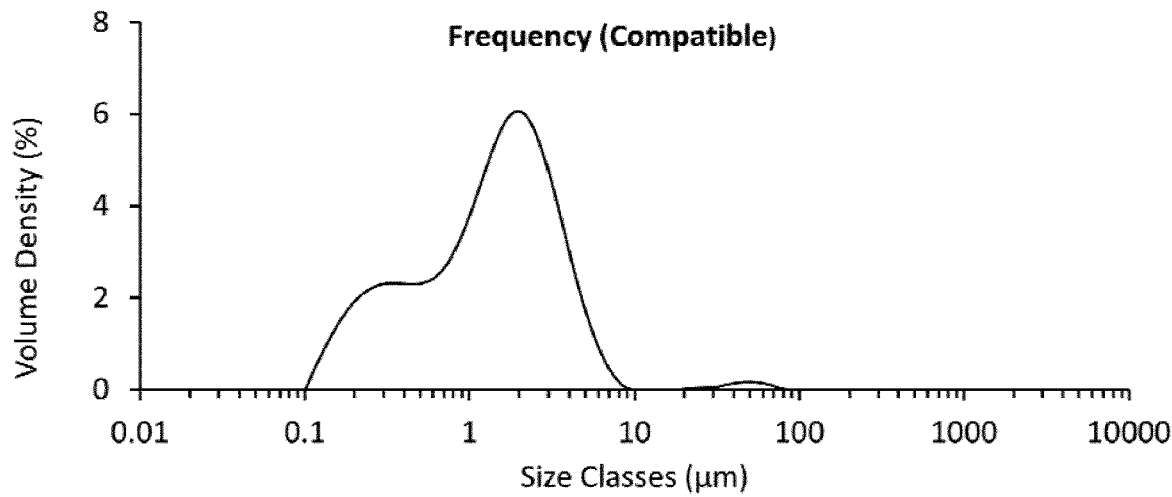

FIG. 23 shows the particle size distribution for Formulation 6, co-jet milled glycopyrrolate and magnesium stearate, t=0 hours.

Figure 24:
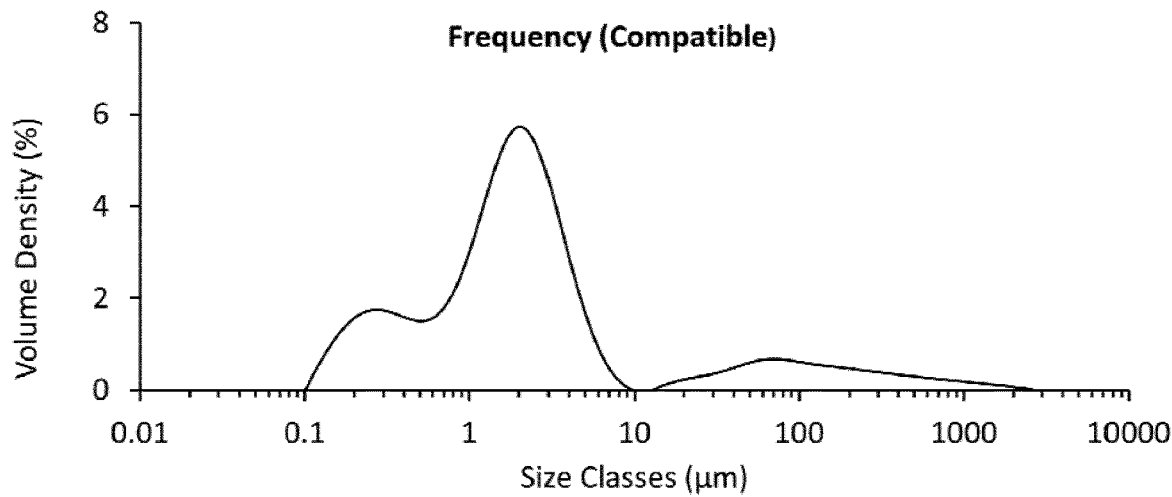

FIG. 24 shows the particle size distribution for Formulation 6, co-jet milled glycopyrrolate and magnesium stearate; Conditioned at 6° C. at 86% RH for 49 hours, analysed 49 hours after co-micronisation.

Figure 25:
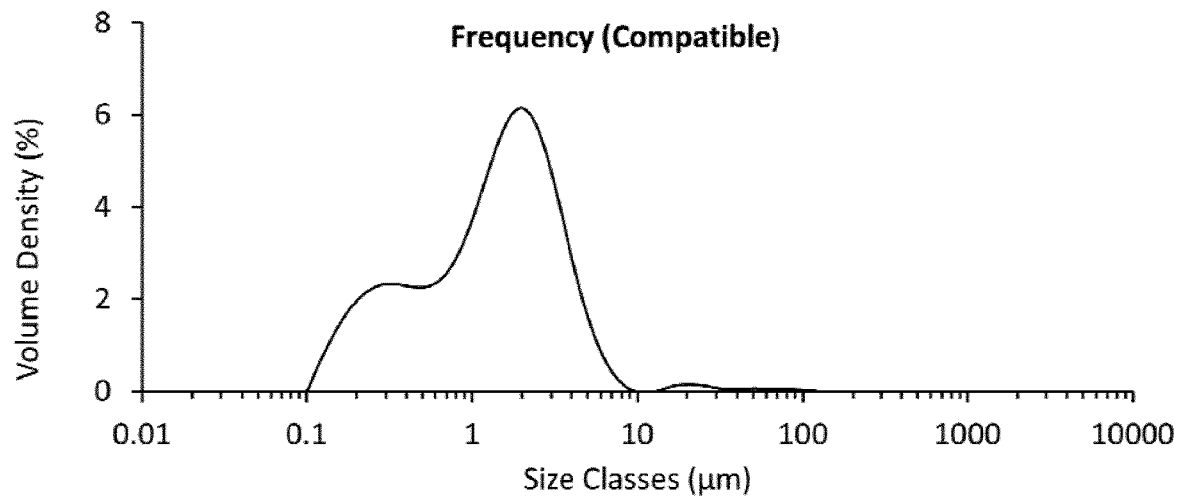

FIG. 25 shows the particle size distribution for Formulation 7, co-jet milled glycopyrrolate and magnesium stearate; conditioned at 24° C. at 45% RH on a tray for 72 hours, analysed 72 hours after co-micronisation.

Figure 26:
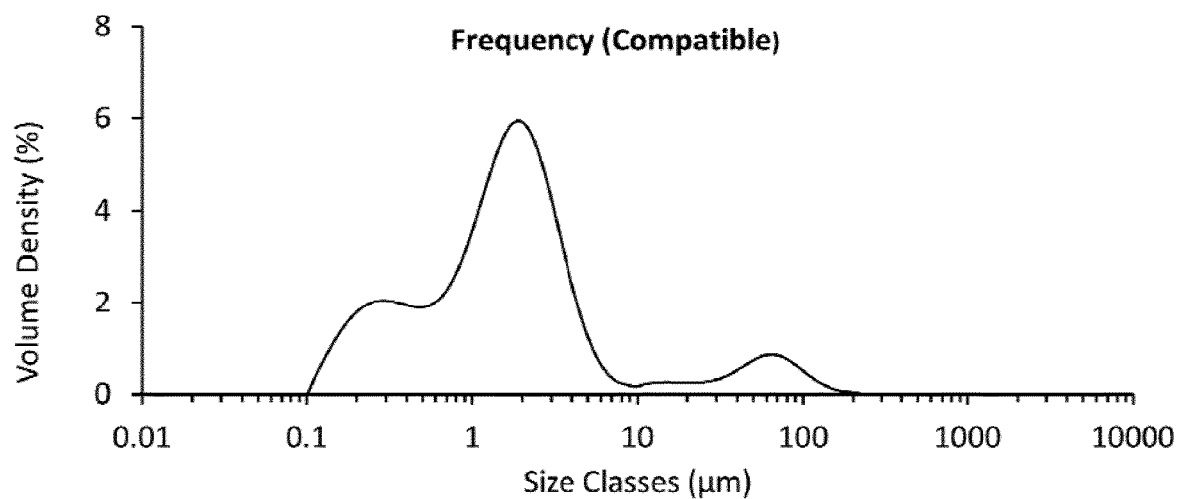

FIG. 26 shows the particle size distribution for Formulation 8, co-jet milled glycopyrrolate and magnesium stearate; Conditioned at 24° C. at 45% RH in an open glass vial for 144 hours, analysed 144 hours after co-micronisation.

FIG. 27 shows the DVS trace for Formulation 1, jet milled glycopyrrolate only, analysis commenced immediately after jet milling. The presence of multiple peaks is a reliable indicator of the presence of amorphous material.

FIG. 28 shows the DVS trace for Formulation 1, jet milled glycopyrrolate only, conditioned at 25° C. at 60% RH for 49 hours, analysis commenced 49 hours after jet milling. The absence of multiple peaks is a reliable indicator of the absence of amorphous material.

FIG. 29 shows the DVS trace for Formulation 2, co-jet milled glycopyrrolate and magnesium stearate, analysis commenced immediately after co-jet milling.

FIG. 30 shows the DVS trace for Formulation 2, co-jet milled glycopyrrolate and magnesium stearate conditioned at 25° C. at 60% RH for 49 hours, analysis commenced 49 hours after co-jet milling.

FIG. 31 shows the DVS trace for Formulation 4, co-jet milled glycopyrrolate and magnesium stearate conditioned at 50° C. at 50% RH for 49 hours, analysis commenced 49 hours after co-jet milling.

FIG. 32 shows the DVS trace for Formulation 5, jet milled glycopyrrolate only, conditioned at 6° C. at 86% RH for 49 hours, analysis commenced 49 hours after jet milling.

FIG. 33 shows the DVS trace for Formulation 6, co-jet milled glycopyrrolate and magnesium stearate conditioned at 6° C. at 86% RH for 49 hours, analysis commenced 49 hours after co-jet milling.

FIG. 34 shows the DVS trace for Formulation 7, co-jet milled glycopyrrolate and magnesium stearate conditioned 24° C.±3° C. at 45% RH±5% RH for 72 hrs, analysis commenced 72 hours after co-jet milling.

FIG. 35 shows the DVS trace for Formulation 8, co-jet milled glycopyrrolate and magnesium stearate, analysis commenced immediately after co-jet milling.

FIG. 36 shows the DVS trace for Formulation 8, co-jet milled glycopyrrolate and magnesium stearate conditioned at 24° C.±3° C. at 45% RH±5% RH for 144 hours and the analysed at 144 hours after co-micronisation. The absence of multiple peaks is a reliable indicator of the absence of amorphous material.

Figure 37:
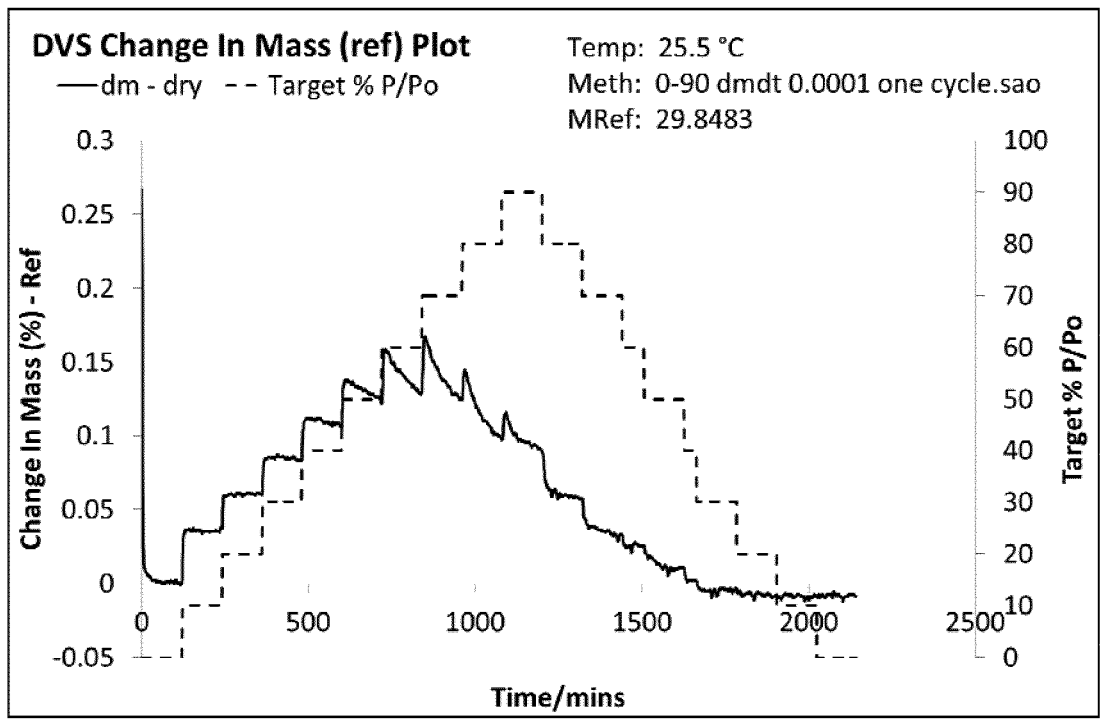

FIG. 37 shows the DVS trace for Formulation 13a, jet milled glycopyrrolate only using a milling gas having humidity <20% RH (2.8-3.5% RH) and the analysed immediately after micronisation.

Figure 38:
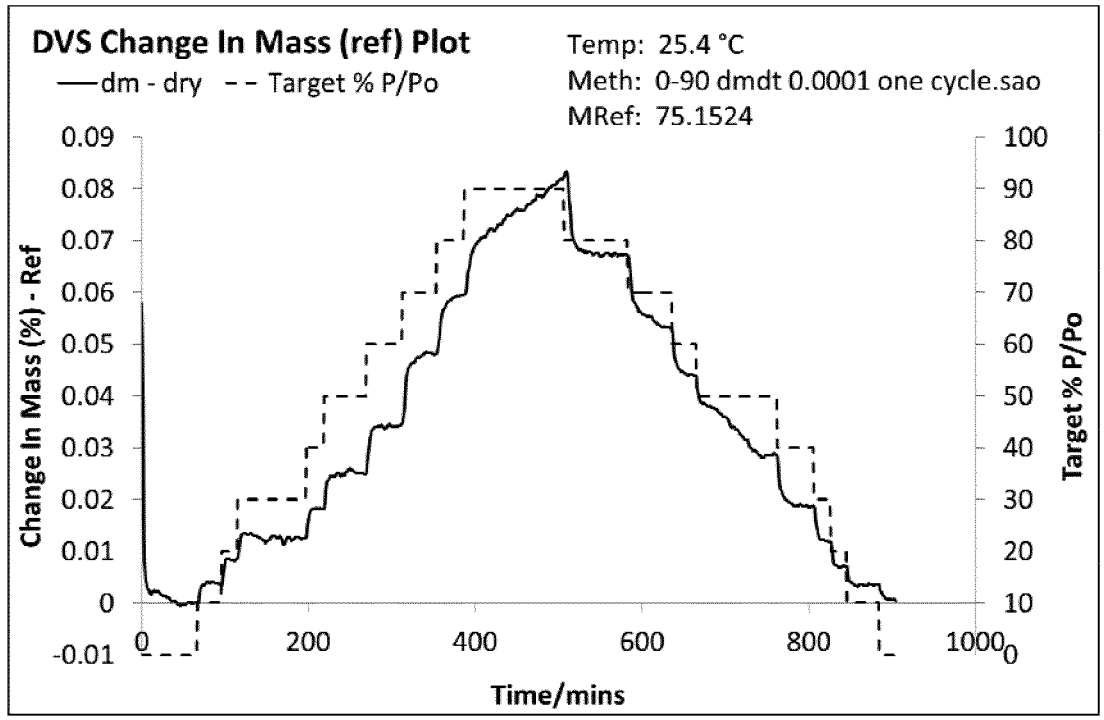

FIG. 38 shows the OVS trace for Formulation 13b, jet milled glycopyrrolate only using a milling gas having an elevated humidity (31.6-36.2% RH) and then analysed immediately after micronisation.

Figure 39:
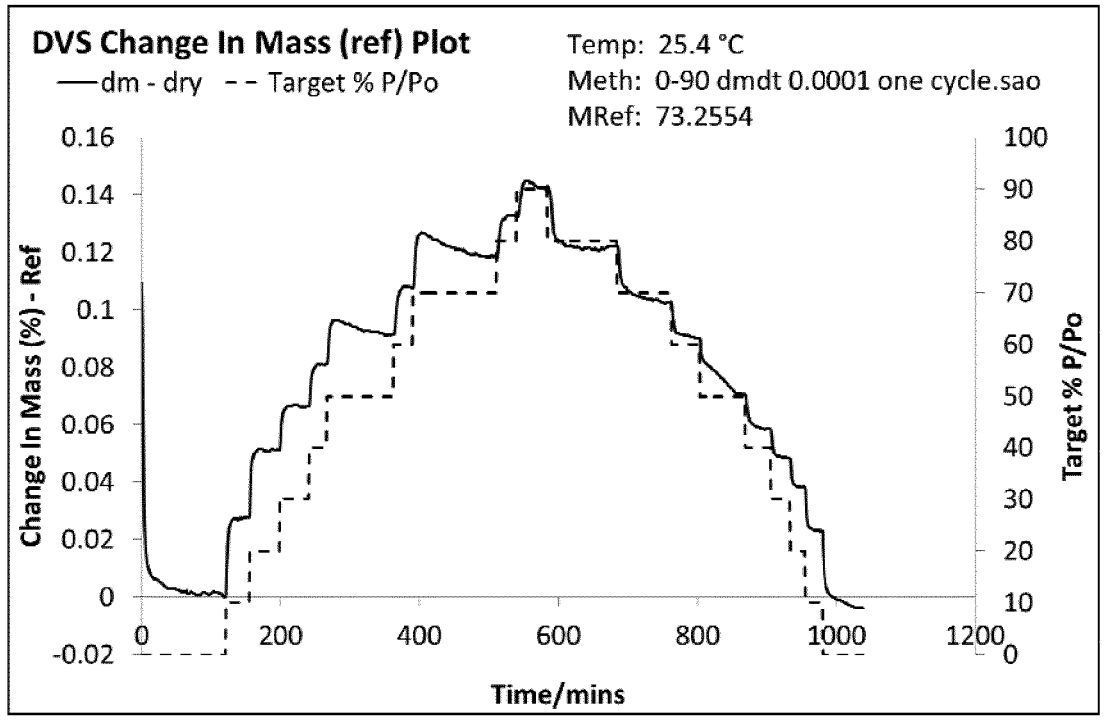

FIG. 39 shows the OVS trace for Formulation 13c, co-jet milled glycopyrrolate and magnesium stearate using a milling gas having an elevated humidity (32.4-37.1% RH) and then analysed immediately after co-micronisation.

Figure 40:
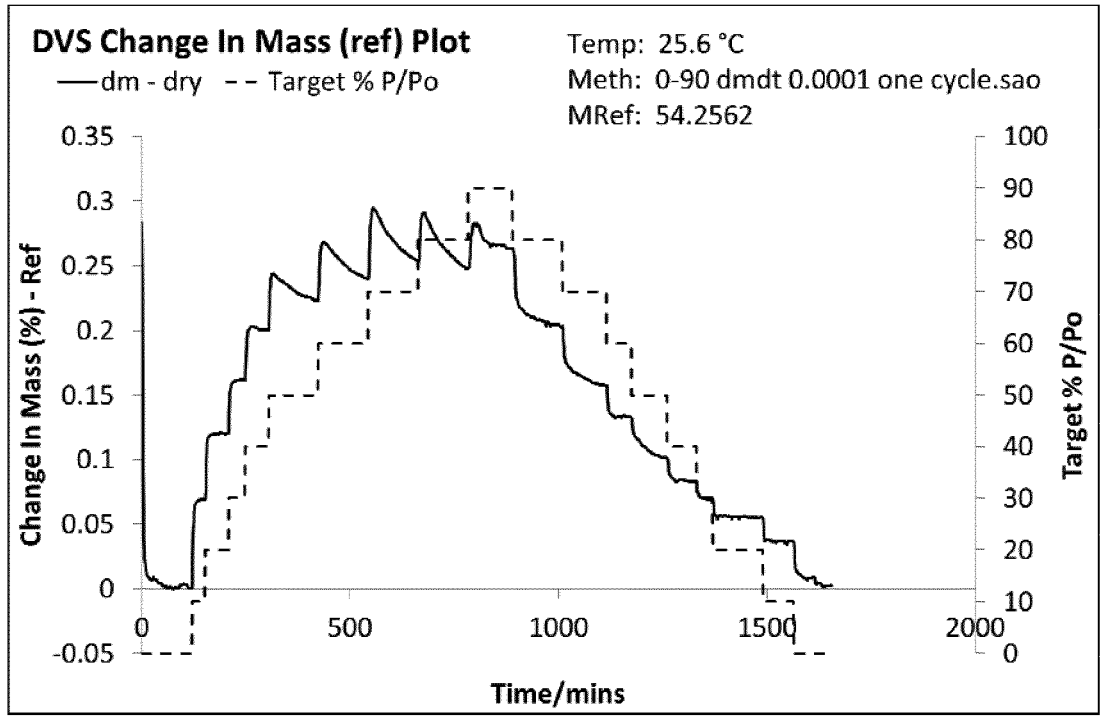

FIG. 40 shows the OVS trace for Formulation 13d, co-jet milled glycopyrrolate and magnesium stearate using a milling gas having humidity <20% RH (3.4-3.9% RH) and then analysed immediately after co-micronisation.

Figure 41:
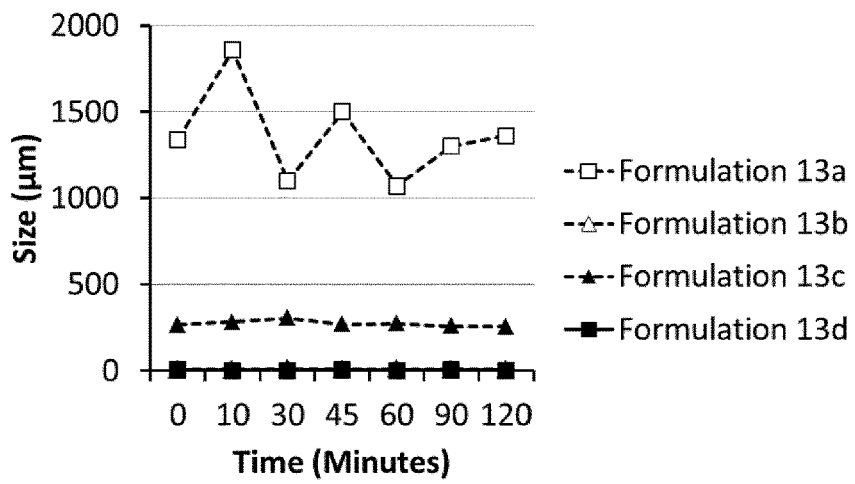

FIG. 41 shows a comparison of the 0 90 values for Formulations 13a-d analysed using the Malvern dry analysis method.

Figure 42:
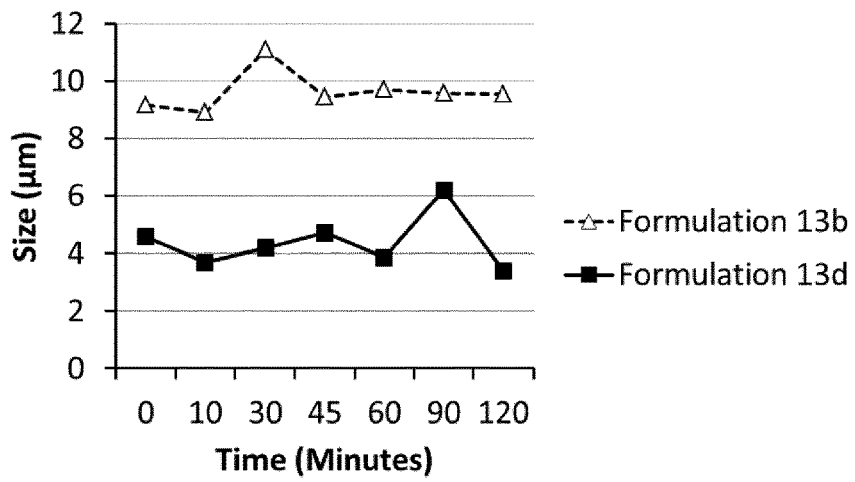

FIG. 42 shows a specific comparison of the 0 90 values for Formulation 13b and Formulation 13d analysed using the Malvern dry analysis method.

Figure 43:
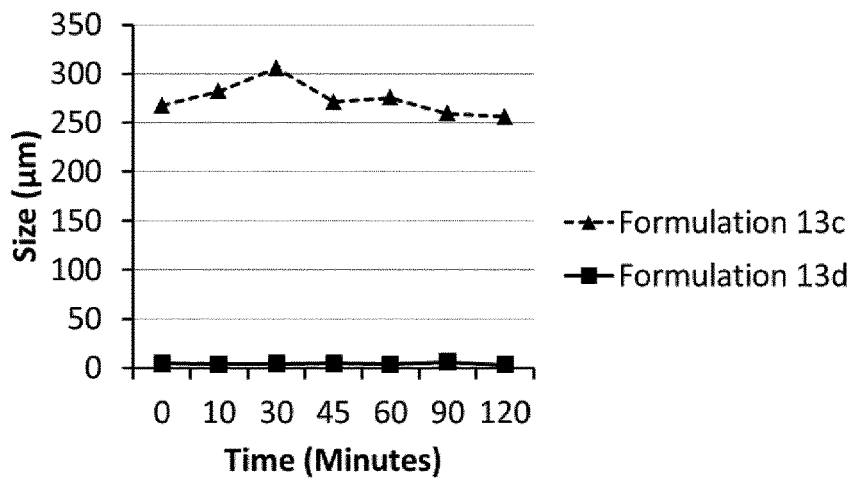

FIG. 43 shows a specific comparison of the 090 values for Formulation 13c and Formulation 13d analysed using the Malvern dry analysis method.

Figure 44:
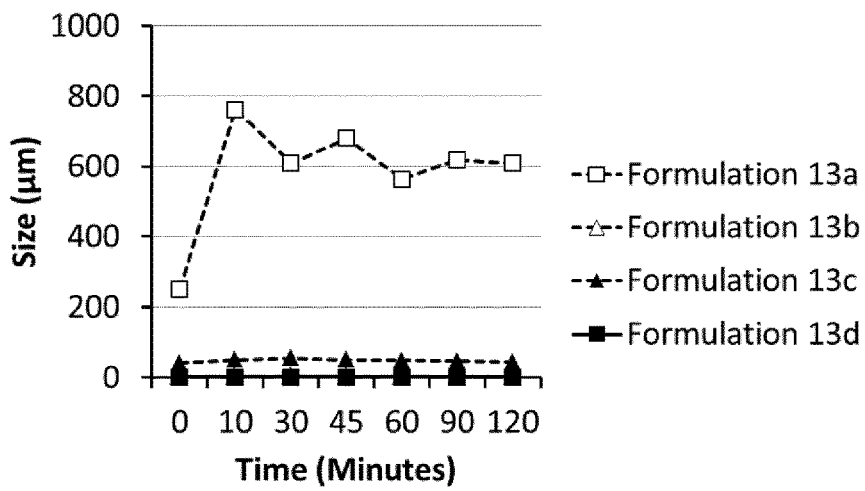

FIG. 44 shows a comparison of the 0 50 values for Formulations 13a-d analysed using the Malvern dry analysis method.

Figure 45:
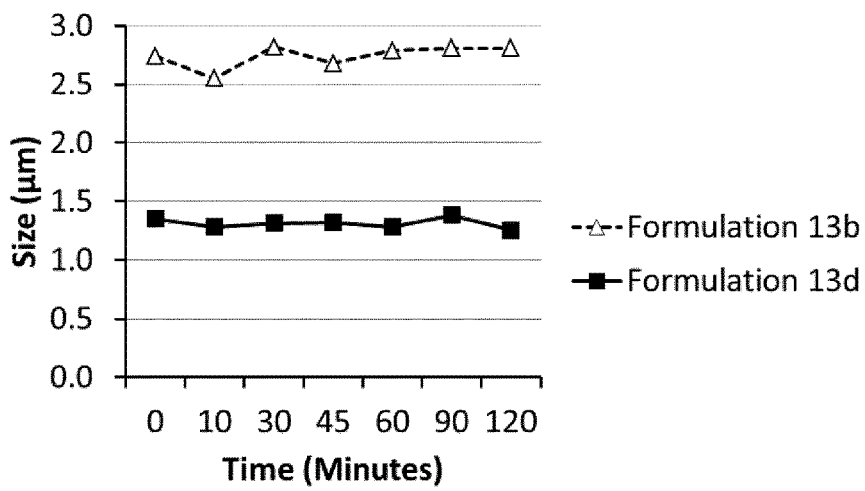

FIG. 45 shows a specific comparison of the 0 50 values for Formulation 13b and Formulation 13d analysed using the Malvern dry analysis method.

Figure 46:
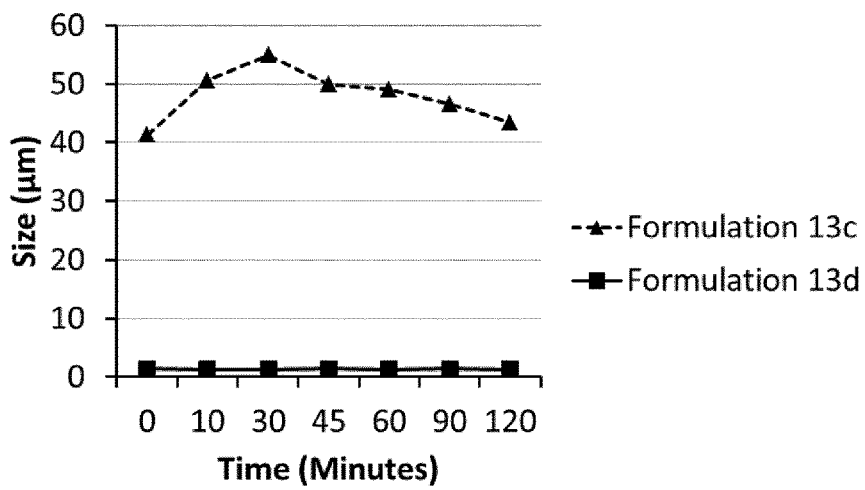

FIG. 46 shows a specific comparison of the 050 values for Formulation 13c and Formulation 13d analysed using the Malvern dry analysis method.

Figure 47:
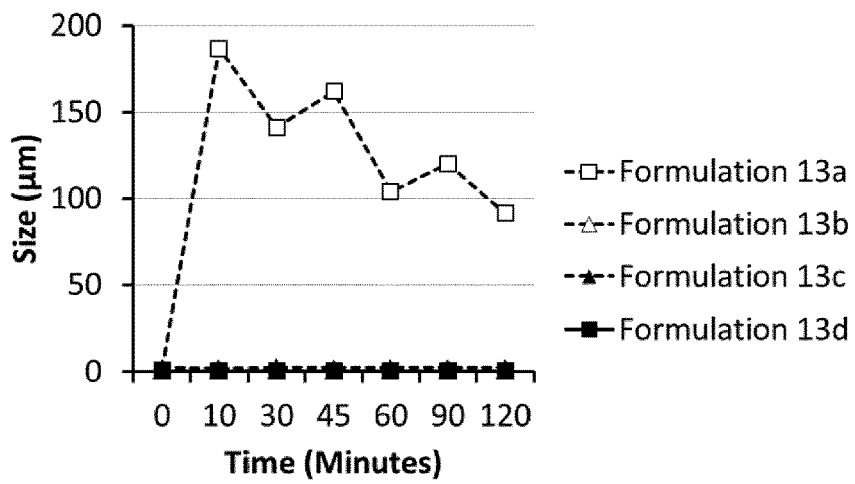

FIG. 47 shows a comparison of the 0 10 values for Formulations 13a-d analysed using the Malvern dry analysis method.

Figure 48:
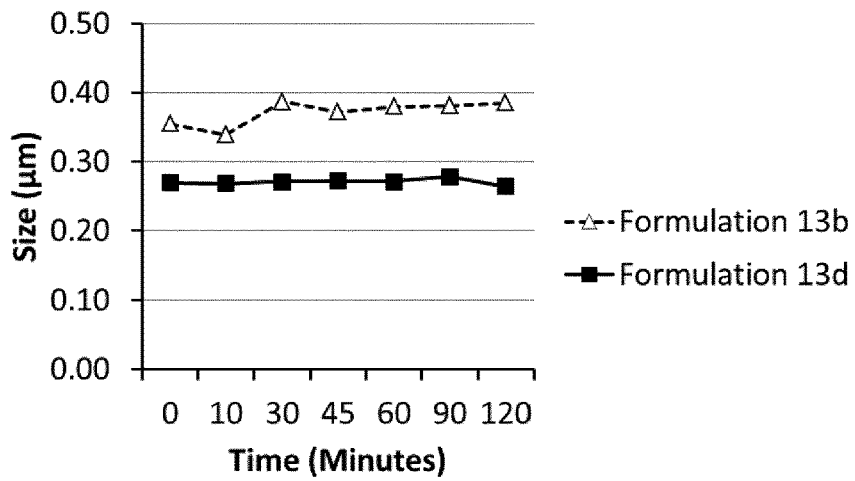

FIG. 48 shows a specific comparison of the 0 10 values for Formulation 13b and Formulation 13d analysed using the Malvern dry analysis method.

Figure 49:
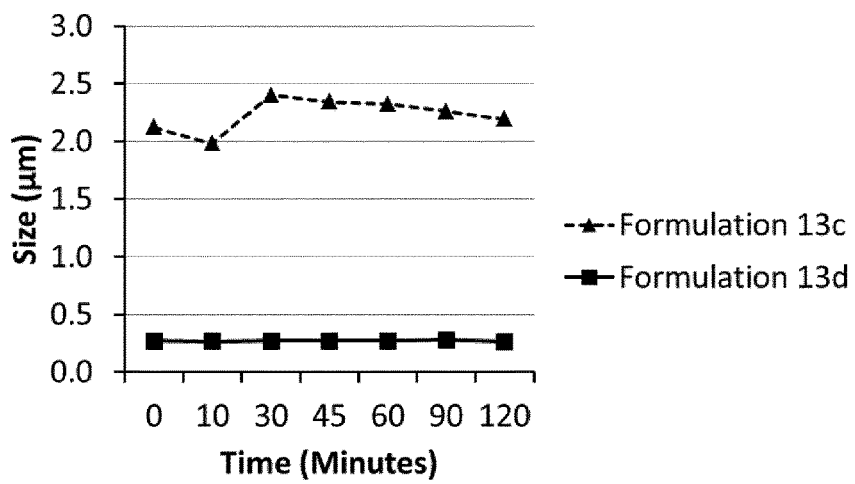

FIG. 49 shows a specific comparison of the 0 10 values for Formulation 13c and Formulation 13d analysed using the Malvern dry analysis method.

Figure 50:
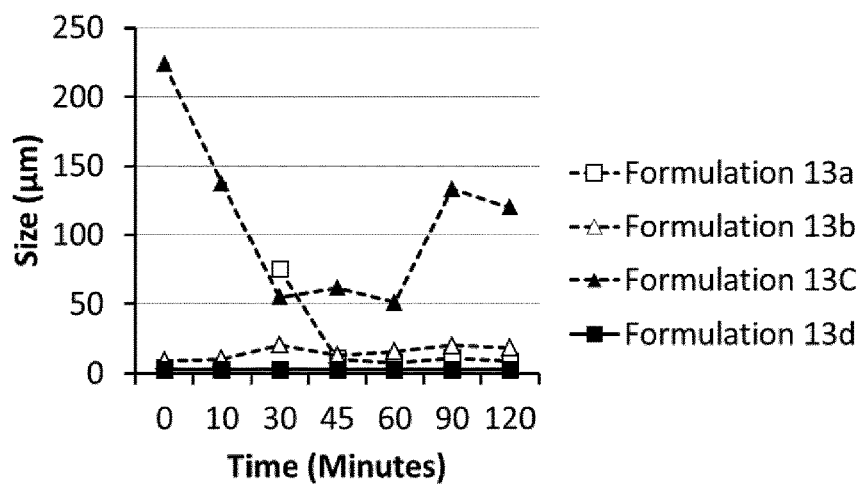

FIG. 50 shows a comparison of the 0 90 values for Formulations 13a-d analysed using the Malvern wet analysis method. Operator error resulted in the loss of the 10 minute sample for Formulation 13a.

Figure 51:
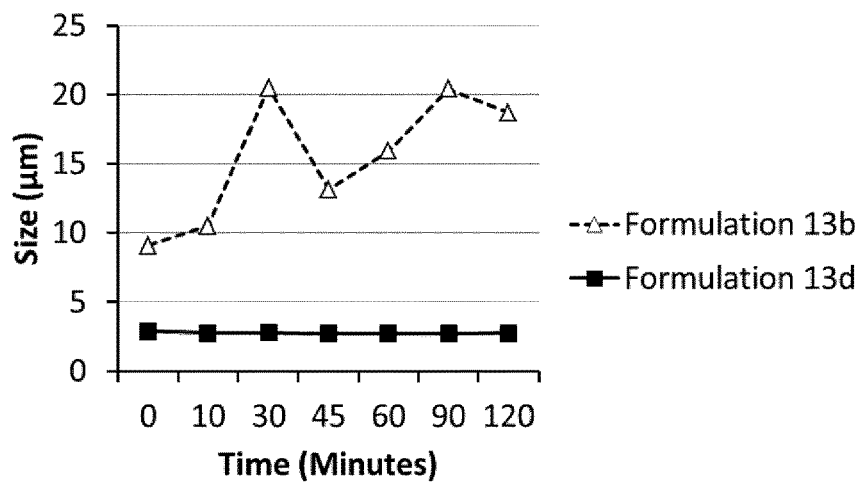

FIG. 51 shows a specific comparison of the 0 90 values for Formulation 13b and Formulation 13d analysed using the Malvern wet analysis method.

Figure 52:
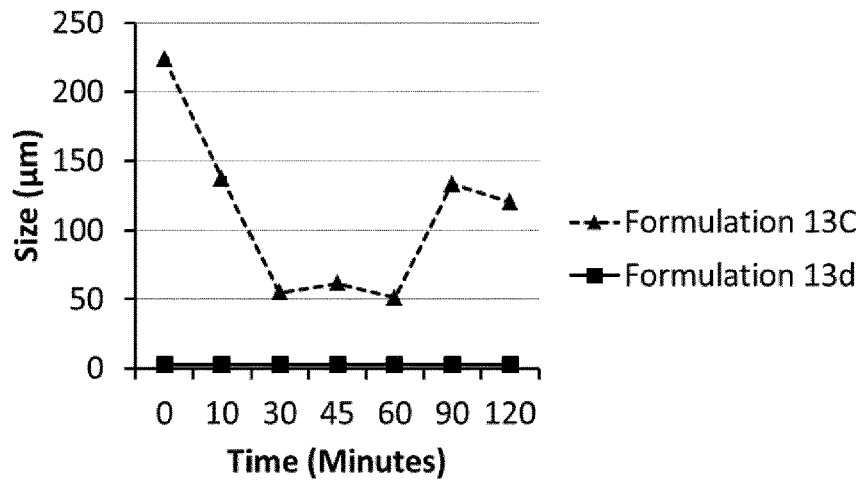

FIG. 52 shows a specific comparison of the 090 values for Formulation 13c and Formulation 13d analysed using the Malvern wet analysis method.

Figure 53:
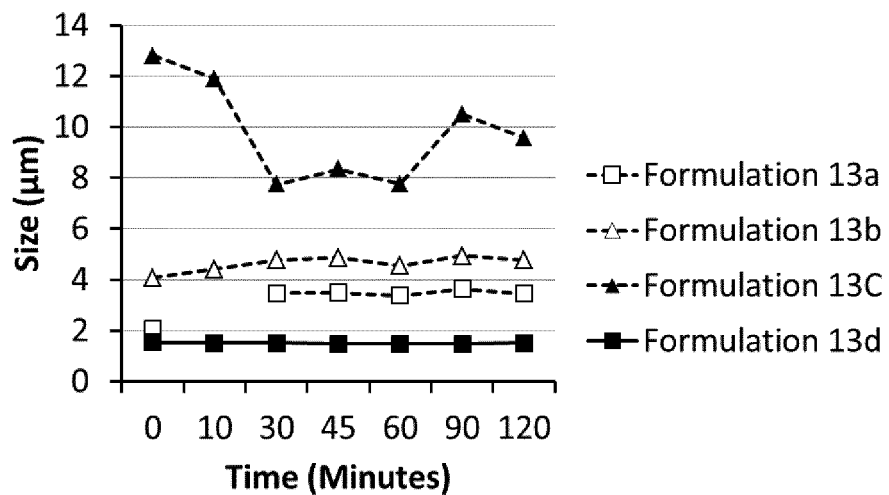

FIG. 53 shows a comparison of the 0 50 values for Formulations 13a-d analysed using the Malvern wet analysis method. Operator error resulted in the loss of the 10 minute sample for Formulation 13a.

Figure 54:
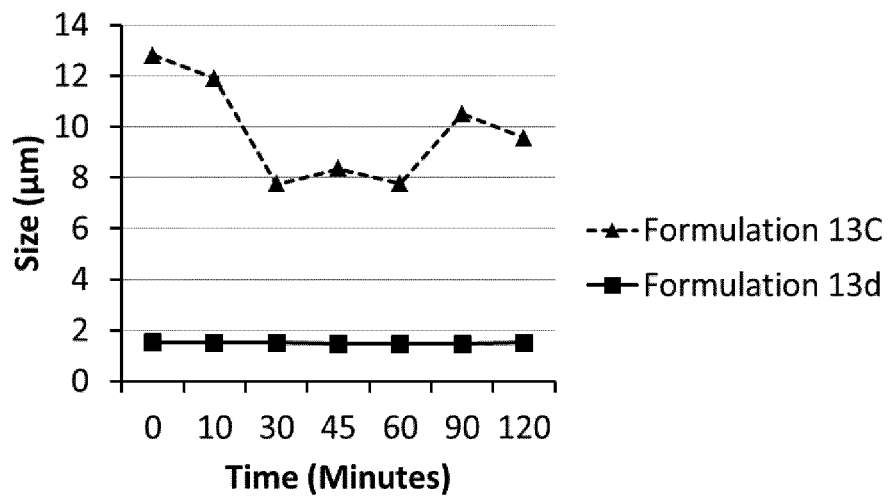

FIG. 54 shows a specific comparison of the 050 values for Formulation 13c and Formulation 13d analysed using the Malvern wet analysis method.

Figure 55:
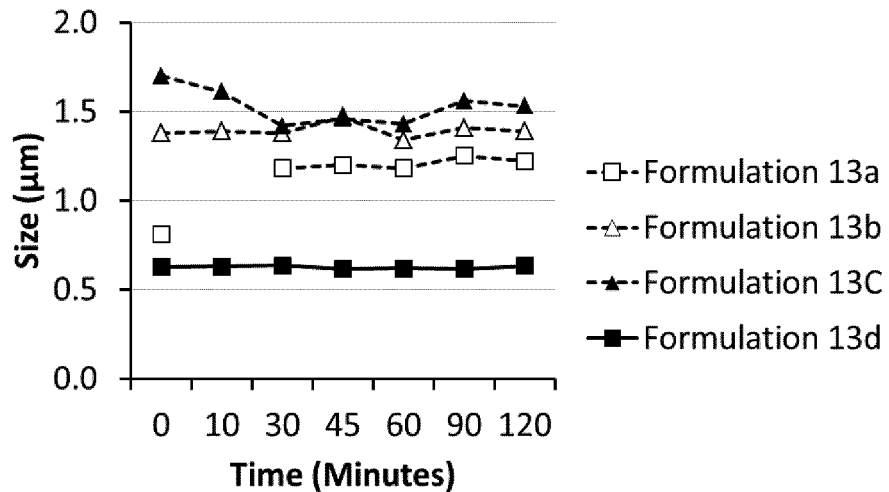

FIG. 55 shows a comparison of the 0 10 values for Formulations 13a-d analysed using the Malvern wet analysis method. Operator error resulted in the loss of the 10 minute sample for Formulation 13a.

Figure 56:
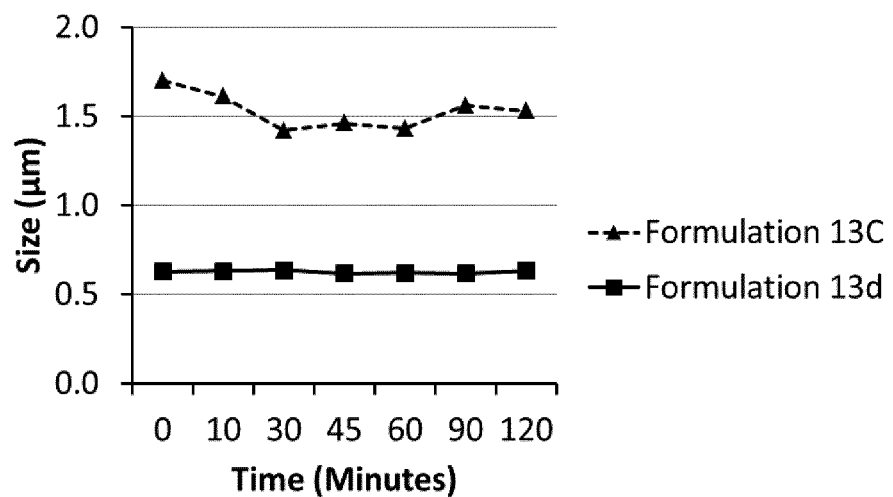

FIG. 56 shows a specific comparison of the 0 10 values for Formulation 13c and Formulation 13d analysed using the Malvern wet analysis method.

Figure 57:
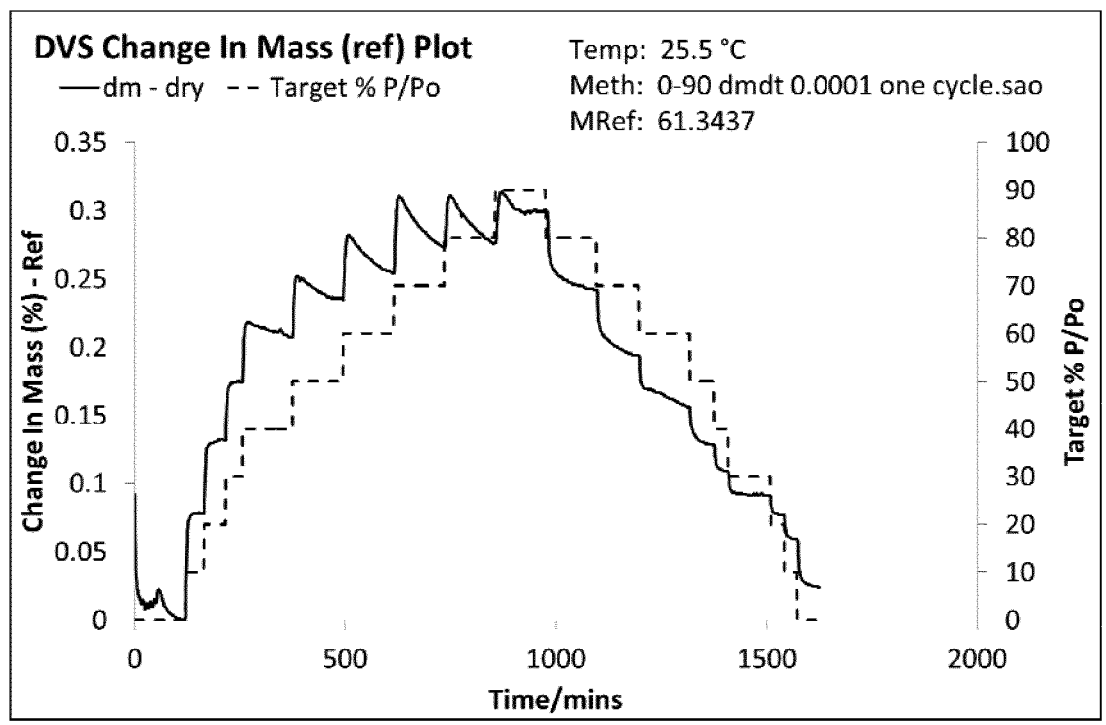

FIG. 57 shows the OVS trace for the co-micronised material used in Formulations 14a and 14b, co-jet milled glycopyrrolate and magnesium stearate, OVS analysis commenced immediately after co-jet milling.

Figure 58:
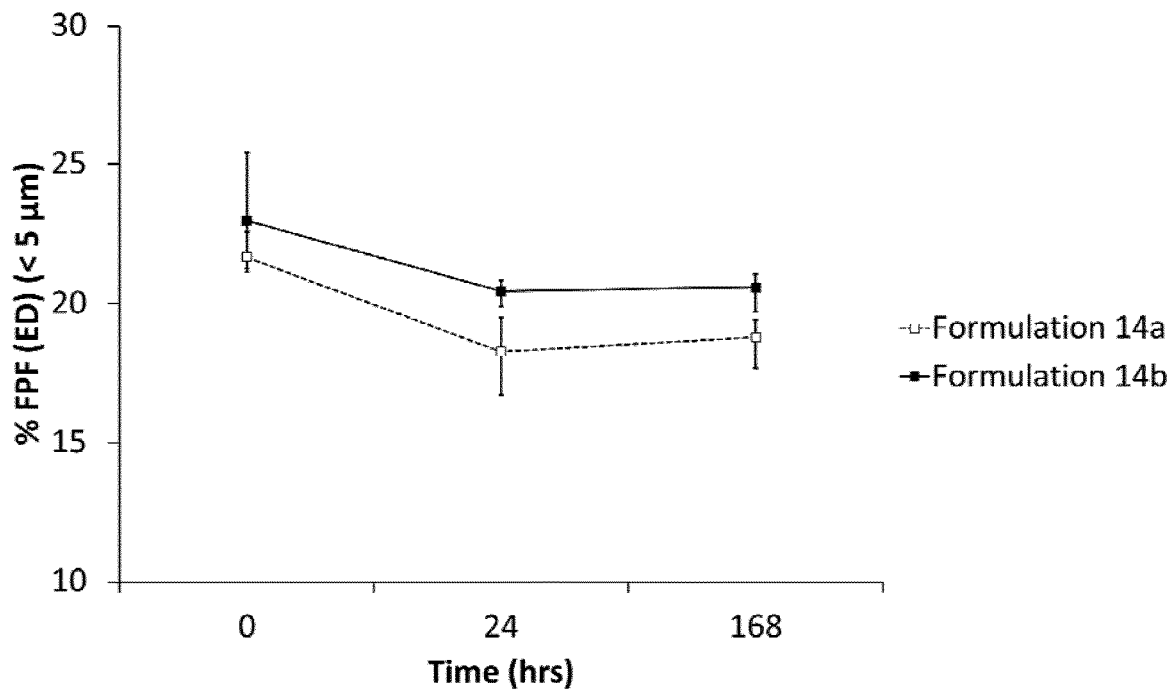

FIG. 58 shows a comparison of the Fine Particle Fraction (% FPF(EO)<5 μm for Formulations 14a and 14b. Mean±range, n=3. FPF was assessed immediately, 24 hrs and 1 week after manufacture.

Figure 59:
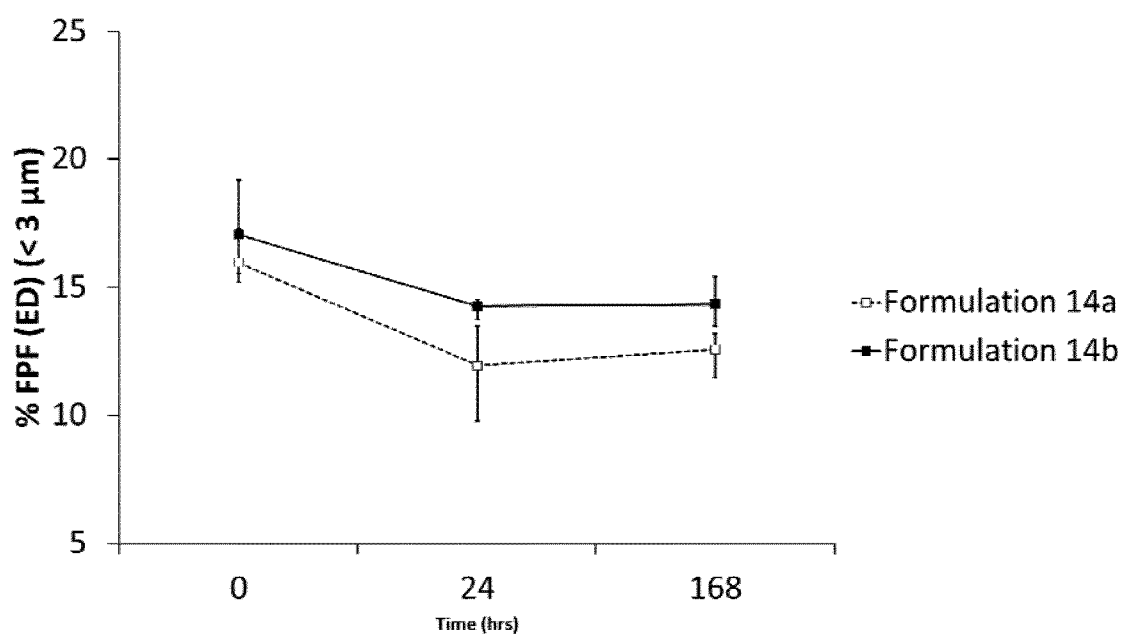

FIG. 59 shows a comparison of the Fine Particle Fraction (% FPF(ED)<3 μm for Formulations 14a and 14b. Mean±range, n=3. FPF was assessed immediately, 24 hrs and 1 week after manufacture.

DETAILED DESCRIPTION OF INVENTION

In the present invention we have determined that milling of glycopyrrolate with magnesium stearate produces a more useful particle size distribution profile than milling glycopyrrolate in the absence of the magnesium stearate because the co-jet milled formulation has a Particle Size Distribution (PSD) with a portion greater than 10 μm which is less than 20% by volume or mass. Co-jet milling glycopyrrolate with magnesium stearate also produces an inhalable formulation with suitable $D_{10}$, $D_{50}$ and $D_{90}$ values ($D_{50}$<10 μm) but co-jet milling with magnesium stearate significantly reduces the fraction >10 μm. This results in a composite formulation wherein almost all the co-jet milled formulation is less than 10 μm as suitably determined by a MALVERN MASTERSIZER® or similar laser diffraction equipment. The subsequent conditioning of the active in the presence of the magnesium stearate allows the improved particle size distribution profile of the active particle size to be maintained.

Without wishing to be bound by theory, we consider that the presence of the magnesium stearate helps to reduce the >10 μm fraction during the milling process and then also helps to maintain it during conditioning, because it assists in the conversion of physically unstable amorphous surfaces to physically stable crystalline surfaces and allows conditioning to act rapidly on the milled glycopyrrolate particles.

(1) Firstly, the magnesium stearate facilitates a more consistent powder flow into the milling chamber which promotes a more consistent milling action. A more efficient milling action ensures the milling energy is able to act more evenly across all the particles rather than a punctuated milling action as seen when the powder is introduced unevenly into the milling chamber. Consequently the particle sizes are smaller for formulations co-micronised with a magnesium stearate, as demonstrated by the $D_{10}$, $D_{50}$ and $D_{90}$ values exemplified below. Furthermore the particle size distributions are narrower for formulations co-micronised with magnesium stearate, as demonstrated by $D_{10}$, $D_{50}$ and $D_{90}$ values, especially when calculated using the span equation:

$$\text{Span} = \frac{D_{90} - D_{10}}{D_{50}}$$

(2) Secondly, the magnesium stearate coating on the glycopyrrolate acts as a physical spacer between the glycopyrrolate particles allowing the conditioning environment to permeate the glycopyrrolate powder bed more efficiently than a glycopyrrolate only formulation. This greater permeation efficiency assists in the conversion of the physically unstable amorphous surfaces to physically stable crystalline surfaces minimising the occurrences when glycopyrrolate particles are in contact with one another, (3) Thirdly, the magnesium stearate may cover regions of amorphous glycopyrrolate material. Since the magnesium stearate is present during the micronisation process it is able to immediately minimise contact between amorphous surfaces on neighbouring particles by covering the amorphous surfaces. This results in a reduced tendency for the amorphous surfaces to bind to one another upon recrystallisation as measured by a reduced >10 µm fraction. Since the particles are so small the conditioning environment (e.g. moisture and temperature) is still able to permeate via the non-covered parts, in particular the juncture between the glycopyrrolate and the magnesium stearate on the composite glycopyrrolate particle and facilitate conversion of its unstable amorphous parts to create a physically stable crystalline particle, and (4) Finally, the desiccated milling environment, especially a milling environment with a humidity below 20% RH, suspends or retards a reversion of the physically unstable amorphous glycopyrrolate surfaces to physically stable crystalline surfaces of the micronized composite particles whilst in the milling chamber and associated collection vessel.

Reduction of the fraction of active greater than 10 µm reduces active pharmaceutical ingredient (API) wastage because otherwise the >10 µm fraction might have to be physically removed prior to blending with other API or excipient.

The process of the invention provides for a more predictable starting material because there is no longer an appreciable >10 µm fraction. Furthermore the stability conferred by the process of the invention ensures that a >10 µm fraction is much less likely to develop. Optionally, this improved process removes the need for further processing prior to blending with a carrier thereby speeding up formulation manufacture.

A further potential advantage of the present invention is that it allows the administration of even smaller doses than previously used. The reduction of the dose is made possible by the more consistent and predictable administration of the glycopyrrolate, for example, through a consistently improved Fine Particle Fraction (FPF(MD) or FPF(ED)) and Fine Particle Dose (FPO) compared to that observed in connection with the conventional formulations. Consequently, while the dose dispensed is smaller, the amount of active agent being administered to the desired parts of the airways is the same, with the same therapeutic effect being achieved.

Milling Preferably the glycopyrrolate and the magnesium stearate are pre-mixed to give a roughly homogeneous blend before being co-jet milled together as measured as a percentage coefficient of variation, as known in the art, of less than 25%, preferably less than 20%, more preferably less than 15%.

The terms "co-micronise" and "co-jet mill" are synonymous when used herein.

Suitable mixing equipment for any initial pre-mix of the magnesium stearate and the glycopyrrolate includes low shear tumble blenders such as a Turbula® powder blender and high-shear mixers such as a MiPro® powder blender or a Diosna®.

Micronising reduces the particle size of the glycopyrrolate to a size that is suitable for administration by inhalation. The diameter of these inhalable particles is preferably less than 10 µm, preferably 0.1 µm to 10 µm, and preferably 0.1 µm to 6 µm or more preferably 0.5 µm to 5 µm as measured by mass or volume as suitably determined by a MALVERN MASTERSIZER or similar laser diffraction equipment. Particles having diameters greater than about 10 µm are likely to impact the walls of the throat and generally do not reach the lung. Particles having diameters in the range of about 2 µm to about 5 µm will generally be deposited in the respiratory bronchioles whereas smaller particles having diameters in the range of about 0.5 µm to about 2 µm are likely to be deposited in the alveoli and to be absorbed into the bloodstream.

Co-jet milling glycopyrrolate with magnesium stearate, significantly reduces the propensity of the micronised drug substance to form >10 µm aggregates/agglomerates immediately after milling. When co-jet milled, magnesium stearate particles form a physically fused and proud particulate coating on the glycopyrrolate particles, and they create inter-particulate spaces between the particles of glycopyrrolate. These spaces are thought to facilitate permeation of the conditioning atmosphere into the glycopyrrolate powder bed during the conditioning step. The presence of this coating can be established by energy-dispersive X-ray spectroscopy (EDX). The presence of composite particles can be determined by aerosolising a sample from an inhaler into a Next Generation Impactor (NGI) at 90 L/min (equivalent to a 4 kPa pressure drop). Double coated carbon conductive tabs are placed directly under the air nozzles of stages 5, 6 and 7 of the NGI to capture the smaller powder particles. Double coated adhesive tabs prevent movement of the tab during the NGI assessment but are also small enough so that the overall airflow characteristics of the NGI pathway are not adversely affected. Once done, the powder-coated carbon conductive tabs can be transferred to SEM carbon specimen mounts, or similar. The sample can be viewed using SEM and EDX specifically looking for co-location of magnesium and bromine, in the case of magnesium stearate and glycopyrronium bromide.

When the conditioning step is complete the >10 µm fraction of the co-jet milled and co-conditioned glycopyrrolate and magnesium stearate suitably remains less than 15% by volume or mass, more preferably less than 10% by volume or mass, or more preferably less than 5% by volume or mass after 6 months, 12 months, 24 months or 36 months, suitably after packaging into a blister or capsule or inhaler when stored at ambient conditions, which are considered to be between 20 and 26° C.; relative humidities depends on the specific temperature and the pressure of the system of interest but are typically 50% and 60%.

When the conditioning step is complete the span, as defined above, of the co-jet milled and co-conditioned glycopyrrolate and magnesium stearate suitably remains less than 150, more preferably less than 120, or more preferably less than 100. Preferably the span of the co-jet milled and co-conditioned glycopyrrolate and magnesium stearate is less than 150, more preferably less than 120, more preferably less than 100, or more preferably less than 50 prior to blending with carrier particles.

Jet milling involves the supply of gas, such as nitrogen, helium or air at pressures in the region of about 6 to 12 bar and particles to be milled are entrained in the feed gas. The jet milling operation occurs at close to atmospheric pressure, and has a milling duration measured in milliseconds. The final outlet temperature of the jet milling is typically at about room temperature (preferably 10° C. and 35° C., more preferably 20° C. and 26° C.). The milling gas is introduced into the mill at about room temperature, and exits the mill at about the same temperature. During the process however, the gas will change temperature significantly as it exits the supersonic nozzle (lower pressure and temperature) and is subsequently warmed by the energy released in the jet milling operation. Preferably the co-milling temperature is above 0° C.

According to the prior art, U.S. Pat. No. 8,235,314 B2 for example, it is considered advantageous to perform the micronization process with humidified gas (typically air or nitrogen) to produce the best particles in terms of size, stability and other valuable properties. The prior art, and U.S. Pat. No. 8,235,314 B2 in particular considered it advantageous to maximize the amount of water vapour present during the micronization process, without producing liquid condensate.

In contrast we have found that when co-jet milling with magnesium stearate it is particularly preferred to adopt different milling parameters. A preferred embodiment is a method comprising co-jet milling unmicronised glycopyrrolate and magnesium stearate with a desiccated milling gas in particular the desiccated milling gas having reduced RH, preferably a humidity below 20% RH, preferably below 15% RH, preferably below 10% RH, preferably below 5% RH, more preferably below 2.5% RH.

The conditioning step is preferably carried out prior to blending with any moisture-laden particulates, for example prior to addition of lactose or in particular alpha-lactose monohydrate. Therefore the conditioning is carried out in the absence of lactose or alpha-lactose monohydrate. If the unconditioned or partially conditioned glycopyrrolate particles are blended prematurely with moisture-laden particles any amorphous glycopyrrolate may revert to crystalline material whilst in contact with the moisture-laden particles and fuse to these other particles, forming agglomerates. Consequently, the aerosol performance will be adversely affected because the particle size will have increased. This is particularly problematic when the moisture-laden particles include carrier lactose, for example alpha-lactose monohydrate, because the glycopyrrolate will remain attached to the carrier and then be swallowed rather than inhaled into the airways.

In a preferred embodiment crystalline glycopyrrolate is jet milled in a Hosokawa Alpine® 100 AFG fluid bed opposed jet mill. Other suitable jet milling equipment include, for example, the MC 44 IR Chrispro® Jet-Mill (Micromacinazione SA), Hosokawa's Alpine® AS-50, AS-100, AFG 140, AFG200, AFG280 and AFG400 jet mills.

The co-jet milling powder feed rates for a 50 mm diameter jet mill, for example a Hosakowa AS-50, should be kept low (preferably <20 g/min) to ensure an optimal coating of the glycopyrrolate by the magnesium stearate. Feed rates higher than 20 g/min still achieve coating by the magnesium stearate but it will be sub-optimal because too much powder passes through the mill to ensure sufficient energy is applied to each particle to achieve the desired coating with magnesium stearate. When feed rates higher than 20 g/min are used, powder conditioning factor (vi) mentioned below must be employed, optionally with powder conditioning factors (i)-(viii). Feed rates will vary depending on the size of the mill used. Consequently, jet mills with 100 mm diameters, for example a Hosakowa AS-100 spiral jet mill, will be able to accommodate higher feed rates, typically <50 g/min. The jet milling may be carried out at an averaged powder feed rate of preferably between 0.1 and 50 g/min, preferably at a feed rate of between 0.5 and 40 g/min, preferably between 1 and 30 g/min, preferably between 1.5 and 25 g/min, preferably between 0.1 and 20 g/min, preferably between 0.5 and 15 g/min, preferably between 1 and 10 g/min, preferably between 1.5 and 5 g/min.

The co-micronised particles extracted from the micronisation process may be collected and may be transported to a suitable conditioning vessel, in which the powder conditioning factors (i)-(viii) mentioned below may be used. In such a system preferably the particles are all exposed to the humidity for sufficient time, as detailed herein, such as at least 10 minutes. Preferably all the powder remains in the vessel from start to finish of this process.

In accordance with a preferred embodiment of the present invention, the dry powder formulation comprising glycopyrrolate is prepared by co-jet milling with magnesium stearate, then undergoes any one of the powder conditioning steps (i)-(viii) mentioned below.

In a preferred embodiment the glycopyrrolate is mixed with the magnesium stearate to give a homogeneous blend prior to being co-jet milled, the admixture is then co-jet milled and then undergoes any one of the powder conditioning steps (i)-(viii) mentioned below.

Preferably the glycopyrrolate is co-jet milled with from 1 to 25% (w/w), more preferably from 2 to 20% (w/w), more preferably 3 to 15% (w/w), more preferably 4 to 10% (w/w) but most preferably from 5 to 7.5% (w/w) magnesium stearate.

Where necessary or useful, the glycopyrrolate and/or magnesium stearate are sieved prior to co-jet milling.

Conditioning

To produce an improved formulation, after co-micronisation the glycopyrrolate and magnesium stearate are subjected to conditioning variables which might include:

(i) Relative Humidity (RH)

The present invention utilises humidity to assist in conditioning of the glycopyrrolate. In one embodiment of the invention, the conditioning involves exposing the co-jet milled glycopyrrolate and magnesium stearate to moisture within the humidity ranges of 20%-95% RH, preferably 40-90% RH, 45-90% RH or 50-88% RH or more preferably 60-87%.

In a preferred embodiment of the invention, the conditioning humidity is greater than ambient humidity, preferably greater than 50% RH.

(ii) Temperature

In one embodiment of the invention, the conditioning temperature is preferably in the range 5° C. to 88° C., more preferably 10° C. to 50° C., more preferably 24° C. to 50° C.

The RH at these temperatures may be in the range of 20 to 100%, preferably 30 to 97%, more preferably 40 to 95%, more preferably 45 to 95% and most preferably 50 to 90%, suitably provided the conditioning environment is maintained above the dew point temperature (Td)—The dew point is the temperature at which the water vapour in air at constant barometric pressure condenses into liquid water at the same rate at which it evaporates. At temperatures below the dew point, water will leave the air and condense on an available solid surface which is of suitable temperature. Condensed water on micronized glycopyrrolate should be carefully controlled and consequently the selected conditioning parameters of temperature and humidity should be chosen to avoid this problem.

The conditioning may be provided by ambient conditions or by stability cabinets or by supersaturated salt solutions, all of which are exemplified below.

(iii) Conditioning Surface

In one embodiment of the invention, the co-jet milled glycopyrrolate powder is preferably placed on a tray or equivalent surface. The broadest range of conditions involves the powder being preferably agitated or turned to ensure that all of the particles are equally exposed to the conditioning atmosphere. The turning or agitating also helps to avoid or reduce agglomeration of the particles during the conditioning process. When more energetic conditioning environments are selected for conditioning on a tray or equivalent surface, the frequency of turning or agitation may need to be preferably every few minutes, preferably every few seconds or more preferably continuous until the formation of a stable material, for example where any amorphous surfaces of the micronized glycopyrrolate revert to a crystalline state, suitably as determined by dynamic vapour sorption.

The conditioning vessel may be for example a tray, or a suitable surface for retaining the co-jet milled powder. Alternatively the conditioning vessel may be a bag.

(iv) Duration

The conditioning of the co-jet milled glycopyrrolate powder preferably takes place over a period of at least about 60 minutes, at least about 65 minutes, at least about 70 minutes, at least about 80 minutes, at least about 85 minutes, at least about 90 minutes, 2 hours, 3, 4, 5, 6, 8, 10, 12, 14, 18, 24, 36 or at least 48 hours. The broadest range involves a period of at least about 10 minutes. It is reiterated that the duration of required conditioning is generally affected by the energy provided by conditioning environment. Highly energetic conditioning environments may result in a more rapid onset of changes in the material being conditioned.

(v) Period for Initiating the Conditioning

In one preferred embodiment the conditioning is initiated within 30 minutes of completing the milling, within 25 minutes, within 20 minutes, within 15 minutes, preferably within 10 minutes, more preferably within 5 minutes, more preferably within 2 minutes of completing the co-jet milling of the glycopyrrolate and anti-adherent. The broadest range involves conditioning immediately after completing the co-jet milling of the glycopyrrolate and anti-adherent.

(vi) Ensuring that all the Particles are all Exposed to the Humidity

The conditioning vessel should preferably allow exposure of all of the micronized composite particles to the moisture applied from the conditioning atmosphere. The powder may be agitated or not agitated. If the powder is not agitated it should preferably be placed on a tray or suitable expansive surface, and preferably spread evenly in a thin layer over the tray ensuring particle contact is minimised. The broadest range of conditions involves a suitable expansive surface.

(vii) A Fluidised Bed

As an alternative, the co-jet milled glycopyrrolate powder may be transferred to a system which creates a fluidised bed of the co-jet milled powder. Such systems are known in the art. The co-jet milled powder may be difficult to fluidise alone, and consequently fluidisation media are advantageously added, such as metal, plastic, glass or ceramic beads, typically with diameters in the range 100 μm to 5 mm.

A fluidised bed aerosol technique for this purpose could be one as described by Morton et al (J. Aerosol Science, Vol. 26, No. 3, p 353 and references therein).

In one preferred embodiment the conditioning takes place using a Resonance Acoustic Mixer (RAM), optionally wherein the powder conditioning is initiated within 30 minutes of completing the milling, within 25 minutes, within 20 minutes, within 15 minutes, preferably within 10 minutes, more preferably within 5 minutes, preferably within 2 minutes or more preferably and in the broadest range the conditioning is initiated immediately after completing the co-jet milling of the glycopyrrolate and magnesium stearate.

(viii) Ventilation

Immediately after co-jet milling, glycopyrrolate samples possess numerous amorphous regions that contain moisture extracted from the environment. When regions of amorphous glycopyrrolate revert to the crystalline state, the crystal matrix extrudes the bound moisture onto the surface of the glycopyrrolate particle. Small hermetically sealed containers, wherein the ratio of headspace volume ($cm^3$) to poured bulk powder volume ($cm^3$) is less than 1:1 are considered unventilated conditions. Glycopyrrolate samples that are stored in hermetically sealed containers, glass vials for example, are less efficient at releasing this moisture into the atmosphere and it remains on the particle surface. This retained moisture is then able to adversely interact with the amorphous regions on neighbouring glycopyrrolate particles and catalyse additional amorphous to crystalline reversions. This is particularly problematic when glycopyrrolate particles remain in contact with one another whilst the amorphous regions undergo amorphous to crystalline reversion because the amorphous regions on particles then form solid bridges as they crystallise, solid bridging results in agglomerates.

In contrast, a ventilated conditioning atmosphere permits permanent removal of this surface moisture away from the particle surface after amorphous regions of glycopyrrolate have undergone amorphous to crystalline reversion. Consequently there is insufficient moisture to cause significant agglomeration. Ventilation is the pervasive movement of unsaturated atmosphere between stationary particles comprising the powder bed.

A preferred embodiment utilises a ventilating atmosphere to assist in conditioning of the co-jet milled glycopyrrolate. It is preferred that the glycopyrrolate powder bed is subjected to a ventilated atmosphere to ensure permanent removal of surface moisture from the co-jet milled glycopyrrolate. The ventilating atmosphere is unsaturated and always has the capacity to absorb more moisture from the powder bed. This ability to absorb moisture is found with a ventilating atmosphere having relative humidity in the range of 10%-95% RH, preferably 30-90% RH, 45-90% RH or 50-88% RH or more preferably 60-87%. The broadest range involves a ventilating atmosphere having relative humidity in the range of 20%-95% RH.

In a preferred embodiment, the conditioning involves exposing the co-jet milled glycopyrrolate and magnesium stearate to a ventilating atmosphere, preferably wherein the atmosphere passes over and through the co-jet milled glycopyrrolate particles. Preferably, the ventilating atmosphere is air; preferably the ventilating atmosphere is air having relative humidity in the range of 10%-95% RH, preferably 30-90% RH, 45-90% RH or preferably 50-88% RH or more preferably 60-87% RH.

In a preferred embodiment, the conditioning involves exposing the co-jet milled glycopyrrolate and magnesium stearate agent to a ventilating atmosphere, preferably wherein the ventilating atmosphere passes over and through the co-jet milled glycopyrrolate and magnesium stearate at a rate of less than 100 $cm^3/s$, less than 10 $cm^3/s$, less than 5 $cm^3/s$, less than 2 $cm^3/s$, less than 1 $cm^3/s$, preferably less than 0.8 $cm^3/s$, preferably less than 0.6 $cm^3/s$, preferably less than 0.4 $cm^3/s$, preferably less than 0.2 $cm^3/s$, preferably less than 0.1 $cm^3/s$, more preferably about 0.001 $cm^3/s$.

In a preferred embodiment, the conditioning involves exposing the co-jet milled glycopyrrolate and magnesium stearate to a ventilating atmosphere, preferably wherein the ventilating atmosphere passes over and through the co-jet milled glycopyrrolate and magnesium stearate. The ventilating atmosphere is surplus to requirement, for example provided by a large volume (>0.5 m$^3$), for example a powder control booth, so the moisture released by the co-jet milled glycopyrrolate and magnesium stearate in to the ventilating atmosphere does not alter the relative humidity by more than 5% RH, preferably not more than 4% RH, preferably not more than 3% RH, preferably not more than 2% RH, preferably not more than about 1% RH.

During the conditioning, the ventilating atmosphere can undergo partial or complete supplementation.

In a preferred embodiment, the conditioning involves exposing the co-jet milled glycopyrrolate and magnesium stearate to a ventilating atmosphere, preferably wherein the ventilating atmosphere passes over and through the co-jet milled glycopyrrolate and magnesium stearate. Preferably, the volume ratio of ventilating atmosphere (cm$^3$) to poured bulk powder (cm$^3$) is more than 1:1, preferably more than more than 10:1, preferably more than more than 100:1, preferably more than more than 1,000:1, preferably more than 10,000:1, preferably more than 100,000:1, preferably more than 1,000,000:1, more preferably more than 10,000,000:1.

As the examples discussed below indicate, a combination of two or more of these measures (i) to (viii) leads to acceptable results.

In one preferred embodiment for conditioning the co-jet milled glycopyrrolate, the powder conditioning factors (i), (ii), (iii), (iv), (v), (vi), (vii) and (viii) above are all selected for conditioning the co-jet milled glycopyrrolate and magnesium stearate, using the broadest ranges of conditions where relevant.

In a preferred embodiment for conditioning the co-jet milled glycopyrrolate and magnesium stearate, the powder conditioning factors include 60-87%. RH, 24° C. to 50° C., the co-jet milled glycopyrrolate powder is preferably placed on surface for at least about 1 hour, wherein the conditioning vessel should preferably allow exposure of all of the co-jet milled powder to the moisture applied from the conditioning atmosphere.

Force Control Agent

In a yet further embodiment, the dry powder formulation comprising glycopyrrolate further comprises an additional additive material, such as a so-called force control agent. A force control agent is an agent which reduces the cohesion between the fine particles within the powder formulation, thereby promoting deagglomeration upon dispensing of the powder from the dry powder inhaler. Suitable force control agents are disclosed in WO1996023485 and they preferably consist of physiologically acceptable material, despite the fact that the material may not always reach the lung.

The force control agent may comprise or consist of one or more compounds selected from amino acids and derivatives thereof, and peptides and derivatives thereof, the peptides preferably having a molecular weight from 0.25 to 1 000 Kda. Amino acids, peptides and derivatives of peptides are physiologically acceptable and give acceptable release or deagglomeration of the particles of active material on inhalation. Where the force control agent comprises an amino acid, it may be one or more of any of the following amino acids: leucine, isoleucine, lysine, valine, methionine, and phenylalanine. The force control agent may be a salt or a derivative of an amino acid, for example aspartame or acesulfame K. The D- and DL-forms of amino acids may also be used.

Force control agents which are particularly suitable for use in the present invention include, amino acids including leucine, lysine, arginine, histidine, cysteine and their derivatives, lecithin and phospholipids. The inclusion of these force control agents may improve the efficacy of the glycopyrrolate for treating respiratory disorders such as COPD, asthma or CF.

Force control agents may include one or more water soluble substances. This helps absorption of the force control agent by the body if it reaches the lower lung. The force control agent may include dipolar ions, which may be zwitterions. It is also advantageous to include a spreading agent as a force control agent, to assist with the dispersal of the composition in the lungs.

Suitable spreading agents include surfactants such as known lung surfactants (e.g. ALEC, Registered Trade Mark) which comprise phospholipids, for example, mixtures of DPPC (dipalmitoyl phosphatidylcholine) and PG (phosphatidylglycerol). Other suitable surfactants include, for example, dipalmitoyl phosphatidylethanolamine (DPPE), dipalmitoyl phosphatidylinositol (DPPI).

The force control agent may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the force control agent may be cholesterol.

Other possible force control agents include sodium benzoate, hydrogenated oils which are solid at room temperature, talc, titanium dioxide, aluminium dioxide, silicon dioxide and starch. Also useful as force control agents are film-forming agents, fatty acids and their derivatives, as well as lipids and lipid-like materials.

The inclusion of an additive material in the dry powder formulation may suitably confer one or more of the following benefits: enhancing the powder's dispersability; protecting the formulation from the ingress of moisture; enhancing the speed and reproducibility of the conditioning process.

In a preferred embodiment the magnesium stearate is suitably located on the surface of the glycopyrrolate after milling. Where an additional additive material is present, it is also suitably located on the glycopyrrolate surface.

Lactose fines also modify the interaction between the glycopyrrolate and carrier particles affecting aerosol performance. In one embodiment the dry powder formulation may comprise fine lactose which is in an amount of preferably >3% (w/w), more preferably >5% (w/w) more preferably >8% (w/w) of the formulation residing in a blister or capsule or other suitable dispensing receptacle.

Powder Storage Co-jet milled glycopyrrolate formulations are suitably packaged for storage and/or delivery and are preferably stable for at least 1, 2 or 3 years when stored at ambient temperatures and humidities, i.e. the packaged formulations or products comprising the formulations do not have to be stored in a controlled environment in order to exhibit the desired stability.

According to one aspect, the co-jet milled glycopyrrolate formulation is stable for a period of at least 6 months, preferably at least 1 year, more preferably a period of at least 2 years and most preferably a period of at least 3 years as determined by a Fine Particle Fraction (FPF(MO)) (<5 μm), suitably wherein the FPF does not decrease by preferably more than 20%, preferably more than 15%, preferably more than 10% or more preferably by more than 5% of the FPF exhibited by the newly manufactured co-jet milled formulation.

In one aspect the co-jet milled glycopyrrolate formulation can be consistently dispersed over periods of at least 6 months, preferably 1 year, preferably at least 2 years or preferably at least 3 years when stored at ambient temperature and ambient humidity, meaning that the FPF does not decrease by preferably more than 20%, preferably more than 15%, preferably more than 10% or more preferably by more than 5% of the FPF exhibited by the newly receptacle filled formulation.

In one aspect the co-jet milled glycopyrrolate formulation has a consistent particle size distribution as measured by, for example MALVERN MASTERSIZER® meaning that the 090 does not increase by preferably more than 20%, preferably more than 15%, preferably more than 10% or more preferably by more than 5% of the 090 exhibited by the newly manufactured co-jet milled formulation.

In one aspect the co-jet milled glycopyrrolate formulation has a consistent FPF or FPO over the same period of time, meaning that the FPF or FPO does not decrease by preferably more than 20%, preferably more than 15%, preferably more than 10% or more preferably by more than 5% of the FPF or FPO exhibited by the newly receptacle filled co-jet milled formulation.

In one embodiment, the co-jet milled glycopyrrolate formulation has a Particle Size Distribution having the profile of D10<10 μm, D50<15, D90<30 μm, for a period of at least 6 months, preferably 1 year, preferably at least 2 years or preferably at least 3 years after the conditioning process has been completed, when stored at ambient temperature and ambient humidity.

In one embodiment of the invention, the FPF (<5 μm) of the co-jet milled glycopyrrolate formulation is greater than about 30% over a period of at least 6 months, at least 1 year, at least 2 years or at least 3 years when stored at ambient temperature and ambient humidity.

In another embodiment of the invention, the FPF (<5 μm) of the co-jet milled glycopyrrolate formulation is greater than about 40% over a period of at least 1 year, at least 2 years or at least 3 years when stored at ambient temperature and ambient humidity.

Preferably, the fine particle fraction FPF(MD) (<5 μm) of the co-jet milled glycopyrrolate formulation is consistently greater than 30% or greater than 40% when the co-jet milled and co-conditioned glycopyrrolate formulations are stored under standard testing conditions, such as 25° C./60% RH for 1 year, 30° C./60% RH for 6 months, or 40° C./70% RH for 3 months or 40° C./75% RH for 3 months. These standard testing conditions are employed after the co-jet milled glycopyrrolate has been conditioned and made stable, preferably wherein the co-jet milled glycopyrrolate has been conditioned and formulated with lactose and filled into a receptacle suitably to be delivered from an inhaler.

Carrier Particles

Dry powder formulations for inhalation in the treatment of respiratory diseases are generally formulated by mixing a micronised active pharmaceutical ingredient with coarse carrier particles to give an ordered mixture. The carrier particles make the micronised active pharmaceutical ingredient less cohesive and improve its flowability. This makes the powder easier to handle during the manufacturing process. The micronised active particles tend to adhere to the surface of the carrier particles when stored in a dry powder inhaler device but are dispersed from the surfaces of the carrier particles on inhalation into the respiratory tract to give a fine aerosol. The larger carrier particles impact on the throat due to their inertia and are mostly deposited in the oropharyngeal cavity.

One embodiment may include carrier particles which are mixed with the co-micronised glycopyrrolate in a ratio of from 2000:1 to 5:1 by mass, especially from 200:1 to 20:1 by mass. The carrier particles may be composed of any pharmacologically inert material or combination of materials which is acceptable for inhalation. They are suitably composed of one or more crystalline sugars including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or alpha lactose monohydrate or anhydrous lactose.

Preferably substantially all (by weight or volume) of the carrier particles have a diameter of 20 to 1000 μm, more preferably 50 to 500 μm, but especially 20 to 250 μm. The diameter of substantially all (by weight) of the carrier particles is suitably less than 355 μm. This provides good flow and entrainment characteristics and improved release of the active particles in the airways to increase deposition of the active particles in the lower lung.

It will be understood that throughout this specification the diameter of the particles referred to is the diameter of the particles as suitably determined by a MALVERN MASTERSIZER® or similar laser diffraction equipment.

Additional Active Ingredients

The formulations may include one or more further active agents, in addition to the glycopyrrolate. Especially preferred additional classes of active agents may include, pharmaceutically active agents which are known to be useful in the treatment of respiratory disorders, such as $\beta_2$-agonists, steroids, anticholinergics, phosphodiesterase-4-inhibitors, $A_{2a}$ agonists, IL-13 inhibitors and calcium blockers and the like. In one embodiment, the formulation of the present invention does not include formoterol.

In a further aspect the glycopyrrolate and the antiadherent agent are micronised together with at least one (preferably one, two or three) additional active ingredients to give a fixed dose combination. That or each additional active ingredient is preferably selected from the group consisting of anti-inflammatory, bronchodilatory, antihistamine, decongestant and anti-tussive drug substances that are suitable for administration by inhalation, for example for the treatment of a respiratory disease.

Suitable $\beta_2$-adrenoceptor agonists include albuterol (salbutamol), metaproterenol, terbutaline salmeterol, fenoterol, indacaterol, procaterol, and especially, formoterol, carmoterol, TA-2005, GSK159797 and pharmaceutically acceptable salts thereof.

In a further aspect the formulation comprises co-micronised and conditioned glycopyrrolate and magnesium stearate, subsequently formulated with the β2-adrenoceptor agonist indacaterol maleate.

In another aspect the co-jet milled and conditioned glycopyrrolate and magnesium stearate are in combination with the β$_2$-adrenoceptor agonist indacaterol maleate for use in simultaneous or sequential administration in the treatment of an inflammatory or obstructive airways disease, optionally wherein any single formulation, or any combined formulation, comprises at least one particulate pharmaceutically acceptable carrier.

In an alternate embodiment a medicament comprising co-micronised and co-conditioned glycopyrrolate and magnesium stearate, and the β$_2$-adrenoceptor agonist vilanterol trifenatate, for simultaneous or sequential administration in the treatment of an inflammatory or obstructive airways disease, optionally wherein any single formulation, or any combined formulation, comprises at least one particulate pharmaceutically acceptable carrier.

Bronchodilatory drugs that may be used together with glycopyrrolate include anticholinergic or antimuscarinic agents, in particular umeclidinium bromide, ipratropium bromide, oxitropium bromide, tiotropium salts, CHF 4226 (Chiesi) and SVT-40776.

Steroids that may be used together with glycopyrrolate include glucocorticosteroids such as budesonide, beclamethasone, fluticasone, ciclesonide or mometasone.

PDE4 inhibitors that may be used together with glycopyrrolate include cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), KW-4490 (Kyowa Hakko Kogyo), VM5541UM565 (Vernalis), T-440 (Tanabe), KW-4490 (Kyowa Hakko Kogyo) and GRC 3886 (Oglemilast, Glenmark).

In a preferred embodiment any further active ingredient is salmeterol, indacaterol or mometasone.

Preferred triple combinations of active contain glycopyrrolate, salmeterol and mometasone; glycopyrrolate, indacaterol and mometasone; glycopyrrolate salmeterol and ciclesonide; glycopyrrolate, indacaterol and ciclesonide; glycopyrrolate, salmeterol and 3-methylthiophene-2-carboxylic acid (6S, 9R, 10S, 11 S, 13S, 16R, 17R)-9-chloro-6-fluoro-11-hydroxy-17-methoxycarbonyl-10, 13, 16-trimethyl-3-oxo-6,7,8,9, 10, 11, 12, 13, 14, 15, 16, 17-dodecahydro-3H-cyclopenta[a]phenanthren-17-yl ester; or glycopyrrolate, indacaterol and 3-methylthiophene-2-carboxylic acid (6S, 9R, 10S, 11 S, 13S, 16R, 1 ?R)-9-chloro-6-fluoro-11-hydroxy-17-methoxycarbonyl-10, 13, 16-trimethyl-3-oxo-6,7,8,9, 10, 11, 12, 13, 14, 15, 16, 17-dodecahydro-3H-cyclopenta [a] phenanthren-17-yl ester.

In a preferred embodiment the medicament comprises co-jet milled glycopyrrolate and magnesium stearate, which is conditioned, and then combined with fluticasone furoate and vilanterol trifenatate, and the combination is used in the treatment of an inflammatory or obstructive airways disease, optionally for simultaneous or sequential administration.

Packaging

Conditioned glycopyrrolate can be filled into capsules. Capsules can be made with hypromellose (also known as hydroxypropyl methyl cellulose, HPMC) or other celluloses or cellulose derivatives which do not rely on moisture as a plasticizer. The moisture content of such capsules is suitably 10% or less, such as less than 10%, or even below 5% or 3%, and this makes such capsules more suitable for use with glycopyrrolate.

It is known for gelatin capsules to contain in the order of 10 to 15% water and for this to provide a sufficient source of water to create a moisture instability problem. Gelatin capsules can also be made using one or more plasticizers other than water, such as PEG, glycerol, sorbitol, propyleneglycol or other similar polymers and co-polymers, hence allowing the moisture content to be reduced to below 10%, or even below 5% or 3%, and such capsules are preferred for use in the invention.

Alternatively, capsules for use with the formulation of the invention can be made from synthetic plastics or thermoplastics (polyethylene or polycarbonate or related plastics) containing reduced moisture content below 10%, or even below 5% or 3%. Further alternative capsules with reduced moisture content are made from starch or starch derivatives or chitosan.

In an further approach to solving the problem of moisture absorption by dry powder glycopyrrolate formulations, an inhaler device may be used which includes a means for protecting the formulation from moisture, for example storage within a sealed blister pouch, such as a foil blister pouch, with suitable sealing to prevent or reduce the ingress of moisture. Preferably, the powder-containing receptacle (capsule or blister) is stored within a sealed blister pouch, such as a foil sealed blister pouch, with suitable sealing to prevent or reduce the ingress of moisture.

Inhaler devices suitable for delivering inhalable glycopyrrolate formulations include, for example the Breezhaler (Novartis), Turbuhaler (AstraZeneca), GyroHaler® (Vectura), Diskus, Evohaler, Accuhaler or Ellipta (GSK), or Easi-Breathe®, Autohaler® or Genuair (Teva) devices.

Thus, in a further preferred embodiment of the present invention, the dry powder formulation comprising co-jet milled then conditioned glycopyrrolate is stored in packaging made from a material which itself has a moisture content of less than 10%, preferably less than 5% and more preferably less than 3%.

In an alternative embodiment, the dry powder formulation is dispensed from a multidose dry powder inhaler device wherein the powder is stored in a reservoir as opposed to individually packaged doses. In such an embodiment, the device should offer superior moisture protection compared to conventional reservoir devices. For example, the device should include one or more of the following features: a sealed reservoir chamber (for example including a sealing gasket to seal the reservoir chamber), plastics materials exhibiting very low moisture permeability (for forming the walls of the reservoir chamber), and a desiccant.

Powder Aerosol Performance

Preferably, the FPF(MD) of the dry powder formulations of the present invention is at least about 30%, at least about 40%, at least about 50%, at least about 60%, at least about 70% or at least about 80%, suitably as measured using a Monohaler dry powder inhaler used at 60 Umin in a NGI (Copley Scientific).

The Emitted Dose (ED) of the glycopyrrolate in the dry powder formulations of the present invention is consistently between 30 and 60 µg, between 33 and 56 µg, between 36 and 53 µg, between 39 and 50 µg, between 42 and 46 µg or preferably, between 43 and 45 µg as measured using a Monohaler dry powder inhaler used at 60 Umin in a NGI (Copley Scientific).

The Fine Particle Dose (FPO) of the glycopyrrolate in the dry powder formulations of the present invention is consistently at least about 9 µg at least about 10 µg, at least about 11 µg, at least about 12 µg, or preferably at least about 13 µg as measured using a Monohaler dry powder inhaler used at 60 Umin in a NGI (Copley Scientific).

Terms used in the specification have the following meanings:

Glycopyrrolate

Glycopyrrolate is used herein to refer to any composition comprising, or capable of creating in the body, the glycopyrrolate cation. This term includes glycopyrronium salts, intended to encompass any salt form or counterion of glycopyrronium, including but not limited to glycopyrronium bromide, glycopyrronium chloride, or glycopyrronium iodide, as well as any and all isolated stereoisomers and mixtures or stereoisomers thereof. Derivatives of glycopyrronium salts are also encompassed. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxy-benzoate, p-hydroxybenzoate, 1-hydroxynaphthalene-2-carboxylate, 3-hydroxynaphthalene-2-carboxylate, methanesulfonate and benzene-sulfonate.

Glycopyrronium bromide has two stereogenic centres and hence exists in four isomeric forms, namely (3R,2'R)-, (3S,2'R)-, (3R,2'S)- and (3S,2'S)-3-[(cyclopentyl-hydroxy-phenylacetyl)oxy]-1, 1-dimethylpyrrolidinium bromide. The present invention embraces using one or more of these isomeric forms, especially the 3S,2'R isomer, the 3R,2'R isomer or the 2S,3'R isomer, thus including single enantiomers, mixtures of diastereomers, or racemates, especially (3S,2'R/3R,2'S)-3-[(cyclopentyl-hydroxy-phenylacetyl)oxy]-1, I-dimethylpyrrolidinium bromide. In one embodiment, the glycopyrrolate is not R,R-glycopyrrolate.

Metered Dose

Metered dose" or "MD" of a dry powder formulation as used herein is the total mass of active agent present in the metered form presented by the inhaler device in question. For example, the MD might be the mass of glycopyrronium salt present in a capsule for a particular dry powder inhaler, or in a foil blister for use in a particular dry powder inhaler device. The Metered dose is also referred to as the Nominal Dose.

Emitted Dose

Emitted dose" or "ED" as used herein is the total mass of the active agent emitted from the device following actuation. It does not include the material left inside or on the surfaces of the device. The ED is measured by collecting the total emitted mass from the device in an apparatus frequently referred to as a Dose Uniformity Sampling Apparatus (DUSA), and recovering this by a validated quantitative wet chemical assay.

Fine Particle Dose

"Fine particle dose" or "FPO" as used herein is the total mass of active agent which is emitted from the device following actuation which is present in an aerodynamic particle size smaller than a defined limit. This limit is generally taken to be 5 µm if not expressly stated to be an alternative limit, such as 1 µm or 3 µm, etc. The FPO is measured using an impactor or impinger, such as a twin stage impinger (TSI), multi-stage liquid impinger (MSLI), Andersen Cascade Impactor (ACI) or a NGI. Each impactor or impinger has a pre-determined aerodynamic particle size collection cut-off point for each stage. The FPO value is obtained by interpretation of the stage-by-stage active agent recovery quantified by a validated quantitative wet chemical assay where either a simple stage cut is used to determine FPO or a more complex mathematical interpolation of the stage-by-stage deposition is used.

Fine Particle Fraction

"Fine particle fraction" or "FPF" as used herein is normally defined as the FPO divided by the ED and expressed as a percentage. Herein, the FPF of ED is referred to as FPF(ED) and is calculated as FPF(ED)=(FPO/ED)×100%. "Fine Particle Fraction" may also be defined as the FPO divided by the MD and expressed as a percentage. Herein, the FPF of MD is referred to as FPF(MD), and is calculated as FPF(MD)=(FPO/MD)×100%. Specific FPF values cited herein are to be understood as achieved by testing 25 mg of powder within a size 3 HPMC capsule delivered from a Monohaler Dry Powder Inhaler Device tested using a NGI set at 90 L/minute for 2.67 seconds, to achieve a 4 kPa pressure drop across the mouthpiece.

Ambient Conditions

"Ambient conditions" as used herein are defined as 22° C.±5° C. and 40-50% RH. The terms "ambient temperature" and "ambient humidity" as used herein are defined as 22° C.±5° C. and 40-50% RH respectively.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

While certain embodiments of the present invention are described in detail above, the scope of the invention is not to be considered limited by such disclosure, and modifications are possible without departing from the spirit of the invention as evidenced by the examples and claims.

EXAMPLES

Selected embodiments of the present invention will now be explained with reference to the examples. It will be apparent to those skilled in the art from this disclosure that the following descriptions of the embodiments are for illustration only and not for the purpose of limiting the invention as defined by the appended claims and their equivalents.

The examples below illustrate how micronised drug particles may be conditioned, in order to reduce the surface non-crystalline material present.

Control Formulation 0 (Glycopyrrolate Only)

Figure 1:
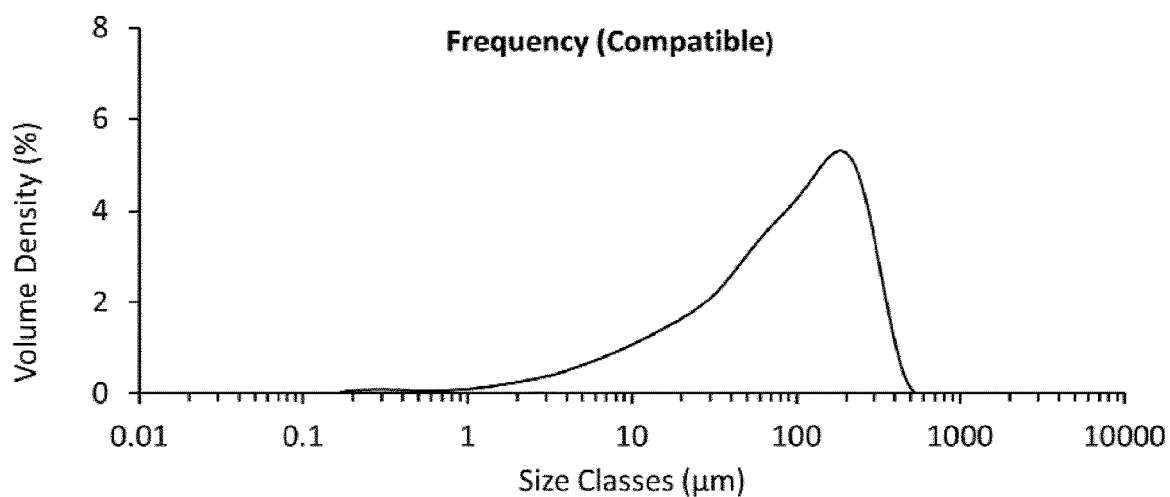
FIG. 1 shows the particle size distribution for unmicronised glycopyrrolate which has been stored under sealed conditions, $D_{10}$=11.3 µm, $D_{50}$=98.0 µm, $D_{90}$=281 µm. The cumulative fraction under 5 µm was 4.68%.

The particle size distribution for unmicronised glycopyrrolate was determined by MALVERN MASTERSIZER analysis (MALVERN MASTERSIZER® 3000, using the Aero S dry dispersion method at 4 Bar) and found to be $D_{10}=11.3$ μm, $D_{50}=98.0$ μm, $D_{90}=281$ μm (see FIG. 1).

Figure 2:
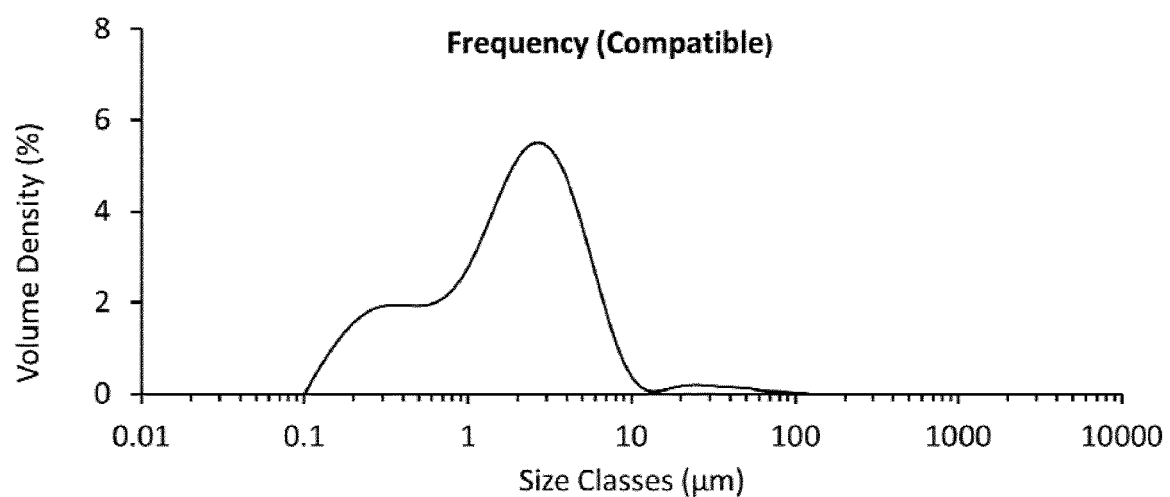
FIG. 2 shows the particle size distribution for freshly jet milled glycopyrrolate only, the cumulative fraction under 5 µm was 85.75%.

A 25 g sample from the same batch of unmicronised glycopyrrolate was added to the powder inlet of an AS-50 spiral jet mill (Inlet pressure=5 Bar, Grinding Pressure=3 Bar, Averaged Feed Rate=2 g/min) using air having a humidity below 20% RH and the jet milled glycopyrrolate was recovered from a bag filter with a 0.2 μm pore size. The particle size distribution for this freshly micronised glycopyrrolate was determined as above and found to be $D_{10}=0.315$ μm, $D_{50}=2.05$ μm, $D_{90}=5.81$ μm (see FIG. 2) with a cumulative fraction under 5 μm of 85.75%.

This freshly micronised glycopyrrolate was tipped out as a compact heap of powder and the heap of powder was exposed to 40° C. at 75% RH for 1 hour on a tray thereby preventing the conditioning environment from reaching the internal particles in the heap of powder. The particle size distribution for freshly micronised glycopyrrolate was determined as above and found to be $D_{10}=88.4$ μm, $D_{50}=389$ μm, $D_{90}=963$ μm (see FIG. 3) with a cumulative fraction under 5 μm of 1.44%.

Formulation 1 (Glycopyrrolate Only; 25° C. at 60% RH) and Formulation 2

(Glycopyrrolate and magnesium stearate (95:5 w/w); 25° C. at 60% RH) Unmicronised glycopyrrolate 25 g ($D_{10}=11.3$ μm, $D_{50}=98.0$ μm, $D_{90}=281$ μm) (see FIG. 1) was added to the powder inlet of an AS-50 spiral jet mill (Inlet pressure=5 Bar, Grinding Pressure=3 Bar, Averaged Feed Rate=2 g/min) using air having a humidity below 20% RH and the jet milled glycopyrrolate was recovered from a bag filter with a 0.2 μm pore size. Formulation 2 was produced as above for Formulation 1 but instead used glycopyrrolate and magnesium stearate (95:5 w/w) which was pre-blended in a glass beaker using a metal spatula for 30 seconds before co-micronization.

The particle size distributions for Formulation 1 ($D_{10}=0.283$ μm, $D_{50}=1.66$ μm, $D_{90}=5.40$ μm) and Formulation 2 ($D_{10}=0.270$ μm, $D_{50}=1.41$ μm, $D_{90}=3.66$ μm were determined by MALVERN MASTERSIZER® analysis (MALVERN MASTERSIZER® 3000, using the Aero S dry dispersion method at 4 Bar). These are reported in FIGS. 4 and 8 respectively and Table 1 below.

Figure 27:
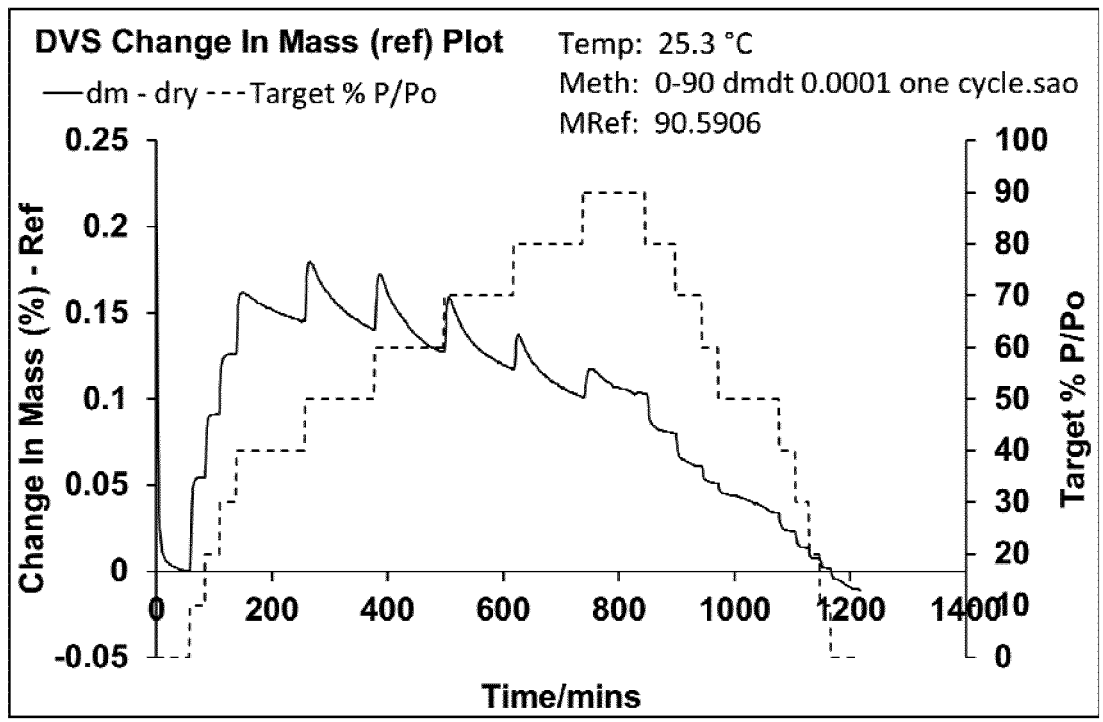
Figure 29:
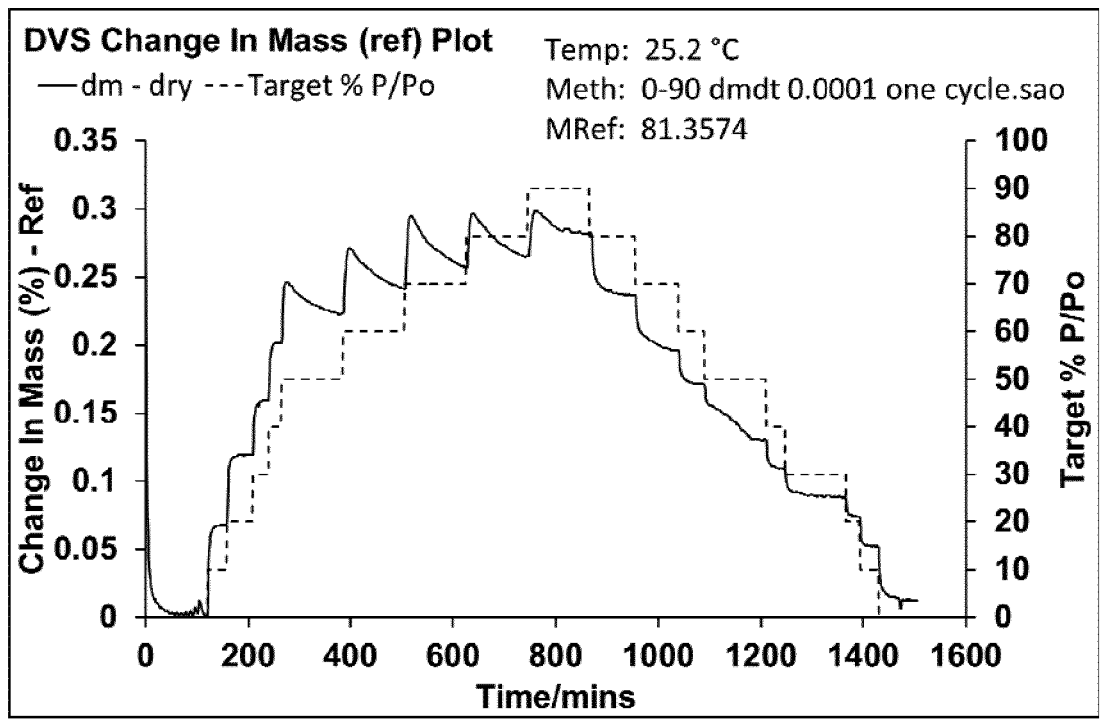

The presence of amorphous material for the milled or co-jet milled glycopyrrolate (t=0) was determined by DVS and are reported in FIG. 27 (Formulation 1) and FIG. 29 (Formulation 2).

A stability cabinet (Vin don Scientific, 5600S, Serial Number 167 43) was prepared and equilibrated at 25° C. at 60% RH. Once micronized, the glycopyrrolate was immediately subjected to a post-micronisation treatment by ensuring the particles were equally exposed to these conditions. Humidity levels were monitored for the duration of the equilibration and conditioning process by using an electronic tiny tag placed within the stability cabinet.

The milled glycopyrrolate (Formulation 1) and co-jet milled glycopyrrolate and magnesium stearate (Formulation 2) were conditioned by exposure to 25° C. at 60% RH for 71 hours, with samples being taken at intervals indicated in Table 2 and set aside in sealed vials for analysis at 72 hours post milling. During conditioning the powder bed was regularly moved by raking with a metal spatula.

The particle size distributions for the conditioned samples were determined by MALVERN MASTERSIZER® analysis (as above) and are reported in FIGS. 5, 6, 7, 9, 10 and 11, and in Tables 1 and 2 below.

Figure 28:
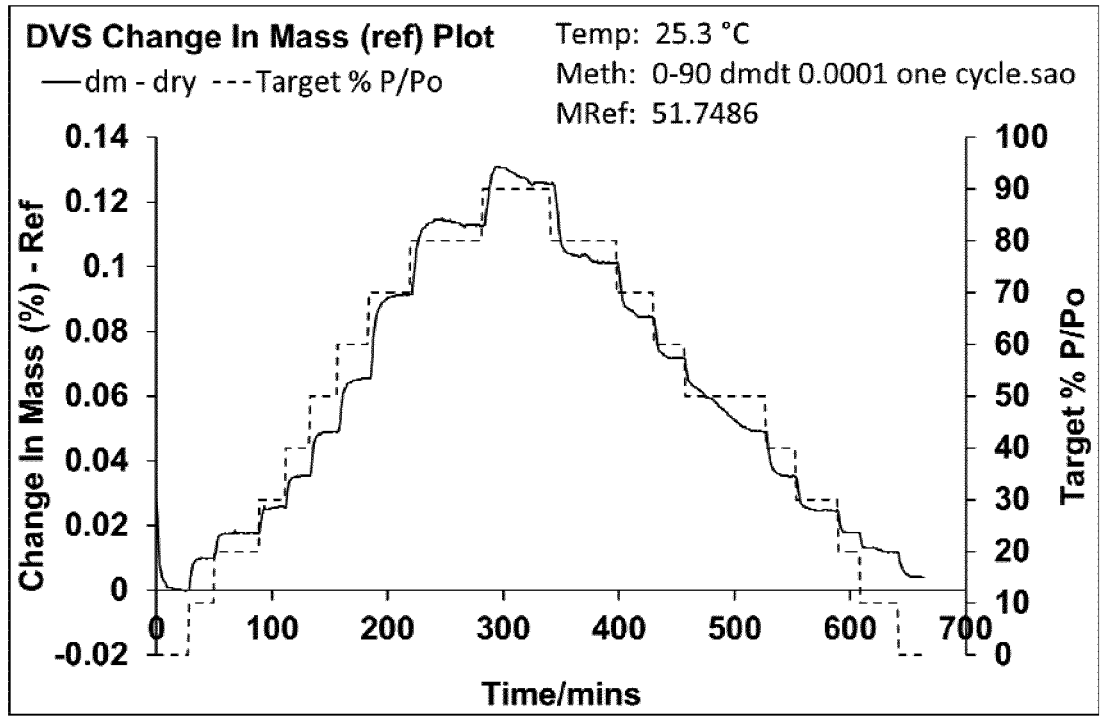
Figure 30:
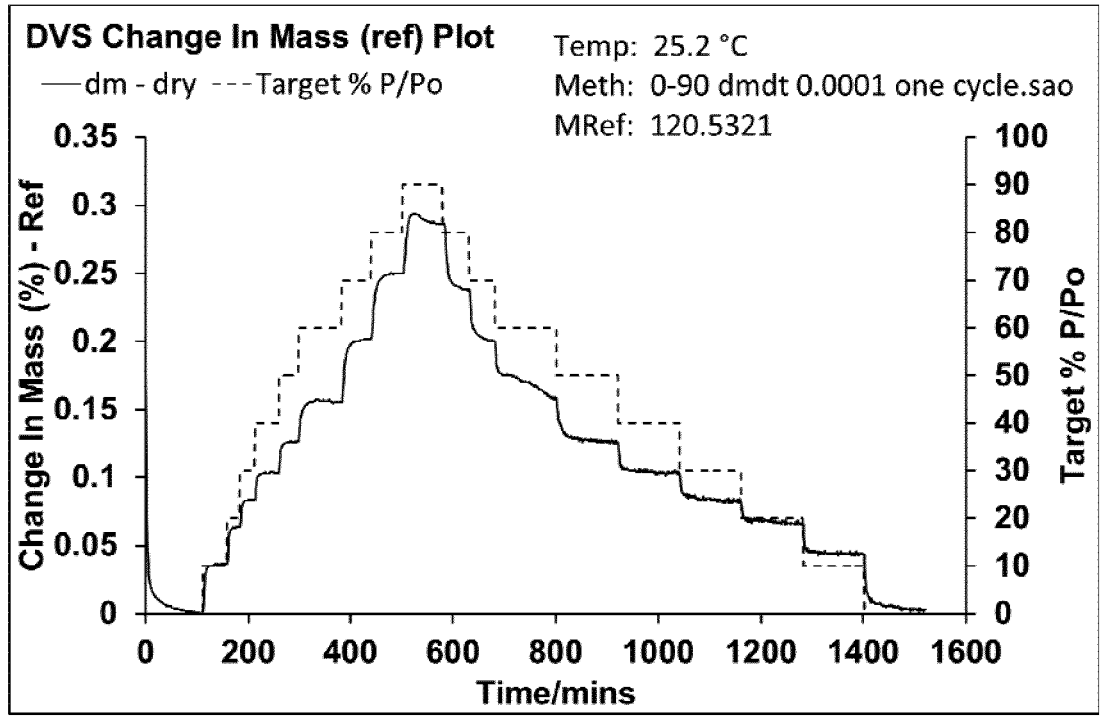

The presence of amorphous material for the conditioned glycopyrrolate or co-jet milled glycopyrrolate (t=49 hrs) was determined by DVS, reported in FIGS. 28 and 30.

Formulation 3 (Glycopyrrolate Only; 50° C. at 50% RH) and Formulation 4 (Glycopyrrolate and Magnesium Stearate (95:5 w/w); 50° C. at 50% RH)

Unmicronised glycopyrrolate 15 g ($D_{10}=11.3$ μm, $D_{50}=98.0$ μm, $D_{90}=281$ μm) was added to the powder inlet of an AS-50 spiral jet mill (Inlet pressure=5 Bar, Grinding Pressure=3 Bar, Averaged Feed Rate=2 g/min) using air having a humidity below 20% RH and the jet milled glycopyrrolate was recovered from a bag filter with a 0.2 μm pore size. Formulation 4 was produced as above for Formulation 3 but instead used glycopyrrolate and magnesium stearate (95:5 w/w) which was pre-blended in a glass beaker using a metal spatula for 30 seconds before co-micronization.

The particle size distributions for Formulation 3 ($D_{10}=0.283$ μm, $D_{50}=1.75$ μm, $D_{90}=7.41$ μm) Formulation 4 ($D_{10}=0.266$ μm, $D_{50}=1.22$ μm, $D_{90}=3.07$ μm) were determined by MALVERN MASTERSIZER® analysis (as above) and are reported in FIGS. 17 and 19, and in Table 1 below.

The stability cabinet was prepared and equilibrated at 50° C. at 50% RH. Once micronized, the glycopyrrolate or the co-jet milled glycopyrrolate was immediately(<5 minutes) subjected to a post-micronisation treatment by ensuring the particles were equally exposed to these conditions. Humidity levels were monitored for the duration of the equilibration and conditioning process as above.

The milled glycopyrrolate (Formulation 3) and co-jet milled glycopyrrolate (Formulation 4) were each conditioned by exposure to 50° C. at 50% RH for at least 49 hrs. The powder bed was regularly moved by raking with a metal spatula. After 49 hrs, samples of the conditioned glycopyrrolate and co-jet milled glycopyrrolate were recovered for analysis.

The particle size distributions (t=49 hrs) were determined by MALVERN MASTERSIZER® analysis as above ($D_{10}$=1.94 µm, $D_{50}$=16.5 µm, $D_{90}$=327 µm for Formulation 3 and $D_{10}$=0.437 µm, $D_{50}$=3.74 µm, $D_{90}$=269 µm for Formulation 4) and are reported in FIGS. 18 and 20, and Table 1 below.

Figure 31:
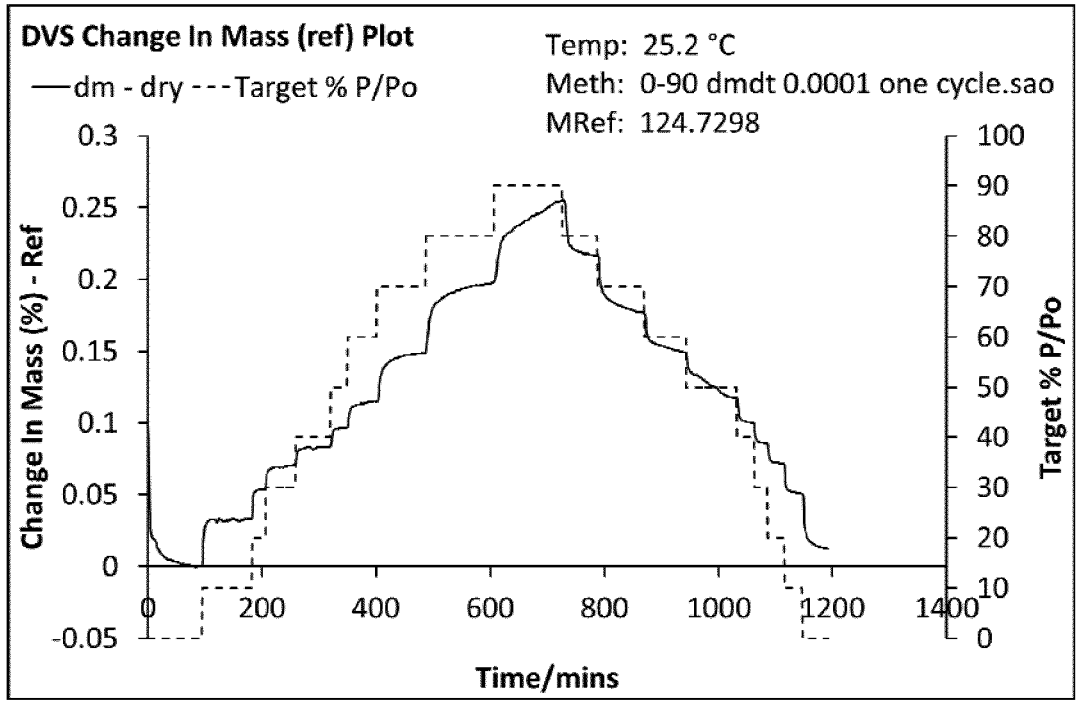

The presence of amorphous material for the conditioned co-jet milled glycopyrrolate (t=49 hrs) was determined by OVS, reported in FIG. 31.

Formulation 5 (Glycopyrrolate Only; 6° C. at 86% RH) and Formulation 6 (Glycopyrrolate and Magnesium Stearate (95:5 w/w); 6° C. at 86% RH)

Unmicronised glycopyrrolate 15 g ($D_{10}$=11.3 µm, $D_{50}$=98.0 µm, $D_{90}$=281 µm) was added to the powder inlet of an AS-50 spiral jet mill (Inlet pressure=5 Bar, Grinding Pressure=3 Bar, Averaged Feed Rate=2 g/min) using air having a humidity below 20% RH and the jet milled glycopyrrolate was recovered from a bag filter with a 0.2 µm pore size. Formulation 6 was produced as above for Formulation 5 but instead used glycopyrrolate and magnesium stearate (95:5 w/w) which was pre-blended in a glass beaker using a metal spatula for 30 seconds before co-micronization.

The particle size distribution for Formulation 5 (reported as $D_{10}$=96.7 µm, $D_{50}$=569 µm, $D_{90}$=1580 µm) and Formulation 6 ($D_{10}$=0.276 µm, $D_{50}$=1.52 µm, $D_{90}$=3.97 µm) for the milled glycopyrrolate (t=0) was determined by MALVERN MASTERSIZER analysis as above and are reported in FIGS. 21 and 23, and Table 1 below.

A refrigerator was prepared and equilibrated at 6° C. at 86% RH. Once micronized, the glycopyrrolate or the co-jet milled glycopyrrolate was immediately(<5 minutes) subjected to a post-micronisation treatment by ensuring the particles were equally exposed to these conditions. Humidity levels were monitored for the duration of the equilibration and conditioning process as above.

The milled and co-jet milled glycopyrrolate was conditioned by exposure to 6° C. at 86% RH for 49 hrs. The powder bed was regularly moved by raking with a metal spatula. After 49 hrs, samples of the conditioned glycopyrrolate were recovered for analysis.

The particle size distribution for Formulation 5 (reported as $D_{10}$=0.410 µm, $D_{50}$=3.03 µm, $D_{90}$=253 µm) and Formulation 6 (reported as $D_{10}$=0.314 µm, $D_{50}$=2.01 µm, $D_{90}$=70.8 µm) for the Conditioned glycopyrrolate (t=49 hrs) was determined by MALVERN MASTERSIZER® analysis as above and reported in FIG. 22 (Formulation 5), FIG. 24 (Formulation 6) and Table 1 below.

Figure 32:
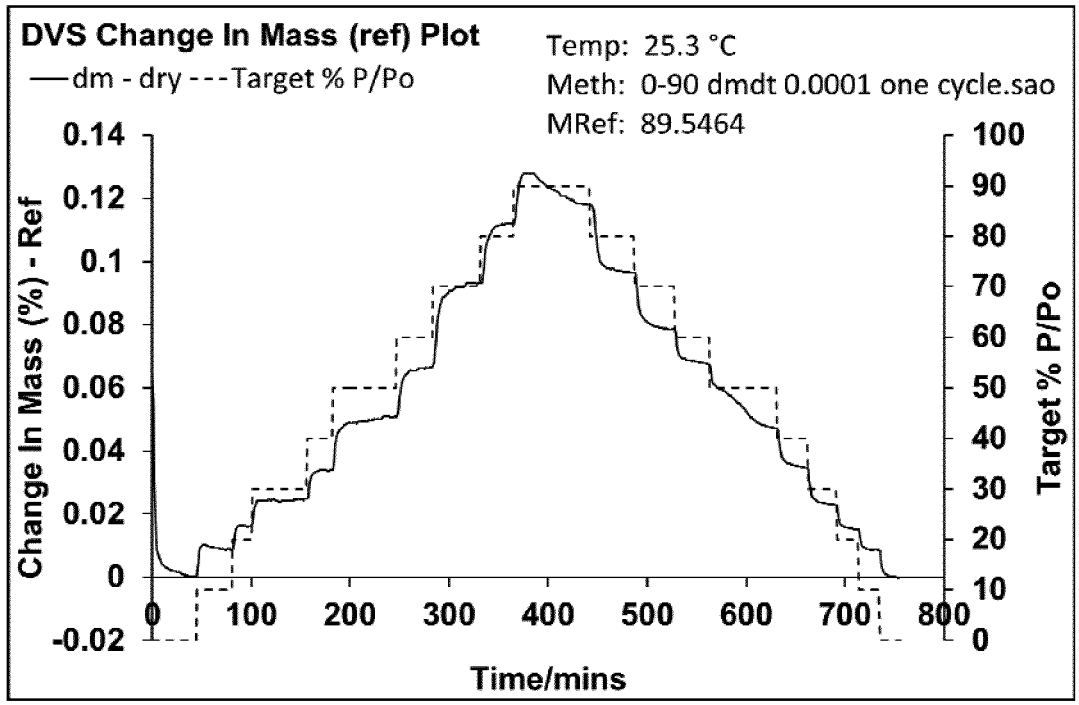
Figure 33:
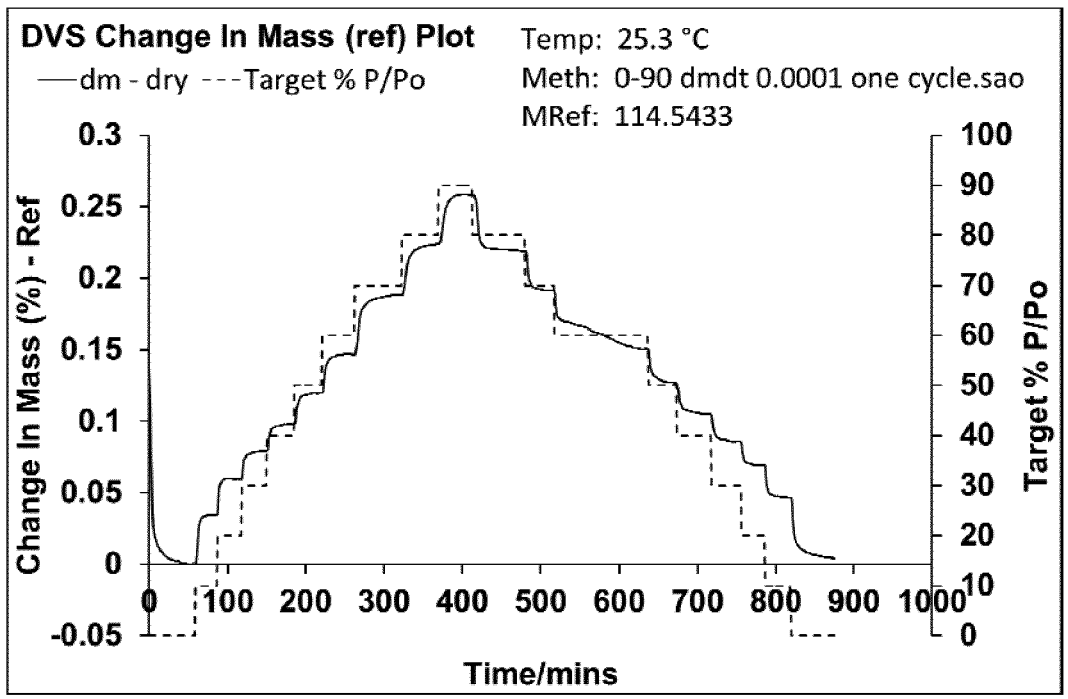

The presence of amorphous material for the conditioned glycopyrrolate (t=49 hrs) was determined by OVS and reported in FIGS. 32 and 33 for Formulations 5 and 6 respectively.

Formulation 7 (Glycopyrrolate and magnesium stearate (95:5 w/w); 24° C. at 45% RH) 15 g of unmicronised glycopyrrolate ($D_{10}$=11.3 µm, $D_{50}$=98.0 µm, $D_{90}$=281 µm) was pre-blended with magnesium stearate in a glass beaker using a metal spatula for 30 seconds before micronization in an AS-50 spiral jet mill (Inlet pressure=5 Bar, Grinding Pressure=3 Bar, Averaged Feed Rate=2 g/min) using air having a humidity below 20% RH and the co-jet milled glycopyrrolate was recovered from a bag filter with a 0.2 µm pore size.

The co-jet milled glycopyrrolate was conditioned by exposure to ambient laboratory conditions (24° C.±3° C. at 45% RH±5% RH for 72 hrs by emptying the micronized powder from the jet mill onto a stainless steel tray. The powder bed was not agitated at all during this time. After 72 hrs, a sample of the glycopyrrolate was recovered.

The particle size distribution (reported as $D_{10}$=0.272 µm, $D_{50}$=1.53 µm, $D_{90}$=3.96 µm) for the conditioned glycopyrrolate was determined by MALVERN MASTERSIZER® analysis as above and reported in FIG. 25 and Table 1 below.

Figure 34:
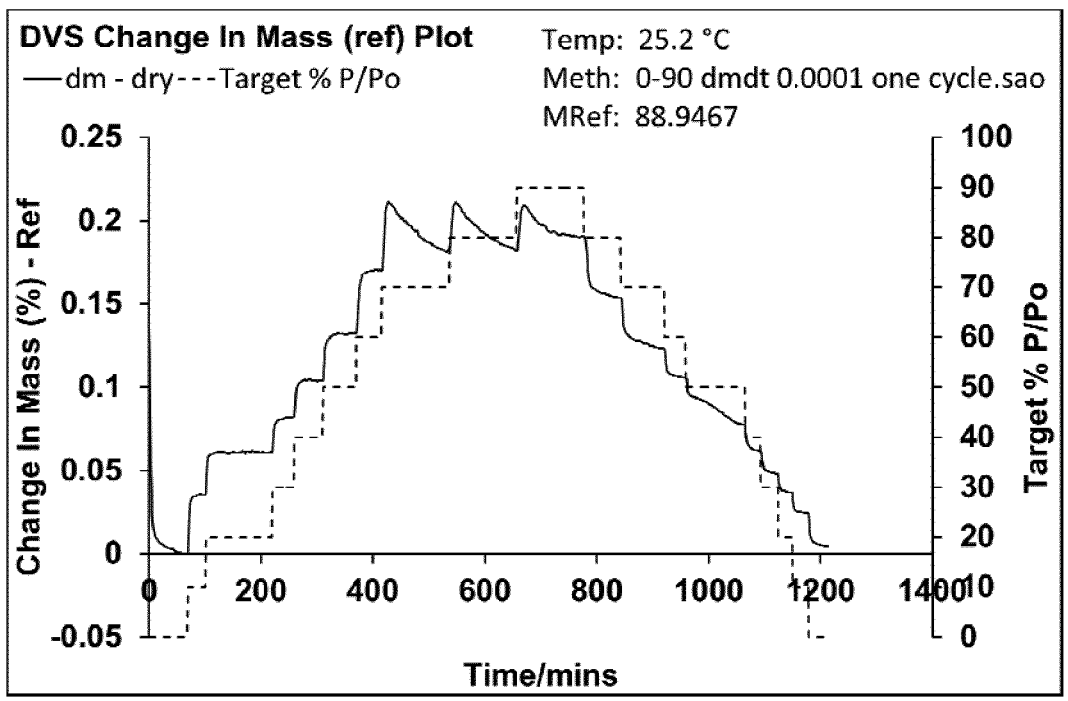

The presence of amorphous material for the conditioned co-jet milled glycopyrrolate was determined by OVS and reported in FIG. 34 below.

Formulation 8 (Glycopyrrolate and Magnesium Stearate (95:5 w/w); 24° C. at 45% RH; Open Glass Vial)

25 g of unmicronised glycopyrrolate ($D_{10}$=11.3 µm, $D_{50}$=98.0 µm, $D_{90}$=281 µm) was pre-blended with magnesium stearate in a glass beaker using a metal spatula for 30 seconds before micronization in an AS-50 spiral jet mill (Inlet pressure=5 Bar, Grinding Pressure=3 Bar, Averaged Feed Rate=2 g/min) using air having a humidity below 20% RH and the co-jet milled glycopyrrolate was recovered from a bag filter with a 0.2 µm pore size.

The particle size distributions (reported as $D_{10=0.270}$ µm, $D_{50}$=1.41 µm, $D_{90}$=3.66 µm) for the co-jet milled glycopyrrolate (t=0) were determined by MALVERN MASTERSIZER® analysis as above and reported in FIG. 8 and Table 1 below.

A sample of the co-jet milled glycopyrrolate (approximately 5 g) was conditioned by exposure to ambient laboratory conditions (24° C.±3° C. at 45% RH±5% RH) for 144 hrs in an un-sealed glass vial. The powder bed was not agitated at all during this time. After 144 hrs, a sample of the conditioned co-jet milled glycopyrrolate was recovered.

The particle size distribution (reported as $D_{10}$=0.289 µm, $D_{50}$=1.70 µm, $D_{90}$=8.73 µm) for the conditioned co-jet milled glycopyrrolate was determined by MALVERN MASTERSIZER® analysis as above and reported in FIG. 26 and Table 1 below.

Figure 35:
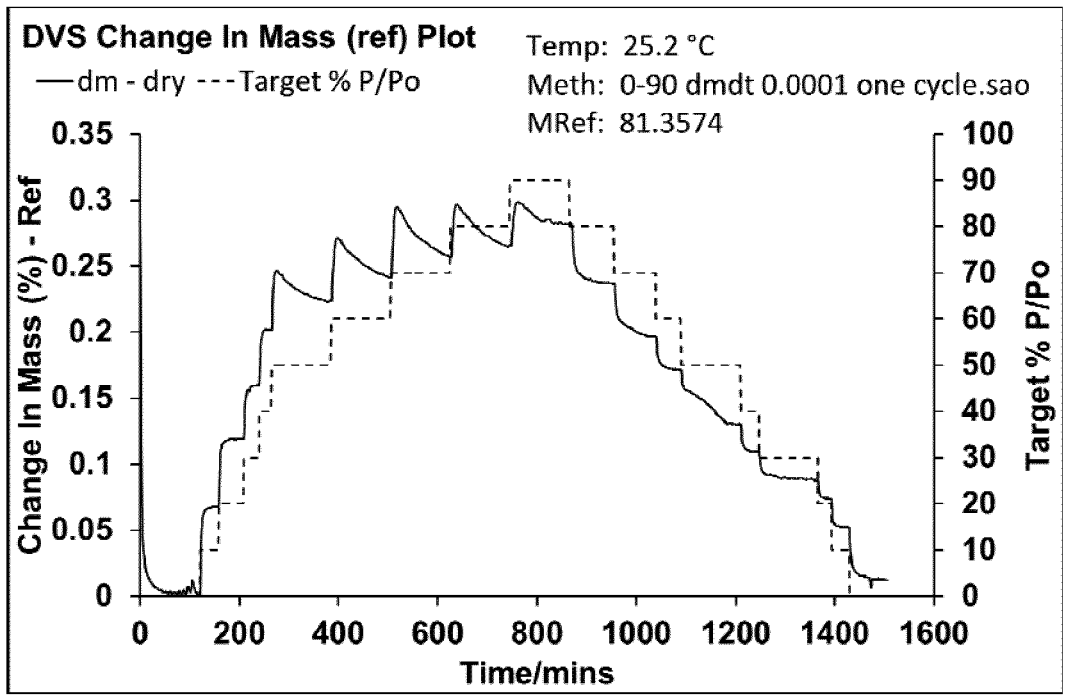
Figure 36:
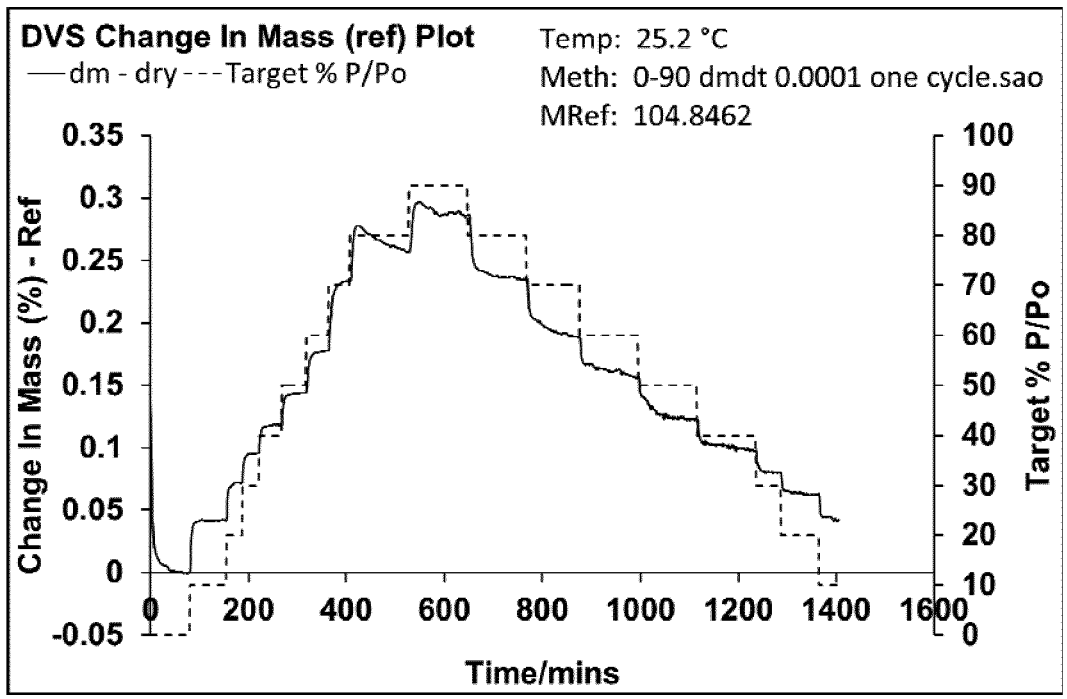

The presence of amorphous material for the t=0 and conditioned co-jet milled glycopyrrolate samples was determined by OVS and reported in FIGS. 35 and 36 respectively.

Formulation 9 (Co-Micronised Glycopyrrolate and Magnesium Stearate (95:5 w/w) then Immediately Blended with Lactose then FPF Performance)

To illustrate the improvement of the invention disclosed by Formulation 10, the following control formulation can made as follows:

25 g of unmicronised glycopyrrolate are pre-blended with magnesium stearate (95:5) in a glass beaker using a metal spatula for 30 seconds before micronization in an AS-50 spiral jet mill (Inlet pressure=5 Bar, Grinding Pressure=3 Bar, Averaged Feed Rate=2 g/min) using air having a humidity below 20% RH and the co-jet milled glycopyrrolate is recovered from a bag filter with a 0.2 µm pore size.

Lactohale® 100 lactose carrier particles (49.85 g) is immediately admixed with the co-jet milled glycopyrrolate and magnesium stearate (0.15 g) using a Diosna (250 ml) at 1000 rpm for 10 minutes to give an inhalable dry powder.

The resulting inhalable dry powder is filled into size 3 HPMC capsules in 25 mg aliquots.

Formulation 10 (Co-Micronised Glycopyrrolate and Magnesium Stearate (95:5 w/w) then Immediately Conditioned then Blended with Lactose then Assessed for FPF Performance)

A sample (20 g) from the co-jet milled glycopyrrolate and magnesium stearate (t=0) formulation produced in Example 9 (i.e. the formulation before Lactohale® 100 lactose carrier particles are added) is subjected to a conditioning process.

A stability cabinet (Vindon Scientific, 5600S, Serial Number 16743) is prepared and equilibrated at 25° C. at 60% RH. Once micronized, the co-jet milled glycopyrrolate and magnesium stearate sample is immediately subjected to a post-micronisation treatment by ensuring the particles are equally exposed to these conditions. Humidity levels are monitored for the duration of the equilibration and conditioning process by using an electronic tiny tag placed within the stability cabinet.

The co-jet milled glycopyrrolate is conditioned by exposure to 25° C. at 60% RH. Samples (0.15 g) of this co-jet milled glycopyrrolate and magnesium stearate undergoing conditioning are removed after 30 minutes, 1 hour, 2 hours, 3 hours, 4 hours, 5 hours, 24 hours and 48 hours and admixed with Lactohale® 100 lactose carrier particles (49.85 g) μm) using a Diosna (250 ml) at 1000 rpm for 10 minutes to give an inhalable dry powder.

The resulting inhalable dry powders are filled into size 3 HPMC capsules in 25 mg aliquots.

Formulation 11 (Co-Milled Glycopyrrolate Magnesium Stearate (95:5 w/w) then Conditioned at 25° C. at 60% RH on a Steel Tray (No Agitation) for 1 hr then Blended with Lactose)

To illustrate the improvement of the invention, the following control formulation can be made using an alternate milling technique as follows:

25 g of unmicronised glycopyrrolate is pre-blended with magnesium stearate (95:5) in a glass beaker using a metal spatula for 30 seconds before co-milling with a knife mill (rotor speed=1500 rpm, duration=10 minutes) and the co-milled glycopyrrolate and magnesium stearate is recovered from the co-milling chamber.

A stability cabinet (Vindon Scientific, 5600S, Serial Number 16743) is prepared and equilibrated at 25° C. at 60% RH. The co-milled glycopyrrolate and magnesium stearate is immediately subjected to a post-milling treatment by ensuring the particles are equally exposed to these conditions. Humidity levels are monitored for the duration of the equilibration and conditioning process by using an electronic tiny tag placed within the stability cabinet.

The powder bed is not agitated.

The co-milled glycopyrrolate and magnesium stearate are conditioned by exposure to 25° C. at 60% RH for 5 minutes to at least 49 hrs, and set aside in sealed vials for analysis at 72 hours post milling.

Formulation 12 (Co-Micronised Glycopyrrolate Magnesium Stearate (95:5 w/w) then Stored Under Desiccated Environment 25° C. at 0% RH (No Agitation) then Blended with Lactose)

25 g of unmicronised glycopyrrolate is pre-blended with magnesium stearate in a glass beaker using a metal spatula for 30 seconds before microfuge in an AS-50 spiral jet mill (Inlet pressure=5 Bar, Grinding Pressure=3 Bar, Averaged Feed Rate=2 g/min) using air having a humidity below 20% RH and the co-jet milled glycopyrrolate is recovered from a bag filter with a 0.2 μm pore size.

Once micronized, the co-jet milled glycopyrrolate and magnesium stearate is immediately subjected to a post-micronization treatment which involved placing the powder on a tray under in a sealed chamber containing the desiccant phosphorous pentoxide in excess. The co-jet milled glycopyrrolate and magnesium stearate and phosphorous pentoxide are not combined.

The sealed chamber is at 25° C. with 0-5% RH whilst ensuring the particles are equally exposed to these conditions for the duration of this treatment. Humidity levels are monitored for the duration of the chamber equilibration and treatment process by using an electronic tiny tag placed within the stability cabinet.

The powder bed is not agitated.

Control Experiment: Formulation 12a

Lactohale® 100 lactose carrier particles (49.85 g) are immediately admixed with a sample of the treated co-jet milled glycopyrrolate and magnesium stearate (0.15 g) using a Diosna (250 ml) at 1000 rpm for 10 minutes to give an inhalable dry powder.

The resulting inhalable dry powder is filled into size 3 HPMC capsules in 25 mg aliquots.

Formulation 12b

Once the sample of the treated (desiccated) co-jet milled glycopyrrolate and magnesium stearate is taken for Formulation 12a, the remaining treated co-jet milled glycopyrrolate and magnesium stearate (Formulation 12b) is subjected to conditioning.

A stability cabinet (Vindon Scientific, 5600S, Serial Number 16743) is prepared and equilibrated at 25° C. at 60% RH. Humidity levels are monitored for the duration of the equilibration and conditioning process by using an electronic tiny tag placed within the stability cabinet.

The treated (desiccated) co-jet milled glycopyrrolate and magnesium stearate (Formulation 12b) is conditioned by exposure to 25° C. at 60% RH for 71 hours, with samples being taken at regular intervals and these samples are set aside in sealed vials for analysis at 72 hours from commencement of the conditioning process. During conditioning the powder bed is regularly moved by raking the powder bed with a metal spatula.

Lactohale® 100 lactose carrier particles (49.85 g) are immediately admixed with samples of the now conditioned co-jet milled glycopyrrolate and magnesium stearate (0.15 g) using a Diosna (250 ml) at 1000 rpm for 10 minutes to give an inhalable dry powder.

The resulting inhalable dry powder is filled into size 3 HPMC capsules in 25 mg aliquots.

Summary Data (Starting PSDs)

TABLE 1

| Particle size (μm) distributions | | | | |
|---|---|---|---|---|
| | D10 (μm) | D50 (μm) | D90 (μm) | Volume <5 (μm) (%) |
| Formulation 1 (t = 0 hrs) | 0.283 | 1.66 | 5.40 | 88.56 |
| Formulation 1 (t = 4 hrs)* | 0.410 | 3.10 | 475 | 64.33 |
| Formulation 2 (t = 0 hrs) | 0.270 | 1.41 | 3.66 | 95.63 |
| Formulation 2 (t = 0 hrs)* | 0.308 | 1.87 | 69.6 | 82.35 |
| Formulation 3 (t = 0 hrs) | 0.283 | 1.75 | 7.41 | 84.53 |
| Formulation 3 (t = 49 hrs) | 1.940 | 16.5 | 327 | 32.77 |
| Formulation 4 (t = 0 hrs) | 0.266 | 1.22 | 3.07 | 98.45 |
| Formulation 4 (t = 49 hrs) | 0.437 | 3.74 | 269 | 54.44 |
| Formulation 5 (t = 0 hrs) | 96.7 | 569 | 1580 | 5.26 |
| Formulation 5 (t = 49 hrs)* | 0.410 | 3.03 | 253 | 64.27 |
| Formulation 6 (t = 0 hrs) | 0.276 | 1.52 | 3.97 | 94.88 |
| Formulation 6 (t = 49 hrs) | 0.314 | 20.1 | 70.8 | 81.08 |
| Formulation 7 (t = 0 hrs) | Not done | Not done | Not done | Not done |

TABLE 1-continued

Particle size (μm) distributions

|  | D10 (μm) | D50 (μm) | D90 (μm) | Volume <5 (μm) (%) |
|---|---|---|---|---|
| Formulation 7 (t = 72 hrs) | 0.272 | 1.53 | 3.96 | 94.91 |
| Formulation 8 (t = 0 hrs) | 0.270 | 1.41 | 3.66 | 95.63 |
| Formulation 8 (t = 144 hrs) | 0.289 | 1.70 | 8.73 | 86.94 |

*= Analysis at 72 hrs from Jet/ co-jet milling.

TABLE 2

Particle size (μm) distributions for Formulation 1 and Formulation 2 for the period 5 minutes to 4260 minutes (71 hrs) conditioning

| | Formulation 1 | | | | Formulation 2 | | | |
|---|---|---|---|---|---|---|---|---|
| Time (Minutes/hrs) | D10 (μm) | D50 (μm) | D90 (μm) | Span | D10 (μm) | D50 (μm) | D90 (μm) | Span |
| 5 | 0.602 | 4.38 | 791 | 180.5 | 1.05 | 186 | 1230 | 6.6 |
| 10 | 0.468 | 3.61 | 659 | 182.4 | 0.601 | 42.7 | 859 | 20.1 |
| 15 | 0.415 | 3.14 | 493 | 156.9 | 0.437 | 3.42 | 662 | 193.4 |
| 20 | 0.392 | 2.9 | 394 | 135.7 | 0.643 | 51.6 | 859 | 16.6 |
| 30 | 0.404 | 3.05 | 480 | 157.2 | 0.501 | 4.82 | 847 | 175.6 |
| 45 | 0.409 | 3.14 | 530 | 168.7 | 0.471 | 3.98 | 731 | 183.6 |
| 60 (1) | 0.405 | 3.06 | 507 | 165.6 | 0.341 | 2.23 | 345 | 154.6 |
| 90 (1.5) | 0.410 | 3.11 | 500 | 160.6 | 0.292 | 1.73 | 20.2 | 11.5 |
| 120 (2) | 0.413 | 3.18 | 536 | 168.4 | 0.315 | 2.00 | 104 | 51.8 |
| 150 (2.5) | 0.416 | 3.20 | 529 | 165.2 | 0.294 | 1.71 | 44.2 | 25.7 |
| 180 (3) | 0.410 | 3.13 | 502 | 160.3 | 0.291 | 1.68 | 46.7 | 27.6 |
| 240 (4) | 0.396 | 2.98 | 422 | 141.5 | 0.299 | 1.72 | 148 | 85.9 |
| 300 (5) | 0.404 | 3.05 | 451 | 147.7 | 0.279 | 1.52 | 3.70 | 2.3 |
| 360 (6) | 0.402 | 3.06 | 451 | 147.3 | 0.28 | 1.59 | 4.16 | 2.4 |
| 1440 (24) | 0.421 | 3.22 | 515 | 159.8 | 0.286 | 1.65 | 5.11 | 2.9 |
| 1560 (26) | 0.415 | 3.16 | 495 | 156.5 | 0.298 | 1.77 | 63.8 | 35.9 |
| 1680 (28) | 0.429 | 3.29 | 568 | 172.5 | 0.33 | 2.03 | 349 | 171.8 |
| 1800 (30) | 0.432 | 3.33 | 568 | 170.4 | 0.305 | 1.79 | 28.1 | 15.5 |
| 2940 (49) | 0.410 | 3.10 | 475 | 153.1 | 0.308 | 1.87 | 69.6 | 37.1 |
| 3120 (52) | 0.424 | 3.26 | 552 | 169.2 | 0.289 | 1.68 | 5.73 | 3.2 |
| 4260 (71) | 0.415 | 3.16 | 497 | 157.1 | 0.295 | 1.7 | 5.17 | 2.9 |

Discussion: Formulations 0-8

Freshly micronized glycopyrrolate is inhalable (see FIG. 2 and FIG. 4) but possesses significant amounts of amorphous material (see FIG. 27) which results in agglomerated non-inhalable glycopyrrolate if not conditioned (see FIG. 3). To demonstrate this phenomenon, Formulations 0 was jet milled and then tipped out as a compact heap of powder. The heap of micronized glycopyrrolate was not conditioned but instead the compact heap was exposed to 40° C. at 75% RH for 1 hour on a tray. The physical arrangement of the powder as a heap prevented conditioning of the internal micronized particles leaving intrinsic moisture within the heap of micronized glycopyrrolate to cause rapid recrystallisation and agglomeration as shown by a PSO of $D_{10}$=88.4 μm, $D_{50}$=389 μm and $D_{90}$=963 μm. The initial particle size distributions (t=0) of freshly micronized glycopyrrolate have a significant volume of the particles below 5 μm (see Formulations 1, 3 and 5). In contrast, co-jet milled formulations according to the invention have even better initial particle size distributions (t=0) (see Formulations 2, 4, 6 and 8). These superior particle size distributions for Formulations 2, 4, 6, 7 and 8 are retained after conditioning which includes exposure of the co-jet milled glycopyrrolate and magnesium stearate to humidity at temperatures between 5° C. to 88° C. for at least 60 minutes.

Formulations 1, 2, 3, 4, 5, 6, 7 and 8 were prepared using various conditioning parameters and all have significant amounts of inhalable glycopyrrolate (>30% by volume of the formulation is less than 5 μm). The conditioning parameters comprised temperature ranges from 6° C. to 50° C. and humidity ranges from 50% to 86% RH. Formulations 2, 4, 6, 7 and 8 according to the invention have better results than Formulations 1, 3 and 5.

The $D_{90}$, $D_{50}$ and $D_{10}$ traces for Formulations 1 and 2 provide greater detail of the superior product obtained when co-jet milled glycopyrrolate is conditioned by exposing the co-jet milled (glycopyrrolate and anti-adherent agent to humidity at a temperature of 25° C. and relative humidity of 60% RH for at least 60 minutes. FIG. 12 shows that Formulation 1 (glycopyrrolate only) started with a high $D_{90}$ of 791 μm but this rapidly reduces to 394 μm after 20 minutes of conditioning and the $D_{90}$ remains within this range for the remaining conditioning period. In contrast, Formulation 2 (co-jet milled glycopyrrolate and magnesium stearate) started with a higher $D_{90}$ of 1230 μm which had only reduced to 859 μm after 20 minutes and remains above Formulation 1 until 60 minutes of conditioning. From this we can conclude that Formulation 1 achieved a stable $D_{90}$ much more quickly than Formulation 2. Without wishing to be bound by theory, it is thought that the magnesium stearate retards the conditioning process as demonstrated by FIG. 12. Surprisingly, however the $D_{90}$ for Formulation 2 continues to decrease well below that of Formulation 1 achieving a $D_{90}$ which is only 4% that of Formulation 1's $D_{90}$ after 90 minutes. The $D_{90}$ for Formulation 2 continues to remain significantly below that of Formulation 1 for the remaining conditioning process. Conditioned particles are crystalline and physically stable; consequently the $D_{90}$ for post-conditioned Formulations 1 and 2 will continue to remain distinguishable.

Similarly, the $D_{90}$ and 0 10 values for Formulation 2 are also superior compared with Formulation 1 after 60 minutes of conditioning; the traces never again cross indicating that it is possible to distinguish between a "milled and conditioned product" and a "co-jet milled and conditioned product" based upon particle size distributions (see FIGS. 13, 14, 15 and 16).

The t=0 sample which was taken from Formulation 5 for analysis had an initial cumulative fraction under 5 μm which was only 5.26% and much lower than the other control formulations, Formulation 1 and 3. There was a delay before this sample was analysed allowing the agglomeration to complete, thereby illustrating the technical challenge experienced with handling glycopyrrolate (see FIG. 21).

The methodologies used to create Formulations 7 and 8 demonstrate that co-jet milling with magnesium imparts greater flexibility to the conditioning process negating the need for agitation or turning of the formulation during the condition process (see FIG. 25 and FIG. 26).

The span for Formulation 2 is generally superior to Formulation 1 but the span calculation is affected by disproportionately high $D_{90}$ values. Table 2 clearly demonstrates that a co-jet milled and conditioned product is able to retain a span value less than 50 prior to blending with carrier particles.

In addition to the data on particle size, DVS analysis was performed on many of the glycopyrrolate samples, both directly after milling and after conditioning. These DVS traces demonstrate that immediately after milling the micronized glycopyrrolate is physically unstable, adsorbing and absorbing moisture, despite initially possessing an acceptable particle size distribution (see FIGS. 4 and 27). In contrast, conditioned micronised glycopyrrolate adsorbs moisture onto its surface in an ordered and predictable manner (depicted by the curved solid trace) in response to the changes in vapour present in the DVS chamber (depicted by the angular dotted trace) and similarly releases this surface moisture when conditions are moderated (see FIGS. 28, 30 and 32). The DVS analysis also shows that a "co-jet milled and conditioned product" whilst initially possessing significant amounts of amorphous material (see FIGS. 29 and 35) also achieves a physically stable state (see FIGS. 30, 31, 33, 34 and 36). In some cases, peaks may still be present on the DVS trace (solid line) for the conditioned material but these are fewer in number than for the starting material, indicating a reduction in amorphous material as a result of the conditioning process. A further indicator that the amorphous material has been reduced is the height of these peaks. The reduced peak height corresponds to a reduced change in mass over the duration of the DVS analysis procedure meaning that less moisture has been absorbed by the sample (see FIG. 29 or FIG. 35). This comparison is possible because the formulations have similar surface areas.

Formulations 13a-d

Four separate glycopyrrolate formulations were made and analysed as follows:

Particle Size Analysis (Dry Analysis)

The particle size distribution for the micronized glycopyrrolate formulations was determined by MALVERN MASTERSIZER® analysis (MALVERN MASTERSIZER® 3000, using the Aero S dry dispersion method at 4 Bar and a feed rate of between 30-40%). The optical properties used included a refractive index of 1.52 and an absorption value of 1.0.

Particle Size Analysis (Wet Analysis)

The particle size distribution for the micronized glycopyrrolate formulations was determined by MALVERN MASTERSIZER® 3000 using the Hydro MV wet dispersion unit as follows: the dispersion unit was filled with iso-octane (2,2,4-trimethylpentane). The pump speed was set to 3000 rpm. Ten millilitres of 0.1% lecithin in iso-octane was added to approximately 10 mg of the micronized glycopyrrolate formulation, this pre-dispersion was then sonicated for 3 minutes using a Sonopuls sonic probe at 50% intensity. The dispersed particles were added to the dispersion unit to reach an obscuration of 5-15%. The optical properties used included a refractive index of 1.52 and an absorption value of 1.0 for the glycopyrrolate, and a refractive index of 1.45 and an absorption value of 1.0 for the magnesium stearate and a refractive index of 1.391 for the iso-octane. Six replicates were performed per measurement.

Dynamic Vapour Sorption

The amorphous content for micronized glycopyrrolate was assessed by DVS using an SMS DVS Advantage instrument which was set to a temperature of 25° C. The humidity was increased from 0-90% RH then returned to 0% RH in steps of 10% RH, changes between steps which were triggered by a mass change of 0.0001 (% dm/dt).

Formulations 13a (Dry milling gas) and 13b (Humid milling gas) Unmicronised glycopyrrolate (15 g, $D_{10}$=20.6 µm, $D_{50}$=148.7 µm, $D_{90}$=409.7 µm determined by MALVERN MASTERSIZER® 3000 wet analysis method) was pre-stirred in a glass beaker using a metal spatula for 30 seconds before micronization in an AS-50 spiral jet mill (Inlet pressure=5 Bar, Grinding Pressure=3 Bar, Averaged Feed Rate=2 g/min). Formulation 13a was produced by using a dry milling gas having a humidity <20% RH (2.8-3.5% RH). Formulation 13b was produced by using a milling gas at elevated humidity (31.6-36.2% RH). The humidities were measured by a portable hygrometer with the probe placed in the exiting gas stream at the outlet of the collection vessel. Samples of the freshly micronized glycopyrrolate were immediately analysed using DVS, wet and dry particle size analysis. The micronized formulations were then immediately conditioned in an open jar in which each micronized glycopyrrolate formulation was subjected to the following conditioning parameters: 21.8° C., with ventilating air at 43.2% RH passing over and through the powder bed at a rate of less than 0.1 cm$^3$/s with the volume ratio of ventilating atmosphere to poured bulk powder being more than 1:1. Whilst undergoing these conditioning parameters, samples of the micronized formulation were then analysed using wet and dry particle size analysis at 10, 30, 45, 60, 90 and 120 minutes post milling.

Formulations 13c (Humid Milling Gas and Magnesium Stearate) and 13d (Dry Milling Gas and Magnesium Stearate)

Unmicronised glycopyrrolate (14.25 g, $D_{10}$=20.6 µm, $D_{50}$=148.7 µm, $D_{90}$=409.7 µm determined by MALVERN MASTERSIZER® 3000 wet analysis method) was pre-stirred with magnesium stearate (0.75 g, $D_{10}$=2.8 µm, $D_{50}$=8.8 µm, $D_{90}$=27.4 µm determined by MALVERN MASTERSIZER® 3000 wet analysis method) in a glass beaker using a metal spatula for 30 seconds before micronization in an AS-50 spiral jet mill (Inlet pressure=5 Bar, Grinding Pressure=3 Bar, Averaged Feed Rate=2 g/min). Formulation 13c was produced by using a milling gas at elevated humidity (32.4-37.1% RH). Formulation 13d was produced by using a dry milling gas having a humidity <20% RH (3.4-3.9% RH). The humidities were measured by a portable hygrometer with the probe placed in the exiting gas stream at the outlet of the collection vessel. Samples of the freshly co-micronized glycopyrrolate were immediately analysed using OVS, wet and dry particle size analysis. The co-micronized formulations were then immediately conditioned in an open jar in which each co-micronized glycopyrrolate formulation was subjected to the following conditioning parameters: 21.8° C., with ventilating air at 43.2% RH passing over and through the powder bed at a rate of less than 0.1 cm$^3$/s with the volume ratio of ventilating atmosphere to poured bulk powder being more than 1:1. Whilst undergoing these conditioning parameters, samples of the micronized formulation were then analysed using wet and dry particle size analysis at 10, 30, 45, 60, 90 and 120 minutes post co-micronisation.

Results: Formulation 13a-d

TABLE 3

Particle size (µm) distributions for Formulation 13a following wet analysis (left-hand column) or dry analysis (right-hand column) using the MALVERN MASTERSIZER ®.

| Time (Minutes) | D10 | | D50 | | D90 | |
|---|---|---|---|---|---|---|
| 0 | 0.81 | 1.11 | 2.05 | 250 | 3.9 | 1340 |
| 10 | — | 187 | — | 762 | — | 1860 |
| 30 | 1.18 | 141 | 3.47 | 610 | 74.9 | 1100 |
| 45 | 1.2 | 162 | 3.49 | 680 | 10.6 | 1500 |
| 60 | 1.18 | 104 | 3.38 | 563 | 7.88 | 1070 |
| 90 | 1.25 | 120 | 3.64 | 618 | 11.2 | 1300 |
| 120 | 1.22 | 91.3 | 3.45 | 610 | 8.82 | 1360 |

TABLE 4

Particle size (µm) distributions for Formulation 13b following wet analysis (left-hand column) or dry analysis (right-hand column) using the MALVERN MASTERSIZER ®.

| Time (Minutes) | D10 | | D50 | | D90 | |
|---|---|---|---|---|---|---|
| 0 | 1.38 | 0.355 | 4.06 | 2.74 | 9.08 | 9.17 |
| 10 | 1.39 | 0.339 | 4.41 | 2.55 | 10.5 | 8.91 |
| 30 | 1.38 | 0.387 | 4.77 | 2.82 | 20.5 | 11.1 |

TABLE 4-continued

Particle size (μm) distributions for Formulation 13b following wet analysis (left-hand column) or dry analysis (right-hand column) using the MALVERN MASTERSIZER ®.

| Time (Minutes) | D10 | | D50 | | D90 | |
|---|---|---|---|---|---|---|
| 45 | 1.47 | 0.372 | 4.85 | 2.68 | 13.1 | 9.45 |
| 60 | 1.34 | 0.38 | 4.54 | 2.79 | 15.9 | 9.70 |
| 90 | 1.41 | 0.381 | 4.94 | 2.81 | 20.4 | 9.58 |
| 120 | 1.39 | 0.385 | 4.77 | 2.81 | 18.7 | 9.55 |

TABLE 5

Particle size (μm) distributions for Formulation 13c following wet analysis (left-hand column) or dry analysis (right-hand column) using the MALVERN MASTERSIZER ®.

| Time (Minutes) | D10 | | D50 | | D90 | |
|---|---|---|---|---|---|---|
| 0 | 1.7 | 2.12 | 12.8 | 41.3 | 224 | 267 |
| 10 | 1.61 | 1.98 | 11.9 | 50.6 | 137 | 282 |
| 30 | 1.42 | 2.40 | 7.74 | 54.9 | 54.8 | 306 |
| 45 | 1.46 | 2.34 | 8.34 | 49.9 | 61.4 | 271 |
| 60 | 1.43 | 2.32 | 7.75 | 49.0 | 51.3 | 275 |
| 90 | 1.56 | 2.26 | 10.5 | 46.5 | 133 | 259 |
| 120 | 1.53 | 2.19 | 9.57 | 43.4 | 120 | 256 |

TABLE 6

Particle size (μm) distributions for Formulation 13d following wet analysis (left-hand column) or dry analysis (right-hand column) using the MALVERN MASTERSIZER ®.

| Time (Minutes) | D10 | | D50 | | D90 | |
|---|---|---|---|---|---|---|
| 0 | 0.626 | 0.269 | 1.52 | 1.35 | 2.91 | 4.56 |
| 10 | 0.630 | 0.268 | 1.50 | 1.28 | 2.77 | 3.70 |
| 30 | 0.635 | 0.271 | 1.50 | 1.31 | 2.78 | 4.19 |
| 45 | 0.617 | 0.272 | 1.47 | 1.32 | 2.73 | 4.71 |
|  | 0.619 | 0.271 | 1.48 | 1.28 | 2.73 | 3.86 |
| 90 | 0.616 | 0.278 | 1.47 | 1.38 | 2.73 | 6.20 |
| 120 | 0.631 | 0.264 | 1.50 | 1.25 | 2.77 | 3.40 |

Discussion: Formulations 13a-d

When milled under dry conditions, freshly jet milled glycopyrrolate contains substantial amounts of amorphous material as confirmed by the DVS data for Formulation 13a (FIG. 37). It is the presence of this amorphous material in the company of moisture that, if not controlled correctly, leads to the formation of large agglomerates in an unpredictable fashion (FIG. 41, see Formulation 13a). In the case of Formulation 13a, three separate samples were taken from jet milled powder and briefly transported in sealed scintillation vials for DVS, Wet PSD and Dry PSD analysis. First, the DVS analysis was started, followed by the Wet and Dry PSD analysis. Formulation 13a developed a significant amount of large agglomerates in the sealed scintillation vials prior to dry PSD analysis as shown by the $D_{90}$ and $D_{50}$ values (FIGS. 41 and 44 respectively). The dry PSD analysis also demonstrates that Formulation 13a had equivalent $D_{10}$ values to the other formulations 13b-d demonstrating that Formulation 13a still had a micronized component (FIG. 47). The wet PSD analysis shows that Formulation 13a had small PSD values prior to and during the conditioning process indicating that these agglomerates were weak in structure (FIGS. 50, 53 and 55). The large weak agglomerates remained throughout the conditioning process with a $D_{90}$ never dropping below 1070 μm (FIG. 41) as measured by dry particle size analysis (Table 3).

When milled under humid conditions, freshly jet milled glycopyrrolate formulations contain no amorphous material; thus, in agreement with the teaching of WO1999054048, WO2000032165 and WO2000032313, the humid milling conditions reduce the formation of amorphous material on the surface of micronized glycopyrrolate. The DVS trace demonstrates that no amorphous material was present in this freshly micronized glycopyrrolate (t=0) (see FIG. 38). Without this amorphous material on the surface of micronized glycopyrrolate, the particles do not form large agglomerates and remain respirable (i.e. $D_{50}$ less than 5 μm, see Table 4, FIG. 42, FIG. 45 and FIG. 48). The wet and dry particle size analysis showed that this freshly micronized glycopyrrolate formulation remained stable throughout the conditioning process with a $D_{90}$ never exceeding 11.1 μm (Table 4).

Similarly, freshly co-jet milled glycopyrrolate and magnesium stearate formulations contain minimal amorphous material when co-jet milled under humid conditions (Formulation 13c), as is apparent from the DVS trace (FIG. 39). Without this amorphous material on the surface of micronized glycopyrrolate, the co-micronised particles do not form large agglomerates ($D_{90}$>1000 μm) unlike Formulation 13a. The combination of the humidity and the magnesium stearate, however, reduces the milling efficiency resulting in an initial $D_{50}$ of 12.8 μm for Formulation 13c (see Table 5, Wet Analysis) compared to 2.05 μm, 4.06 μm and 1.52 μm (Wet Analysis for Formulations 13a, b and d respectively).

As expected, the freshly co-jet milled glycopyrrolate and magnesium stearate formulations contain amorphous material when co-jet milled under dry conditions, as is apparent from the OVS trace for Formulation 13d (FIG. 40). Surprisingly however, the wet and dry particle size analysis showed that Formulation 13d consistently had the best particle size distribution as shown by $D_{10}$, $D_{50}$ or $D_{90}$ across all time points when compared with the control Formulations 13a-c and remained stable and unagglomerated throughout the conditioning process with a $D_{90}$ never going above 6.2 μm (see Table 6).

Therefore, surprisingly, Formulation 13d in which amorphous material was present after milling, produced a better particle size distribution than formulation 13c in which little amorphous material was present after milling.

Formulations 14a-b

Unmicronised glycopyrrolate, 50 g, ($D_{10}$=20.6 μm, $D_{50}$=148.7 μm, $D_{90}$=409.7 μm determined by MALVERN MASTERSIZER® 3000 wet analysis method) was mixed with magnesium stearate, 1.85 g, ($D_{10}$=2.8 μm, $D_{50}$=8.8 μm, $D_{90}$=27.4 μm determined by MALVERN MASTERSIZER® 3000 wet analysis method) in a Turbula® blender for 5 hours.

A sample of the tumble blended glycopyrrolate and magnesium stearate was co-micronised using an AS-50 spiral jet mill (Inlet pressure=5 Bar, Grinding Pressure=3 Bar, Averaged Feed Rate=2 g/min) using a dry milling gas (3.5-3.8% RH) as measured by a portable hygrometer with the probe placed in the exiting gas stream at the outlet of the collection vessel. Samples of this freshly co-micronized glycopyrrolate were immediately analysed using OVS and wet particle size analysis ($D_{10}$=0.601 μm, $D_{50}$=1.42 μm, $D_{90}$=2.80 μm). The OVS trace (FIG. 57) demonstrates that significant amounts of amorphous material were initially present in this freshly co-micronized glycopyrrolate.

Control Experiment: Formulation 14a (Co-Jet Milling with Dry Gas then Blending with Lactose)

A sample of the freshly co-micronized glycopyrrolate and magnesium stearate was then immediately blended with LH200 lactose (99.7% w/w of final composition) using a TRV High Shear Mixer (1 L) for 10 minutes at 8 m/s tip speed. The resulting formulation was filled in aliquots of 25 mg into size 3 HPMC capsules. The resulting capsules were tested for aerosol performance (% FPF(EO)) using the NGI at a flow rate of 90 Umin fired from a Low Resistance Monohaler, either immediately, 24 hrs or 1 week (168 hrs) after manufacture with FPF(ED)<5 μm and FPF(ED)<3 μm calculated at these time points (FIG. 58 and FIG. 59 respectively).

Formulation 14b (Co-Jet Milling with Dry Gas, then Conditioning, then Blending with Lactose)

A sample of the freshly co-micronized glycopyrrolate and magnesium stearate was then immediately subjected to a conditioning step using ventilating air at 22.0° C./47.0% RH passing over and through the powder bed at a rate of less than 0.1 cm$^3$/s with the volume ratio of ventilating atmosphere to poured bulk powder being more than 1:1 as conditioning parameters for 1 hr. It was then blended with LH200 lactose (99.7% w/w of final composition) and analysed according to Example 14a (FIG. 58 and FIG. 59 respectively).

Discussion: Formulation 14a and 14b

FIGS. 58 and 59 show the reduction in FPF over the course of a week in both formulations, which is attributed to powder relaxation due to static dissipation. The TRV high energy blending machine is very efficient at breaking apart stubborn agglomerates; particularly an amorphous active particle adhering to a lactose carrier but does impart static to the freshly blended formulation.

The formulation made according to Example 14b has a data mean, data range and rate of decrease in FPF(ED)<5 μm or FPF(ED)<3 μm which are all distinct and superior to Example 14a after 24 hrs and 1 week, demonstrating that there is a benefit of conditioning co-micronized glycopyrrolate before blending with lactose.

The invention claimed is:

1. A method of making a dry powder formulation, the method comprising co-jet milling unmicronised glycopyrrolate and magnesium stearate with milling gas having a humidity below 20% Relative Humidity to produce micronized composite particles, wherein the micronized composite particles are then subjected to a conditioning step comprising exposure of the micronized composite particles to humidity in the range of 10%-95% Relative Humidity at temperatures ranging from 5° C. to 88° C. for at least 60 minutes, and wherein the fraction of the conditioned co-jet milled formulation which is greater than 10 μm is less than 20% by volume or mass immediately after the co-jet milling and after the conditioning process as suitably determined by laser diffraction equipment.

2. The method according to claim 1, wherein the conditioning is initiated within 30 minutes of completing the co-jet milling of the glycopyrrolate and magnesium stearate.

3. The method according to claim 1, wherein the magnesium stearate is co-jet milled in an amount ranging from 1 to 25% (w/w) magnesium stearate by weight of the co-jet milled combination of glycopyrrolate and magnesium stearate.

4. The method according to claim 1, wherein the conditioning humidity is in the range of 30-90% RH.

5. The method according to claim 4, wherein the conditioning step further comprises subjecting the micronized composite particles to a ventilating atmosphere having relative humidity in the range of 10%-95% RH wherein the atmosphere is air.

6. The method according to claim 5, wherein the ventilating atmosphere passes over and through a powder bed comprising micronized composite particles at a rate of less than 100 cm$^3$/s.

7. The method according to claim 6, wherein the volume ratio of ventilating atmosphere to a poured bulk powder is more than 1:1.

8. The method according to claim 1, wherein the conditioning step is carried out for at least 75 minutes.

9. The method according to claim 1, wherein the conditioning step includes exposing the micronized composite particles to a temperature in the range from 10° C. to 50° C.

10. The method according to claim 1, wherein the micronized composite particles are blended with a carrier, optionally after the conditioning step.

11. The method according to claim 10, wherein the micronized composite particles are present in an amount of less than 5% by weight of the formulation.

12. The method according to claim 1, wherein the conditioning step takes place by distributing the micronized composite particles on a surface, optionally wherein the conditioning step takes place on a tray.

13. The method according to claim 1, wherein the conditioning step involves exposing the micronized composite particles to the humidity for sufficient time for amorphous glycopyrrolate to re-crystallise after co-jet milling, as determined by dynamic vapour sorption.

14. The method according to claim 1, wherein the conditioning step involves powder agitation, optionally wherein the agitation is intermittent powder agitation.

15. The method according to claim 14, wherein the powder agitation takes places within 30 minutes of completing the milling of the glycopyrrolate and magnesium stearate.

16. The method according to claim 14, wherein the powder agitation involves a fluidised bed.

17. The method according to claim 14, wherein the powder agitation is provided by a Resonance Acoustic Mixer.

18. The method according to claim 1, wherein the milling gas has a humidity below 15% Relative Humidity.

19. The method according to claim 1, wherein the milling gas is chosen from air, nitrogen or helium or combination thereof.

20. The method according to claim 1, wherein the co-jet milling is carried out at an averaged powder feed rate ranging from 0.1 and 50 g/min.

21. The method according to claim 1, wherein the co-jet milling is carried out at an inlet pressure ranging from 3 and 12 bar.

22. The method according to claim 1, wherein the co-jet milling is carried out using a grinding pressure and an inlet pressure and wherein the grinding pressure is more than 2 bar below the inlet pressure.

23. The method according to claim 22, wherein the grinding pressure is carried out in the range of 1 and 10 bar.

24. The method according to claim 1, wherein the dry powder composition further comprises a beta-2 adrenoceptor agonist.

25. The method according to claim 1, wherein the dry powder composition further comprises an active agent chosen from salmeterol, indacaterol, and mometasone.

26. A method of making a dry powder formulation, the method comprising co jet milling unmicronised glycopyrrolate and magnesium stearate with milling gas having a humidity below 20% Relative Humidity to produce micronized composite particles, wherein the micronized composite particles are then subjected to a conditioning step comprising exposure of the micronized composite particles to humidity in the range of 10%-95% Relative Humidity at temperatures ranging from 5° C. to 88° C. for at least 10 minutes, and wherein the fraction of the conditioned co-jet milled formulation which is greater than 10 μm is less than 20% by volume or mass immediately after the co-jet milling and after the conditioning process as suitably determined by laser diffraction equipment.

27. The method according to claim 2, wherein the conditioning is initiated immediately after completing the co-jet milling of the glycopyrrolate and magnesium stearate.

28. The method according to claim 1, wherein the fraction of the conditioned co jet milled formulation which is greater than 10 μm is less than 5% by volume or mass immediately after the co jet milling and after the conditioning process as suitably determined laser diffraction equipment.

29. The method according to claim 3, wherein the magnesium stearate is co-jet milled in an amount ranging from 5 to 7.5% (w/w) magnesium stearate by weight of the co-jet milled combination of glycopyrrolate and magnesium stearate.

30. The method according to claim 4, wherein the conditioning humidity is in the range of 60-87% RH.

31. The method according to claim 5, wherein the conditioning step further comprises subjecting the micronized composite particles to a ventilating atmosphere having relative humidity in the range of 60-87%, wherein the atmosphere is air.

32. The method according to claim 6, wherein the ventilating atmosphere passes over and through a powder bed comprising micronized composite particles at a rate of less than about 0.001 cm$^3$/s.

33. The method according to claim 7, wherein the volume ratio of ventilating atmosphere to poured bulk powder is more than 10,000,000:1.

34. The method according to claim 8, wherein the conditioning step is carried out for at least 48 hours.

35. The method according to claim 9, wherein the conditioning step includes exposing the micronized composite particles to a temperature in the range from 24° C. to 50° C.

36. The method according to claim 10, wherein the micronized composite particles are blended with alpha-lactose monohydrate, optionally after the conditioning step.

37. The method according to claim 11, wherein the micronized composite particles are present in an amount of less than 0.5% by weight of the formulation.

38. The method according to claim 15, wherein the powder agitation takes places immediately after completing the milling of the glycopyrrolate and magnesium stearate.

39. The method according to claim 18, wherein the milling gas has a humidity below 2.5% Relative Humidity.

40. The method according to claim 19, wherein the milling gas is air.

41. The method according to claim 20, wherein the co-jet milling is carried out at an averaged powder feed rate ranging from 1.5 and 5 g/m in.

42. The method according to claim 21, wherein the co-jet milling is carried out at an inlet pressure ranging from 5 and 9 bar.

43. The method according to claim 23, wherein the grinding pressure is carried out in the range of 3 and 7 bar.

44. The method according to claim 24, wherein the beta-2 adrenoceptor agonist is chosen from albuterol (salbutamol), metaproterenol, terbutaline, salmeterol, fenoterol, and procaterol.

45. The method according to claim 24, wherein the beta-2 adrenoceptor agonist is (R)-5-[2-(5,6-diethyl-indan-2-ylamino)-1-hydroxy-ethyl]-8-hydroxy-1H-quinolin-2-one maleate.

46. The method according to claim 24, wherein the beta-2 adrenoceptor agonist is chosen from formoterol, carmoterol, and pharmaceutically acceptable salts thereof.

47. A method of making a dry powder formulation, the method comprising co-jet milling unmicronised glycopyrrolate and magnesium stearate with milling gas having a humidity below 20% Relative Humidity to produce micronized composite particles, wherein the micronized composite particles are then subjected to a conditioning step comprising exposure of the micronized composite particles to humidity in the range of 10%-95% Relative Humidity at temperatures ranging from 5° C. to 88° C. for at least 60 minutes.

48. A method of making a dry powder formulation, the method comprising co-jet milling unmicronised glycopyrrolate and magnesium stearate with milling gas having a humidity below 20% Relative Humidity to produce micronized composite particles, wherein the micronized composite particles are then subjected to a conditioning step comprising exposure of the micronized composite particles to humidity in the range of 10%-95% Relative Humidity at temperatures ranging from 5° C. to 88° C. for at least 10 minutes.

* * * * *

UNITED STATES PATENT AND TRADEMARK OFFICE
CERTIFICATE OF CORRECTION

PATENT NO. : 10,532,041 B2  
APPLICATION NO. : 15/509769  
DATED : January 14, 2020  
INVENTOR(S) : Fergus Manford Page 1 of 1

It is certified that error appears in the above-identified patent and that said Letters Patent is hereby corrected as shown below:

In the Claims

Claim 26, Column 36, Line 64, "co jet" should read as --co-jet--.

Claim 28, Column 37, Line 14, "co jet" should read as --co-jet--.

Claim 28, Column 37, Line 16, "co jet" should read as --co-jet--.

Signed and Sealed this  
Seventh Day of April, 2020

Andrei Iancu  
*Director of the United States Patent and Trademark Office*